US007326782B2

(12) United States Patent
Thomas et al.

(10) Patent No.: US 7,326,782 B2
(45) Date of Patent: Feb. 5, 2008

(54) METABOLIC ENGINEERING OF VIOMYCIN BIOSYNTHESIS

(75) Inventors: Michael G. Thomas, Madison, WI (US); Yolanda A. Chan, Madison, WI (US); Sarah G. Ozanick, Milwaukee, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 387 days.

(21) Appl. No.: 10/925,357

(22) Filed: Aug. 23, 2004

(65) Prior Publication Data

US 2005/0042726 A1 Feb. 24, 2005

Related U.S. Application Data

(60) Provisional application No. 60/496,760, filed on Aug. 21, 2003.

(51) Int. Cl.

| | |
|---|---|
| *C12P 21/04* | (2006.01) |
| *C12N 9/00* | (2006.01) |
| *C12N 15/52* | (2006.01) |
| *C11N 15/74* | (2006.01) |

(52) U.S. Cl. .................. 536/23.2; 536/23.7; 435/71.1; 435/71.3; 435/252.3; 435/252.35; 930/190

(58) Field of Classification Search .................... None
See application file for complete search history.

(56) References Cited

U.S. PATENT DOCUMENTS

| | | | |
|---|---|---|---|
| 2,633,445 | A | 3/1953 | March et al. |
| 3,143,168 | A | 8/1964 | Huchleberry |
| 4,340,674 | A | 7/1982 | Manis et al. |
| 4,343,906 | A | 8/1982 | Reusser et al. |
| 4,362,816 | A | 12/1982 | Reusser |
| 4,416,994 | A | 11/1983 | Nakatsukasa et al. |
| 4,477,571 | A | 10/1984 | Chang et al. |
| 4,551,433 | A | 11/1985 | DeBoer |
| 4,935,340 | A | 6/1990 | Baltz et al. |
| 5,393,665 | A | 2/1995 | Fayerman et al. |
| 5,605,793 | A | 2/1997 | Stemmer |
| 5,672,497 | A | 9/1997 | Cox et al. |
| 5,811,238 | A | 9/1998 | Stemmer et al. |

(Continued)

FOREIGN PATENT DOCUMENTS

| | | |
|---|---|---|
| WO | WO 00/53737 | 9/2000 |

OTHER PUBLICATIONS

August et al. (1998) "Biosynthesis of the Ansamycin Antibiotic Rifamycin: Deductions from the Molecular Analysis of the *rif* Biosynthetic Gene Cluster of *Amycolatopsis mediterranei* S699," *Chem. Biol.* 5:69-79.

(Continued)

*Primary Examiner*—Nashaat T. Nashed
*Assistant Examiner*—William W. Moore
(74) *Attorney, Agent, or Firm*—Greenlee, Winner and Sullivan, P.C.

(57) ABSTRACT

The invention provides a nucleic acid molecule comprising at least a functional fragment of the viomycin biosynthetic gene cluster, functional proteins encoded by the cluster, expression cassettes and recombinant host cells comprising a functional fragment of the viomycin cluster, and methods for generating biologically active agents using the nucleic acid molecules of the present invention.

47 Claims, 9 Drawing Sheets

U.S. PATENT DOCUMENTS

| | | | |
|---|---|---|---|
| 5,824,513 | A | 10/1998 | Katz et al. |
| 5,830,727 | A | 11/1998 | Wang et al. |
| 5,834,252 | A | 11/1998 | Stemmer et al. |
| 5,837,458 | A | 11/1998 | Minshull et al. |
| 5,848,956 | A | 12/1998 | Grehner |
| 6,391,583 | B1 | 5/2002 | Hutchinson et al. |
| 6,495,348 | B1 | 12/2002 | Sherman et al. |
| 6,689,611 | B1 | 2/2004 | Stutzman-Engwall et al. |

OTHER PUBLICATIONS

Barnes et al. (1991) "Tuberculosis in Patients with Human Immunodeficiency Virus Infection," *N. Engl. J. Med.* 324:1644-50.

Bartz et al. (1951) "Viomycin, a New Tuberculostatic Antibiotic," *Am. Rev. Tuberc.* 63:4-6.

Bibb et al. (1985) "Nucleotide Sequences Encoding and Promoting Expression of Three Antibiotic Resistance Genes Indigenous to *Streptomyces*," *Mol. Gen. Genet.* 199:26-36.

Bierman et al. (1992) "Plasmid Cloning Vectors for the Conjugal Transfer of DNA from *Escherichia coli* to *Streptomyces* spp," *Gene* 116:43-9.

Bloom et al. (1999) "The Death and Resurrection of Tuberculosis," *Nat. Med.* 5:872-874.

Bloom et al. (1992) "Tuberculosis: Commentary on a Reemergent Killer," *Science* 257:1055-1064.

Bormann et al. (1996) "Cloning and Heterologous Expression of the Entire Set of Structural Genes for Nikkomycin Synthesis from *Streptomyces tendae* Tu901 in *Streptomyces lividans*," *J. Bacteriol.* 178:1216-1218.

Brautaset, T. et al. ((2000) "Biosynthesis of the polyene antifungal antibiotic nystatin in *Streptomyces noursei* ATCC 11455: analysis of the gene cluster and deduction of the biosynthetic pathway," *Chemistry & Biology* 7:395-403.

Carter et al. (1974) "Biosynthetis of Viomycin. I. Origin of Alpha, Beta-Diaminopropionic Acid and Serine," *Biochemistry* 13:1221-7.

Challis et al. (2000) "Predictive, Structure-Based Model of Amino Acid Recognition by Nonribosomal Peptide Synthetase Adenylation Domains," *Chem. Biol.* 7:211-24.

Chater et al. (1985) "Resistance, Regulatory and Production Genes for the Antibiotic Methylenomycin are Clustered," *EMBO J.* 4:1893-1897.

Chiu et al. (2001) "Molecular Cloning and Sequence Analysis of the Complestatin Biosynthetic Gene Cluster," *Proc. Natl. Acad. Sci. USA* 98(15):8548-8553.

Dalbadie-McFarland et al. (1982) "Oligonucleotide-Directed Mutagenesis as a General and Powerful Method for Studies of Protein Function," *Proc. Natl. Acad. Sci. USA* 79:6409-6413.

DeMong et al. (2003) "Asymetric Synthesis of (2S, 3R) -Capreomycidine and the Total Synthesis of Capreomycin IB," *J. Am. Chem. Soc.* 125:8561-8565.

DeMong et al. (2002) "The Asymmetric Synthesis of (2S,3R)-Capreomycidine," *Tetrahedron Lett.* 42:3529-3532.

Dirlam et al. (1997) "Cyclic Homopentapeptides 1. Analogs of Tuberactinomycins and Capreomycin with Activity Against Vancomycin-Resistant Enterococci and *Pasteurella*," *Bioorg. Medicin. Chem. Lett.* 7:1139-1147.

Duncan et al. (2000) "Approaches to Tuberculosis Drug Development," In G. F. Hatfull and W. R. J. Jacobs (ed.), *Molecular Genetics of Mycobacteria*. ASM Press, Washington, D.C, pp. 297-307.

Dye et al. (2002) "Erasing the World's Slow Stain: Srategies to Beat Multidrug-Resistant Tuberculosis," *Science* 295:2042-6.

Ehmann et al. (1999) "Lysine Biosynthesis in *Saccharomyces cerevisiae*: Mechanism of α-Aminoadipate Reductase (Lys2) Involves Posttranslational Phosphopantetheinylation by Lys5," *Biochemistry* 38(19):6171-617.

Ehrlich et al. (1951) "Antimicrobial Activity of *Streptomyces floridae* and of Viomycin," *Am. Rev. Tuberc.* 63:7-16.

Evans et al. (1989) "High Efficiency Vectors for Cosmid Microcloning and Genomic Analysis," *Gene* 79:9-20.

Fattorini et al. (1999) "Activity of 16 Antimicrobial Agents Against Drug-Resistant Strains of Mycobacterium Tuberculosis," *Microb. Drug Resist.* 5:265-270.

Finlay et al. (1951) "Viomycin a New Antibiotic Activity Against Mycobacteria," *Am. Rev. Tuberc.* 63:1-3.

GenBank Accession No. AY225601S1, Aug. 29, 2003 [Yin].
GenBank Accession No. AY225601S2, Aug. 29, 2003 [Yin].
GenBank Accession No. AY225601S1, Aug. 5, 2003 [Yin].
GenBank Accession No. AY225601S2, Aug. 5, 2003[Yin].
GenBank Accession No. AA066425, Aug. 29, 2003 [Yin].
GenBank Accession No. AA066425, Aug. 5, 2003 [Yin].
GenBank Accession No. AA066426, Aug. 29, 2003 [Yin].
GenBank Accession No. AA066427, Aug. 29, 2003 [Yin].
GenBank Accession No. AA066428, Aug. 29, 2003 [Yin].
GenBank Accession No. AAP92509, Aug. 25, 2003 [Thomas].
GenBank Accession No. AAP92510, Aug. 25, 2003 [Thomas].
GenBank Accession No. AY263398, Aug. 25, 2003 [Thomas].

Gould et al. (1992) Biosynthesis of Capreomycin: 1. Incorporation of Arginine, *J. Org. Chem.* 57:5214-5217.

Grammel et al. (2002) "A beta-lysine Adenylating Enzyme and a Beta-lysine Binding Protein Involved in Poly Beta-lysine Chain Assembly in Nourseothricin Synthesis in *Streptomyces noursei*," *Eur. J. Biochem.* 269:347-357.

Hermann et al. (1998) "RNA as a Drug Target: Chemical, Modelling, and Evolutionary Tools," *Curr. Opin. Biotechnol.* 9:66-73.

Hojati et al. (2002) "Structure, Biosynthetic Origin, and Engineered Biosynthesis of Calcium-Dependent Antibiotics from *Streptomyces coelicolor*," *Chemistry and Biology.* 9:1175-1187.

Jackson et al. (2002) "Studies on the Formation and Incorporation of *Streptolidine* in the Biosynthesis of the Peptidyl Nudleoside Antibiotic Streptothricin F," *J. Org. Chem.* 67(9):2934-2941.

James et al. (1998) "The Therapeutic Potential of Ribozymes," *Blood* 91:371-82.

Jenne et al. (2001) "Rapid Identification and Characterization of Hammerhead-Ribozyme Inhibitors Using Fluorescence-Based Technology," *Nat. Biotechnol.* 19:56-61.

Ju et al. (2004) "Conversion of (2S)-Arginine to (2S,3R)-Capreomycidine by VioC and VioD from the Viomycin Biosynthetic Pathway of *Streptomyces* sp. Strain ATCC11861," *Chem. Biochem.* 5: 1-9 (in press).

Kieser et al. (1982) *Mol. Gen. Genet.* 185:223-238.

Kitagawa et al. (1979) "Studies on Viomycin XIV Roles of Basic and Cyclic Moieties in the Antimicrobial Activity of Viomycin," *Chem. Pharm. Bull.* 27:2551-2556.

Kitagawa et al. (1976) "Studies on Viomycin. IX. Amino Acid Derivatives of Viomycin," *Chem. Pharm. Bull.* 24:1324-1330.

Kitagawa et al. (1975) "Studies on Viomycin. VIII. Selective Modifications of the Terminal Amino Groups of Viomycin," *Chem. Pharm. Bull.* 23:2123-2127.

Konz et al. (1999) "How do Peptide Synthetases Generate Structural Diversity?" *Chem. Biol.* 6:R39-R48.

Kramnik et al. (2000) "Genetic Control of Resistance to Experimental Infection with Virulent *Mycobacterium tuberculosis*," *Proc. Natl. Acad. Sci. USA* 97:8560-8565.

Kunkel, T.A. (1985) "Rapid and Efficient Site-Specific Mutagenesis without Phenotypic Selection," *Proc. Natl. Acad. Sci. USA* 82:448-492.

Linde et al. (1997) "Cyclic Homopentapeptides 3. Synthetic Modifications to the Capreomycins and Tuberactinomycins: Compounds with Activity Against Methicilin-Resistant *Staphylococcus aureus* and Vancomycin-Resistant Enterococci," *Bioorg. Medic. Chem. Lett.* 7:1149-1152.

Lyssikatos et al. (1997) "Cyclic Homopentapeptides 2. Synthetic Modifications of Viomycin," *Bioorg. Medic. Chem. Lett.* 7:1145-1148.

MacNeil et al. (1992) "Analysis of *Streptomyces avermitilis* Genes Required for Avermectin Biosynthesis Utilizing a Novel Integration Vector," *Gene* 111:61-69.

Marahiel et al. (1997) "Modular Peptide Synthetases Involved in Nonribosomal Peptide Synthesis," *Chem. Rev.* 97:2651-2673.

Martin, J. F. (1992) "Clusters of Genes for the Biosynthesis of Antibiotics: Regulatory Genes and Overproduction of Pharmaceuticals," *J. Ind. Microbiol.*, 9:73-90 (Abstract only)

Martin et al. (1989) "Organization and Expression of Genes Involved in the Biosynthesis of Antibiotics and other Secondard Metabolites," *Annu. Rev. Microbiol.* 43:173-206.

Mayer et al. (1954) "Antituberculosis Activity of Vinactane," *Experimentis* 10:335-336.

Morse et al. (1997) "Production of Tuberactinamine A by *Streptomyces griseoverticillatus* var. *Tuberacticus* NRRL 3482 fed with (S)-2-Aminoethyl-L-Cysteine," *J Antibiot* (Tokyo) 50:698-700.

Murray et al. (1998) "Modeling the Impact of Global Tuberculosis Control Strategies," *Proc. Natl. Acad. Sci. USA* 95:13881-13886.

Nagata et al. (1968) "Studies on Tuberactinomycin (tuberactin), a New Antibiotic. I. Taxonomy of Producing Strain, Isolation and Characterization," *J. Antibiot.* 21:681-687.

Nowak-Thompson et al. (1999) "Characterization of the Pyoluteorin Biosynthetic Gene Cluster of *Pseudomonas fluorescens* Pf-5," *J. Bacteriol.* 181:2166-2174.

Patten et al. (1997) "Applications of DNA Shuffling to Pharmaceuticals and Vaccines," *Cur. Op. Biotech.* 8:724-733.

Pelzer et al. (1999) "Identification and Analysis of the Balhimycin Biosynthetic Gene Cluster and Its Use for Manipulating Glycopeptide Biosynthesis in *Amycolatopsis mediterranei* DSM5908," *Antimicrob. Agents Chemother.* 43(7):1565-1573.

Pootoolal et al. (2002) "Assembling the Glycopeptide Antibiotic Scaffold: The Biosynthesis of A47934 from *Streptomyces toyocaensis* NRRL 15009," *Proc. Natl. Acad. Sci. USA* 99:8962-8967.

Rogers et al. (1996) "Inhibition of the Self-Cleavage Reaction of the Human Hepatitis Delta Virus Ribozyme by Antibiotics," *J. Mol. Biol.* 259:916-925.

Schroeder et al. (2000) "Modulation of RNA Function by Aminoglycoside Antibiotics," *EMBO J.* 19:1-9.

Seno et al. (1989) *Structural Organization and Regulation of Antibiotic Biosynthesis and Resistance Genes in Actinomycetes*, CRC Press, Boca Raton, Fla.

Sosio et al. (2003) "The Gene Cluster for the Biosynthesis of the Glycopeptide Antibiotic A40926 by *Nonomuraea* Species," *Chem. Biol.* 10(6):541-549.

Stachelhaus et al. (1999) "The Specificity-Conferring Code of Adenylation Domains in Nonribisomal Peptide Synthetases," *Chem. Biol.* 6:493-505.

Steffensky et al. (2000) "Identification of the Novobiocin Biosynthetic Gene Cluster of *Streptomyces spheroids* NCIB 11891," *Antimicrob. Agents Chemother.* 44:1214-1222.

Thomas et al. (2002) "Conversion of L-Proline to Pyrrolyl-2-Carboxyl-S-PCP During Undecylprodigiosin and Pyoluteorin Biosynthesis," *Chem. Biol.* 9:171-184.

Thomas et al. (2003) "Deciphering Tuberactinomycin Biosynthesis: Isolation, Sequencing, and Annotation of the Viomycin Biosynthetic Gene Cluster," *Antimicrob Agents Chemother*, 47(9):2823-2830.

Trauger et al. (2000) "Heterologous Expression in *Escherichia coli* of the First Module of the Nonribosomal Peptide Synthetase of Chloroeremomycin, an Vancomycin-Type Glycopeptide Antibiotic," 97:3112-3117.

Tsukamura et al. (1989) "Superiority of Enviomycin or Streptomycin Over Ethambutol in Initial Treatment of Lung Disease Caused by Mycobacterium Avium Complex," *Chest* 95:1056-8.

Van Wageningen et al. (1998) "Sequencing and Analysis of Genes Involved in the Biosynthesis of a Vancomycin Group Antibiotic," *Chem. Biol.* 5:155-162.

Von Ahsen et al. (1991) "Antibiotic Inhibition of Group I Ribozyme Function," *Nature* 353:368-370.

Vos et al. (2002) "Effect of Magnesium Ions on the Tertiary Structure of the Hepatitis C Virus IRES and its Affinity for the Cyclic Peptide Antibiotic Viomycin," *Biochem.* 41:5383-5396.

Wakamiya et al. (1977) "Chemical Studies on Tuberactinomyin. XI. Semisyntheses of Tuberactinomycin Analogs with Various Amino Acids in Branched Part," *Bull. Chem. Soc. Jap.* 50:1984-1989.

Wang et al. (1993) "Biosynthesis of Capreomycin. 2. Incorporation of L-serine, L-Alanine, and L-2,3-Diaminopropionic Acid," *J. Org. Chem.* 58:5176-5180.

Wank et al. (1994) "Peptide Antibiotics of the Tuberactinomycin Family as Inhibitors of Group I Intron RNA Splicing," J. Mol. Biol. 236:1001-1010.

Wank et al. (1996) "Antibiotic-Induced Oligomerisation of Group I Intron RNA," J. Mol. Biol. 258:53-61.

Yin et al. (2003) "Identification and Cloning of Genes Encoding Viomycin Biosynthesis from *Streptomyces vinaceus* and Evidence for Involvement of a Rare Oxygenase," *Gene* 312:215-224.

Martin, J. F. (1992) "Clusters of Genes for the Biosynthesis of Antibiotics: Regulatory Genes and Overproduction of Pharmaceuticals," *J. Ind. Microbiol.*, 9:73-90.

Database Geneseq 'Online! Oct. 23, 2002, "S. roseosporus daptomycin non-ribosomal peptide synthetase DptA." XP002324075 retrieved from EBI accession No. GSN: ABP62761 Database accession No. ABP62761 Seq ID No. 002 has 35.32% identity (37.35% ungapped) over 2166 (q:s=23-2119:2994-5110) with subject GSP: ABP62671 disclosed in patent W002059322 published on 20020801. & WO 02/059322 A (Miao, Vivian, Pak, Woon; Brian, Paul; Baltz, Richard, H; Silva, Christ) Aug. 1, 2002.

A.

B.

SEQUENCE LISTING

<160> NUMBER OF SEQ ID NOS: 22

<210> SEQ ID NO 1
<211> LENGTH: 36401
<212> TYPE: DNA
<213> ORGANISM: Streptomyces sp.

<400> SEQUENCE: 1
gggcgcgtga catcccgagg agttaggcga gaaggcgcac ggtgggtgtc cggccgcgga    60

|  |  |  |  |  |
|---|---|---|---|---|
| ccggccctca | tggacgcggc | cctcgaaaca | ccgcgaggag | ggtccttgcc | gaccgcgccc | 120 |
| acccgtcggc | tccagcggcc | cacagcggac | gttcgagggc | cggacacggt | gtcactgccc | 180 |
| agaacggcgg | accccgacca | catgcgctcc | gacgcttgtc | gttcgttggg | gcatcccgac | 240 |
| gacggaagag | cgttatccct | tcggtggagt | ccggcctacc | accgtggtcg | cggtccatga | 300 |
| accgccaaaa | gaaccacccg | tcacagcgac | gaaggaacaa | ttgatcgagc | ttccccggca | 360 |
| cgcgcaccat | ggaacggccg | ccgtaagcga | gcccgatgcc | gggagtctcc | ctgtatggaa | 420 |
| gccagagatg | acgcacatca | cctgcttgcc | ctgacagcat | cgaatgccgc | agcgtcgaac | 480 |
| ggcccgggcg | gccgtgacgc | gacgttcgac | gaactcgtcg | gcgcgcaagc | cgccgcaacg | 540 |
| cccggagcca | ccgccgttgt | tcacgacgac | gggctgctga | cctacgccga | actggacgag | 600 |
| cggagcacgc | ggctcgccca | ccggctgcgg | gccctcggtg | tgcgtgccga | gacacccgtc | 660 |
| ggggtgatgc | tggaacgtga | tccggagctg | gtcgtcgcac | tgctcggcgt | gctgaaggcc | 720 |
| ggcggagcct | tcgtgcccgt | cgacccgacg | taccccggcgg | cgcggatccg | ccacatgctg | 780 |
| gacgactccg | gggcgcgggc | cgtcctgctg | cgccaggagc | tgcgggaccg | gctgcccgag | 840 |
| gacctgcgcg | acgggacggg | acaggtggcg | gtcgtaccgg | tgggcgcgga | gagcggggcc | 900 |
| gggacgtcta | cgcgccggcc | ggtcacgccg | gtcgagcagg | agccacggcc | cgagcgtctg | 960 |
| gcctacatcg | tctacacctc | gggctccacc | ggtctgccca | agggtgtgat | ggtcgagcac | 1020 |
| cgtggcatcg | tcagctatct | gctgggcatg | ctggagcact | tcccgatggg | gccgcgcgac | 1080 |
| cgcatgctgc | aggtcacgtc | gctctccttc | gacgtctccg | tgtacgagat | cttcctgccg | 1140 |
| ctgctgaccg | gcggcgccac | cgtgctcccc | cgctcgggca | gccatacgga | cgccgcctac | 1200 |
| ctgagcgggc | tgatagccga | gcacggcgtg | acgtccttcc | acatggtgcc | ctcactgctg | 1260 |
| cggaccttcg | tggacgggct | cgatccccgg | cagtgcgccg | ggctgcgccg | gatcttcgtc | 1320 |
| agcggagagg | cactcgacac | cacgctggtg | gtcgacgtgc | acgaccgcct | cccgtgcgac | 1380 |
| gtggtgaacc | tgtacggagc | gaccgaggtc | tccgtcgact | ccacgtggtg | gacggcgccc | 1440 |
| cgggacctgc | cggacgcacc | ggtgctggtc | ggccgtccca | tggccggcgc | caccgcgtac | 1500 |
| gtcctggacg | acgagatgag | gcgactggcc | ccgaacgagg | tgggcgaggt | ctatctgggc | 1560 |
| ggggccagcg | tgacccgggg | ctaccacggg | cgggcggccc | tgaccgcgca | gcgcttcctg | 1620 |
| cccgacccgt | acggacctcc | cgggagccgg | ctgtaccgca | ccggtgacct | cggccgggtc | 1680 |
| gaggacaacg | gagagctgcg | gctgctgggg | cgtatcgacc | accaggtgaa | gctgcacggc | 1740 |
| cgacggatcg | aacccggtga | gatcgaggcg | gcgatgacgg | cccatccgca | cgtctccctg | 1800 |
| gccgccgccg | tccctgcggg | cgcaggcgct | ggggcgaccc | tgaccggatt | cttcaccggc | 1860 |
| gcggaagcca | acgccgagga | gctgcgcggg | ttcctcgcac | agcggctgcc | cgccgcgctc | 1920 |
| gtcccctccc | ggctggtcgc | actggacacg | ctcccccctgt | ccccaacgg | caagatcgac | 1980 |
| cggaacgcac | tggccgacat | cgccgcgcgg | caggacctcg | ccgcggtacc | gccggcaccc | 2040 |
| gaacacaccg | accccgtcct | acgcgccgtc | ctcgacgcca | cagcggacgt | cctgggcgga | 2100 |
| acacctgtcg | ccccgcacga | gaacttcttc | gacaagggcg | gcaactccct | gcacgcgacc | 2160 |
| cggctcgtgg | ccaagctgcg | ctcggccctg | gacacggcga | tcggcgtccg | cacggtcttc | 2220 |
| gaacaccaga | ccccggccca | actggccgac | gcactgcgcg | tcacgctcga | cgacccccg | 2280 |
| gacagtggtg | cgcggggcac | cgcggaaggc | gagctgtccg | ccgcccagca | ccgtatgtgg | 2340 |
| ctgctggcga | gatctccga | gaccccgccc | gagtacgcca | tcactctcgc | cctccacctc | 2400 |
| gcgggcgccc | tggacaccga | ggcgctcggc | tgggccgtcg | acgcggtggt | gcggcggcac | 2460 |

-continued

```
gactccctgc gatcgtgctt ccccgaccgg gacggcactc ccgtgcgggc cgaggtgccg    2520
gccgaggcct tacggctgat ccatgcaccg ccggagccgg gcggcgaccc ggacgaggtg    2580
gtacggcgag tggtcgccga agagacggcc ggtctcgacc tggtggccgg gcccctgttc    2640
cggccggtac tggtgccgct cggcgccgag gagtacctgc tggtgatcgt gctccaccac    2700
atcgtggcgg acggctggtc gaccgaggtg ctgctggagg acatcgccgc gcactaccgg    2760
gcccggacgg gcggggaagc cgtacccggg cgtccggtcg tcagctaccg gcgctacgtg    2820
gacatcgagc gccgcaacga gcgcgacggc gtcaccgacc gggatctgga gtacttcacc    2880
accgagttgc acggcatccc cgaggaggtg accctgcccc tggaccggcc ccggcccgca    2940
caacgcaccg ggcgcggcgc gaccctccgg ccggcgttcg gaccgcgcgg ggccgacgcc    3000
gttcgtcggc tcgccgccgc gcaccgcaca acgccgttcg tggtcctgct cgccggtctg    3060 agcaccttg tgcaccgcgc gggcggccac gaggacgtgg tgatcggcag tgcggtcgcc    3120
gggcgcttcg acgccgagct ggacgacctc gtgggcctgt gcctcaactc ggtggcgttg    3180
cgctggccgg tcggtcccac cactgccttc gccacggtgg tggagcgcgc cgagcgaagc    3240
ctgctcgacg ccatggacca ctccgccgtg cccttcgccc gggtcgtcga aagctgggc    3300 gtgcgccgcg acgcgcgccg tacccccgtc ttccaggtca tcgctctgta cgacgacttc    3360
cccgacagcc cggacctgcc gggcctgtcc gtgcgcgccc tggagacgga cgacggcacc    3420
gcgcagtgcg acgtgctgtt caccttccgg ccgccgaccg atgacggcat gtccctgggt    3480
atcgaattca gcacggacgt ctacgaccac acgaccgtgc tgtgctgggc ggagcagttg    3540
gagacgttgc tgaccgccgc ggcggacgcc cccggcaccg aggtggcccg gctgcctctg    3600
ctgtccggat ccgcgctgga cgcgctgctc acctgggcg cgggccccgt gcggccgctg    3660
cccgacgacc tcacgctgac cgggctgttg gccgccagg tggccctggc ccgcagcgc    3720 accgccctga cctggcggga ggccaccgga acggtcgcca cgctcagcta cgcgggcttc    3780
gacgaacgct cctcccgcgt cgcccacgcc ctgcgcgagt acggcgtcgg cgccaacacg    3840
ccggtcgccc tctgcctggc ccgtggcgcc gacgtgctcc ccgccgtgta cggagtgctc    3900
aaggcgggtg gcggctatgt gccgatcgaa ccggacaacc cgcccgagcg gatcgccggg    3960
ctggtccgcg acacggcgc ccgcgtcctg ctcacccaac ggcggcagac cgcctcactg    4020
ccgaaactcc cgggcgtgac cgtcctcgtc gtcgatgacc acgaggcgct gagccgcttc    4080
ccggccacgg tccccaaacc ggtgccgcgc cccaggacc tggcgtacgt catctacacc    4140
tcgggctcca ccggccgccc caagggcgtg atggtcgaac accacagcgt ggtcaactat    4200
ctgacgactc ttcaggaaaa gttccggctc acctccgacg accggctgct gctgaagtcg    4260
ccgctctcct tcgacgtgtc cgtgcgtgag gtgttctggg cgctgagcac gggcgccacc    4320
ctcgttgtcg cggaggccgg ccggcatgcc gacccggact acctggtcga ggcgatcgaa    4380
cgggagcggg tgacggtcgt ccacttcgtg ccgagcatgc tgcacgtcct gctggagacg    4440
ctcgacgggc ccgccgcctg ccccaccctg cgccaggtca tgaccagcgg tgagaccctg    4500
cccgtgcaga ccgcacgacg ctgcctggaa ctgctcggcg cggaactgcg caacatgtac    4560
gggcccaccg agaccacggt cgagatgacc gattgcgagg tccggggccg caccgacacc    4620
gagcggctgc cgatcggccg tcccttcccg aacacccggg tgtacgtgct cgacgacgag    4680
ctgcgcctcg tgccccgcgg gacggtgggc gaactgtacg tctccggggc ccggtggcc    4740 cgtggctacc tgggccggcc ggcgctgacc gccgaccgct cctgcccgga cccctacgga    4800
```

```
ccgcccggca gccggatgta ccgcacaggc gacttgggcc ggttcaccgg agagggcctc    4860
ctggacttcc aggggcgcgg cgacttccag gtccagctgc gcggccaccg gatcgaaccg    4920
ggcgagatcg agaccgtgct gtgcgaacag ccggggtga ccgccgccgt ggccgtggtc     4980
cgcaggccgg acagccccga ggccgctcac ctcgtcgcct atgccgtacg ggccgaagag    5040
ccgcacggca cggaccaggc cctgcgcgcg aagctggccg agcggttgcc gcactacatg    5100
gtgccgacgg ccgtcgtcac gatggacgcc ctgccgctga cggtcaacgg caaactggac    5160 cgcgcgcgc tgcccgaccc ctgggaggcg cgagccaccg gagattccgg ctccgacggc     5220
gcggcggtac cggcactgaa cggccgccgg gagctggcgc tcgcggagat ctggcgcagc    5280
ctgctcagca ccgacgaggt cggcccgcag gacaacttct tcagcctggg cggccactcg    5340
ctgctcgtgg ccaccctgtc cgcccgggtc cgcgcggagc tggggtcag agcgcccctg     5400 accctgttcc tgcgccaccc ggtgctgcgc gacctggccg ccgcacttcc ggagccggac    5460
ggcggccggg cgccgcggga cgacgccggc ctgcggcagc gcggtaccga ccgcgctccg    5520
ctgtccgcgg cgcagcgccg ggtctggatc gacgaacagc tgtggcccgg taccgccgcg    5580
tacaccgtcc cggaggcgtt ttggctgcac ggcccgctcg acgaggccgc cttcgagggc    5640
gccctgcatg acctgatggc gcggcacgag gccctgcgcg tcaggatcgt gggcggtgag    5700
gacccctggc tggcggtgga cgacccgatg gccgtacggc tttcgagggc cgacatgcgg    5760
gaagacggcg agacggccgt gcagcggctc ctggagcagg cggggcgcag ggtcttcgcg    5820
ctggacgggc tctggtgga ggcgaccctg gcgaggaccg atgccgagga gtgggtgttt    5880
ctcctcaccg cgcaccacct ggtcgtcgac ggctggtcct tcgacatcct gtggcgggat    5940
ctggagatcc tgtaccgcga tcgtgtcgcg ggcggcggca tctcgcttcc gccgccgcag    6000
ctcaccttca ccgactgcac ctggtgggag agtgaacgtg tcgccgcggg cggcaaccgg    6060
ccccatctgg ccttctggcg gcaagagctg gcggggatcg cccacggggc cggaccggcg    6120
gacgccacgg acaccgaccg ttcgggcagc agccgggcag tgcggctcgg gggcgagctt    6180
tccgaccaac tgcgcttgat cgcagcagag ttgggtgtca ctccgttcgt cctcacgctc    6240
acggccttcg ccctcgccgt gaccgccgag ggctccgcgg aacaggtgat cggcgtggag    6300
gtggcgggcc gaaccgatca gcgggtcgcg gacgtggtgg gcctcttcat caatcacgtc    6360
ccgctgcgac tgcgcagaag gccggggctg acggcacgac aggccgtcgc cgccctggac    6420
gatgcctggc gcgggtgct ggagcattcc gactgtcgt tcgacacgat cgtgacggt     6480 ctgggcgagc agcgcggcgc cggccgaggt ccgggcagca catcgccttc ctcctacctg    6540
gatgcccgca ctccgccacg cctcgacggc atccgcgtca ctccgctgga gccggtgttc    6600
aacgggacgg ccaagttcgg cctgctgctg gaggtgttcg acaccccga cggactggtc     6660 ggtgtcttcg agcaccagct cgcgcggttc ggccacggcc ggatgacccg tatcaggaac    6720
cggtgggaag ccctgctgct cgggcttctc gccgacgtcc acgtcccgct ggacccgcag    6780
ggctgaaccg gcgccgcccc ggcggccggt cgccgcacga ccccggaacg caaacccccc    6840
atgcgcacgc gcaggagcga gacgaggacg aggagatgcc acccacttcg ccgccatcga    6900
cagcggcggc cacacccggc gacaccacct gccccccgcc catgtccggc aaccccgtgc    6960
tggagcacgt cagccgggcc atggccgcct atccggtcac cccggtccgc acggtccgga    7020
ccgagatcgc cggcatcccc cggaccatca ccctgaagct ggagggccac tcgccctggc    7080
gatcggtcaa gggccgcacc gcactcagtc tgatccggtc ggtggccggt gacctgaccg    7140
cccccgatgc caccgtcgtc gaatcgacct cgggcaatct cgggctggcg ctctccgcca    7200
```

-continued

```
tctgccggga cctggggctg cgtttcatcg ccgtcgtcga ccaccggcag tcccccgtca    7260
tccagcaggc catcgaggcc aacggcgggg aactggactg ggtcaggacc cccgacgacg    7320
ccacgaccca cctgcaggac cggctggccc gggtgcgcga gctggagcgg gacctgccgc    7380
acgccgtatg cccaaccag tacgagaacg acgccaactg gcgcatccac gaaacctgga     7440
ccgcgcccga gttcgacgcg caggtgacgc accgcgcaca ggccctgttc gccggggtct    7500
ccaccggggg caccctcgcc ggcctgtccc gccatttccg gcgcacccgc cccgggctgc    7560
ggatcgtcgc ggtggacgtc aggggctcga ccgtgttcgg cggggtgccc cgcccccgca    7620
ccctgaccgg aatcggcgcc ggcaggaggt ccgcgttcct cacccgggca agcaccgacg    7680
acgtgctcct ggtcgacgaa cggcaggctg tggcctgctg ccacaccctg cgggcggaca    7740
ccggcacagc ggtcggcggt tccagcggtg cggtactggc cggctgtctg gagtacctct    7800
accggcatcc cgaggtgcgt cacgcgctgt gcctctgccc ggatctcggc gaccactacg    7860
gcccgaccgt ctatcacccg gcctggctgg accggatggg cctgccctcc gaggcgcacc    7920
ggctgcgcca ccgaacggga gcggcctgcc ccggcttcga accggtcgac gacatcaccc    7980
cagcccccag cgcccgtcc gaggaggacg catcgcgatg actgagagcc ccacgacgca     8040
ccacggcgcc gcgccgccgg attcggtcgc cacgccggtc cggccgtgga gtgagtttcg    8100
gctgacgcct gcggaagccg cagccgccgc cgcgctcgcg gcccggtgcg cacagcggta    8160
cgacgagacc gacggccccg agttccttct cgacgcccc gtcatcgccc acgaactgcc     8220
caggcggctg cggacgttca tggcccgggc gcgtctcgac gcgtggccgc acgccctcgt    8280
cgtacggggc aaccccgtcg acgacgcgg gctgggttcc acgcccgtcc actggcgcac     8340
cgcccgcacc cccggctcgc gcccgctctc cttcctgctc atgctctacg cgggtctgct    8400
cggcgacgtc ttcggctggg ccacccagca ggacgggcgg gtcgtcaccg acgtcctgcc    8460
gatcaagggc ggggagcaca ccctggtcag ctccagcagc cggcaggagc tcggctggca    8520
caccgaggac gccttctcgc cgtaccgggc cgactacgtg ggtctgctct cgttgcgcaa    8580
ccccgacggg gtggcgacca cccttgccgg tgtcccactg gacgacctgg acgagcggac    8640
cctcgatgtg ctcttccagg agcgcttcct gatccggccc gacgactccc atctgcaggt    8700
gaacaactcc acggcgcaac aggggcgagt ggagttcgaa ggcatcgccc aggccgccga    8760
ccgacctgaa ccggtggcga tcctcaccgg ccaccgtgcc gcaccccacc tgcgcgtcga    8820
cggcgacttc agcgcacccg ccgaggggga cgaggaggcc gcggcggctc tcgggacact    8880
gcgcaagctg atcgacgcgt cgctgtacga gctcgtactc gaccagggcg acgtggcctt    8940
catcgacaac cgcagggccg tacacggcag gcgcgccttc cagcccccgct acgacggccg    9000 ggaccgctgg ctcaagcgca tcaacatcac ccgtgatctg caccggtcgc gcaaggcgtg    9060
ggccggcgac tcgcgggtcc tggggcagcg atgaccggcc cactcggcgc gggcccgcag    9120
gcgctgccgg cggcgcccct ggaggactgg ctgcgtgaac gctacttcca ggcgaagacc    9180
gacatcagca gcagcggcgt gcacaactac accttcgggg aactccgcgc cctcgacccc    9240
gcgctgctcg gtacgcggga gcttgaccag ctgatgttcc gtgacggtcc atcgctgggt    9300
gacgagcggc tgcgcgccgc cgtggcggcc cgggtacgcc ccggcccgg ccatgtggtg     9360 atgacgaccc acggctccag tgaggcgctg tacctcgcct ttgccgcact ggtgcgcccc    9420
ggggacgagg tcgtggtcgc cacgcccgcc taccactcgc tgtcggggct cgccaccgcg    9480
gccggcgcga gcctgcgtcc gtggccgctg cggccggaga acggcttcgc cccggacctg    9540
```

-continued

| | |
|---|---|
| gacgatctgc gggcggtgct cagcgaccgc acgcgcctgg tggtggtgaa cttcccgcac | 9600 |
| aacccgagcg gtgcctgcgt ggaccccega ggccgtacgg agctgctcga tctggtcgcg | 9660 |
| aacagtcagg ccgttctgct gtgggacggc gccttcaccg atctcgtcca cgaccacccg | 9720 |
| ccgctggccg aaccgtcgca ggacctggac cgcgtgctga gcttcggcac gctgtcgaag | 9780 |
| gcctacggcc tgccggggct gcgggtcggc tggtgtgtgg tcccgcagga cctggtttcc | 9840 |
| gagctggtgc ggatccggga ctatctgacg ctcagcctct ctccgctggt ggaacgagtc | 9900 |
| gcagccgtcg ccgtggagca cgccgacgcc ctgatcactc cccggctgac cgaggcgcgc | 9960 |
| cacaaccggc gacgggtact ggagtgggcg gcggcgagcg agggagccat cgactgcccc | 10020 |
| gttccacgcg gcggggtcac ggccttcccc cggttcaccg cccacacgga cgtcaccgac | 10080 |
| ctgtgcgagc ggctgctggc ccggcacggc gtactggtgg tccccggccg ggtcttcggg | 10140 |
| caggccgacc ggatgcgcat cggattctcc tgcccgcgcc cggagctgga acgcggtctg | 10200 |
| gccgcgatca gcgaggagct cggtacgcac gcgcgcggcc ggcgaagggg gacgggatga | 10260 |
| cctcgacgcc gtgcggcgga acagccgagc agaagtccgc gtccgccggc gaagccgccg | 10320 |
| aggagaagcc cgcgtcgctg cggcgcaacc gtgacttccg gttctggtgg ggcggcacca | 10380 |
| tgctcagcgc catcggcgac gagctcaccg ccgtcgccct gccgctgatc gtgctgctga | 10440 |
| tcaccgactc gccgctgcac gccggcctcg tcggcagcgt ggagtcgatc cctccgctgc | 10500 |
| tcctgagcct gccgctgggc atgctggtgg accgcgtctc gcggcgggcg gtgatgctcg | 10560 |
| cggcctccct gctcagcgcg gcctcgatcc ccaccgtggc catcgccttc ctgttggacg | 10620 |
| ggctgagcct gccccagttg tacgtggtcg cgttcgtcaa cagcctcgcg gcgacggcgt | 10680 |
| accgcatcgc ggacacggcg gcactgccgg gaatcaccgg cccgcacaag ctgggcgagg | 10740 |
| ccgcgagcca gagcgagacg atcttcggta cctcggctct gatcgcgccg ccgctggcgg | 10800 |
| gcctgatgtt cgagaccatg agcccgccgc caccgttcct cctggacgcg ctgtccttcg | 10860 |
| tggccgtcgc cgcggccatc ctggcgatcc ggtcgcggct cggacccgag ggcgccccgg | 10920 |
| agccactgcg ctggcgccgc gaactgaccg ccggcatgcg gatcaccgca cggctgccgc | 10980 |
| tggtgcgcgc cctgacgctg ctgacgaccc tgggcgactt cctcttcgcg gggatcgggc | 11040 |
| tgctgctcat cgtgctggcc aaagggagcg gcgcctccgg cttcgaggtg ggcgccgtct | 11100 |
| tcacggccgc cggtgtgggc agcctgctcg gcgcggccct cgctccgcgc atcgaggcgg | 11160 |
| gtctcgggct gcggaccgcc gtcgtcggca agcactggct gaccgcgctg ctcttcccee | 11220 |
| tgctgctggt cgacctgccc ggatgggga tcgggctggt gtggggactg gtcgcgctcc | 11280 |
| aggtcgccgt actgaacgtg atccagatga agtatctgat gagccaggtc cacagcgacc | 11340 |
| agctcggcag ggtgcagggc ttcatgacct tcctgtcgaa gagcagcctc cccctcggct | 11400 |
| acgccctgac cggtctcctc ctcgaccggt gggggacccg gggcaccatc gtgttcttcg | 11460 |
| aagtcgtgct gctgtgcctc gccgtgtacg ccctcctggg acgcggtctg cgcgcctccc | 11520 |
| acgtgaccag gagcgaagac gccgggagcg gcgcgcctga cgaccagcca ctgccgagcc | 11580 |
| gacgggaag cgagcgatga cggatctgga cttcaccagc tgggatctgc gcaccgaggc | 11640 |
| cgaccggcgg gcgttccccg cggactgga cggtcccgcc cctcctggaa cacggacac | 11700 |
| gaccctggtc aggatcgtgt gggagcaggt gacacgcaca ccgcacgccg aggccgtacg | 11760 |
| cgtgggtgac cgggccctga cctaccgcga gttggccgac tccgcggcca gggtggcccg | 11820 |
| ttgggcggcg gggctgcgga gcgaccggga acggagctg cgcatcggcg tggtggcaca | 11880 |
| ccggtcgctg cccgtctacc cggtgctgct cggggtgctg gccgcgggcg ggtcctatgt | 11940 |

-continued

```
gccgctggac ccggcggcac cggtgcggcg gctgcgtgag gtcgcccggc gggcggagct   12000
cgcagcggtg gtcaccgacg cggaggggtg ggccgggctc ggcctctccg acatcgccgg   12060
gctcctcgtc gaccgtgcgc tgccgttcca gcgcggcagg ctcggcggcg ggacgctcac   12120
ggagttcgaa tcgctgcccg aggccgacgg cgcgctgccc ggggccgggc gcccgggcgg   12180
accgcggccg gacgacgtgg cgtacacggt cttcacctcg ggttccaccg gcgcgcccaa   12240
gggtgtgctc gtcgagcatc gcggcgccgt caacctggca cggtgggtgg ccggcaccac   12300
ggacctcggg ccgggaagcc gggtcaccca gaacgcctcc ctgcacttcg acgcctccgt   12360
ccagcagatc ttctccgcct ggtcggccgg agcgaccctg ctgcccgtac ccgagaccgt   12420
gcgggtcgac ggcgcgcggc tgtacggctg gctcgccgaa cagggcgtga cccactggga   12480
ttccgtgccc tccctgtggg cccggtcgt ggaacactgc gccgggcgca tcgccgcggg   12540
cgagacggtc ctgcccgccc tcagggccgt actgctggcg ggcgaggtcc tgccggccgc   12600
acgggtcaac gagtggcggc cctggcagca ggggcatcgg ctgttcaaca tctacgggcc   12660
caccgaggtg accgtcgacg ccaccgcgta cgaggtgaca ggccccgtca ccggcggtgc   12720
ccctcccatc ggccgtcccc tgccggggct gcgggccctg gtcctcgacg cggacgggca   12780
cccgtgcccg ccggaggccg acggcgaact cctcctcggt ggcatcggcg tcgcccgggg   12840
ctacctcgac gatccggcac tgaccgcgca acggttcgtc gcccgcgagg gagctcgctg   12900
gtaccgcacc ggagacctcg tccggtacac cgcggaaggg gacctggtgt tctccgggcg   12960
tcgcgacgac caggtgaagg tgcacggcgt gcgcatcgaa ctggccgagg tggaacgggc   13020
gttgcacgca gacccgcggg tcgccgaggc gatcgccgtg gtgctggacg acgcacaggg   13080
ccgccatgaa ctggccgcag ccgtcaccac ccggacgccg gtcgccggtg ccgccctgcg   13140
tgcctcgctc gccgaggagc tgcccgccgc catggtcccc acgcgggtgc tcgtcgtcga   13200
cgccctgccg cgcaccgcca acggcaaggc cgaccggagg gcgggcgcgc gcatggtgcg   13260
ggacttcgcc gacccgggcg acggtggtac ccggcccgcg gccctgaccg ccaccgggcg   13320
gcggctcctg acgatctggc gccaggtgct gggcctgccg cagctcggtc cggacgacga   13380
tttcttccgc agcggcgggg actccatcgc caccctccgg gtgcgtcacg agtgcgccgg   13440
ggccgggctg cccatccagt cggtggacat gttcgcgcac cccacggtgc gacgactcgc   13500
ccgccatctg gaccgcactc cggccgagcg gcccgcgacc gcccggagcg ttcccggcat   13560
cggcgcgtcg acgctgctgc ccgcgcagcg gcggctcgcc gtggcgacgc tcctgagcga   13620
ccgcgtaccg cagttgggac tggtccagga gagccacgag tacgaggagg aactggacgc   13680
cgacgcgctg cgcaccgcgc tcgatctgct ggccgagcgg cacgaggtgc tgcgcacggg   13740
ggtggagagt cgcaccgacg gcttccgcgc caggaccgag gagcgggtga cggttccgct   13800
caccgtgcac cggtcggacg gcagcggcgc ggccgcacgg cgcgaactcg cgcgttccca   13860
cgccgacgcc gtgctgcggg aggggttcga cctgtccgcg ccgccgctgc tgaaggtcgc   13920
cgccttcgag ctgaacggg gccggttcac cctcgtgtgg acgcttcacc acgtcatctc   13980
ggacggctgg tcctgggagc tgctccagca cgagttcgag atgctgtact cgggcctccg   14040
ccaaggccgc ttccgcccgc tgcccgcgcc ggcgctcccc ctgcgcgaac tggtccaccg   14100
gctggcggag tcgccctccc cggcgccctc gccggagtgg ctcacggaac tgcgcgccgt   14160
cggccccctg cccctgccgc cgggccgcgt cggcggggac acggaccgcg cgcacgtcga   14220
ctgggccgtc acgagggaga ccgacgcggc gctgcgggcc gtggccacgg ccgccgggtg   14280
```

-continued

```
tgcgcccagt accggatatc tcctcgccta cgccgaggct ctgggccggg tgtgccgcca    14340
gcgtgccttc ccgctcggca tcgtctcctc cggccgcaac gccgacatcc cgcacatcga    14400
acgtgccgtg gcctgtctcg cccgcagtct gccggtgccg gtcgacctct cgggcaccac    14460
cggcgaacgc ctccgacgtc tgcacggtca cctggccgca gtcctggccc aggactgcgc    14520
cgaccccgac gaactgctgg ccggactggc gccggcggta cgcgatcccg ccgccgcctt    14580
cgtgttccag aactaccccg acgcaccggc cgagccggtg cccctgcgtc gcgttcccgc    14640
cgcctcctgg tggcgcgaga ccgggtccga accgctcgct ctcgtctgcc acgagggggg    14700
cgtcgagggc ttccactgcc gtctcgagta cgaccccgcc gaggtctccg ccgcctgggc    14760
ggctgtgctc gcccgtgaga tccgcagggc ccaggaccgc ctggccgcaa cggagtaggc    14820
gccgcccgcg cggtcccgat acgtccggat gcgccggacg ccccacgtcg tgatgagccc    14880
cagccccgca ggaaggacca ctgccccgtg accaccacgt cccacgcagc gaccgacccc    14940
gccctcgctc tggacacact gctgaccccc gaggagcggg cggcctggag ggctctcaac    15000
gaccaggccc gatcgtggcc cgagggcctc gccctggcgc atcggctcga agaggcggcc    15060
gcgcggcgcg ccgacgagcc cgccgtgcag gccgacgacg gcacctacac ctaccgggaa    15120
ctccacgccg aggccgaccg gatcgccgcg ctgctggcgg aacagggcgt gacggagggc    15180
agtacggtgg ccgtcgccac ggcccgcagg ctgggcgagt acgccgccct gctggccgcg    15240
ctcaagctga actgcgccta cctgccactc gcggcggacg gcccggcgcg tcggctggag    15300
ttcatgctgg cggactcggc ggccgcgcc ctggtggcgg acgcccccgc ggcggccctg    15360
ctctcggagg cggggtcgg cagcagtctc acggcacggg tggtggcggg ggcgagccgt    15420
gccgcccccg ccggctggac caccggtgaa cccgccccgc gcggccgtcg gccctcggcc    15480
gagccgtggg accggaccgc gtacgtcgtc tacacctcgg gcagcaccgg caccccgaag    15540
ggcgtgatga ccggcgagga ggccctgctg aacttctgcg cgtggtatat cgaccgccac    15600
gacgtgctcc cccacgaccg gctgtgccag accgcgccgc tgaccttcga cccctccgtg    15660
cagcaactgt tccccgcatg gctgacgggc gcgtgcctgg tggtcgtgcc cgacgaagtg    15720
cagcgcgacg gaggggagtt cctggactgg ctggccgccg agcggatcac ccacctggac    15780
atcgtgaccc cgcactgggt gcagttgctc gacgtggccg cgcggcgcgg ccgggcggcg    15840
ctccccgcgc tgcgctggat cgtcgtcggc ggggagacgt acttcttcca ccagacccac    15900
cgctggcacc gcgtcgtgga ctctccggcc cgcctcaaca ccatctacgg gcccaccgag    15960
gcgaccgtca acgccaccga gttcctcgtc gacccgggtg tgacgaagg ccaggtcccc    16020
atcggccggc cgctgcccaa ctaccgtgcg tacgtcctcg acgagacggg ggcgctgtgc    16080
ccgccgaaca tcacgggtga gctgtacctg gcgggcacgg gctgcccca gcggtactgc    16140
tccctcgaag cgaccgagcg aagcttccac gaacggacgg tggccgagga cagcaccgag    16200
aggctgtacc ggacgggcga cctggcccgg ctcgtcgagt cgacgggca gtgggcgctg    16260
gagttccagg gacgtaccga cacgcaggtg aaggtgtccg gctaccgcat cgaactggag    16320
gaggtccagg cggcgttggc cgccgtcccg ggtgtcaccg cggctgccgt cgtcctgcgc    16380
accgagccgg ccaagcagat cgtgtgcggc tacgtcgccc ccggcctgac cggggaacag    16440
gtccgtgccg agctggcgga cgcctcccg gagtacatgc tgccgcacgt gatcgcgccc    16500
ctgccggccc tgccgctgac cgccaacggc aagtcgaca aggaccggct gctcgccctg    16560
gccgccgagc ggcatgccgg cgcggcgaca ggcggcgagg agccgcgcgg ccagtggaa    16620
tcggcgatcg ccgccatctg gcggaggta ctggggtgc cccgggtcgg tgccgacgac    16680
```

```
gacttcttcg tccgcggagg gtcctcgctg ctcgccttcc gggtggtcgc gctgctgcgt    16740
gagaaggggg tggccatccg cgccgcagac ctcctgcagg cccgcacggt gcgggccctc    16800
gccgagcggg ccaccaccga cgggcagctc gccgcagccg acgggaccga cgcaccggac    16860
gacggcgcgg atgacattgc gctgctgccg gacccccggc acgagctggc ggacgacacg    16920
ggacagcacc tcgacctgcc cccggccacc tcactcgctc tgctcacagg ggacaccgag    16980
gacgtcggcg accacgcggt cctcaccctc gggctgcccc tggacatcga tcccgatgct    17040
gtgcgcgaag cactcaccga ggtcgtccga cgccacccgc tgctgcggac gaggctcgac    17100
acgagccagg cgcggctgcg gctgcgggcc ctgcacgtcg tccgcttcga cctgccggtc    17160
ctggagggga acagcccgtc cctggtcgac cgggtgcgtc cgctcctctt cggccacacc    17220
gggctgcgcc gccaactgcc cgttgccgcc gccctggtga ggctgccggg cggaacgcgg    17280
ctgctgctgg cggtgcggca tctgctggtg gacggcaacg ccctgcgccg tatctcccgt    17340
gaactcgccg ccgaactggg cctgggggcg cggcccaccc cgtcggcgcc gctcaccgag    17400
cagttggcgg agctgcgcga gcgagcccgc ggcatgcgcc ccgtacggca tctcaacgcc    17460
tacctggagg cggaacggca ggcccagcga cggctggccc ccgcctcac cgccgaacac    17520
acggtgaccg agatggcggc cggcgagctg ccggcgtcct tcctcgacgg cacccggggc    17580
gcgctggagc cgcggctgct cgcggcggca cgctcgccg tgcgccggtg gctgggcctg    17640
acggccgtac cgctgagcct gccgcggcag ggctcccccg cggagaccgt ggccaacctc    17700
tccgacgtgg tcccgctgtt gatcaccgcg gacggcgacg tgacggcga ggcgggacgg    17760
gcgctcggcg cggccaccgc cgcgtgggcc gagcacgcac ggcccgaggc ccactggtcg    17820
gcggcactgc tgatgcactg ccccgggctc gcgcaccgct ggcccggccg gcgggaggtg    17880
ctcaccagct cgttcctggt cgcggtggag ctcgcggagg cgaccaccgc cggcctcggc    17940
accgcggtac cgggcacggg agggcggatg accgaccacg acagtcccac cgccgccgac    18000
ccggcgcgct cgggatccgt ccagttcacg gtcgcggccg gttccgcggg cccttcgctg    18060
cggctcatcg gctgggacct tcccgcgcg gtcctcgaag agctcgcccc gctgtggcgt    18120
gccgcgctgg ccgatgtcgc ggatctccgg gtgagcggag gagaagcagt atgagtgagc    18180
tgaccgacac ccggtggctg cgtccgtgcg cggggcactg gcgagagggg accgggcccg    18240
tgctgctgtg cctgccccac gccggcggtg gcgctctgag ctatgcggga tgggaccgcc    18300
acccgctggg cggcttcgaa cccgtggccg tgtgccttcc cggccgcgag accgcttcg    18360
cggaggatcc cgtctccggc tgggcggcgt tggtgtccgc gatcgccgac tccctcacgc    18420
ccctggcgca ccgcccgttg gcggtgttcg gccacagcat gggtgcgctg accggctacg    18480
aactgctgcg cgagctggcg cggcgcaagc ggccggcccc cctgcttctg gccgtctccg    18540
cgcaccgggc gccgcaggag atgccgaccg cggccggacc gccccgctcc ccgcgggagc    18600
tgctcgacta cgtacgacgc ctcgacgacg gcggcacggc cgagctgctc gacgacccgg    18660
agtggcgcga tctggtgctg cggccgctcg gcgccgacct ccggctgcac gacacctacc    18720
ggtcgtccgc cgaaccccg ggacagcccc cgctggccac gcccttcgtc gtgctcacgg    18780
gcgaggacga ccccaccgtc tccgaccgca cctacgcggg ctgggctgcg cttacccacg    18840
cggtcagcgc ccgaagggtc tatccgggcg gccacttcta cctcagggag cagcgggacc    18900
ggctcctcac ggagctgggc cgggacctgg agaacgcgat gagaggagaa ctgcgatgac    18960
ggcgattccg gggagcaggt caccggcggt catggacacc ccggacgccg ctgtcgccct    19020
```

-continued

```
gctggacacc accagcacgg ccctgcggga cgtgctggac ctccatcgga tcgaccccga      19080
ggccaacttc ttctccctcg gcgggaattc gctgctcgcg gtgcgggtcg cgggacggct      19140
gagccatgcg ctgggtcaac ggatccccgc gaccgcggta ctcaaccatc cgacggcgcg      19200
gggcctggcc cgccacctgg cggagctggt gtccgaacct gcctcccccg cgtcccccgc      19260
cccgccctcc gctcccgccg atgccaccgg caccgaccgg ttcccgctct ccgccgcgca      19320
gcgacgcgtc tggctgctgc acgaggtcga tccggagcgg ctggaccatc tcgtcacggt      19380
ctccttcgag gtgaccggcg aactcgatcc cgtggtggcg cgcaccgcgt ggcaccgggt      19440
ggtcgaacgg cacgaggcgc tgcgaacccg gttcgagccc tccgcccccag ggggtgagga     19500
gccttgccag gtggtcgaga gcagccgct gaccgagttc accttcctgg acaccgtccg       19560
tttccccgag gcggtgcgcg tccggatcgt cgatgagcgc gtcgcgctcc tgcgccgcac      19620
cccgctctcc ctgcgcaccg ggccgctgtc ccggatcgcc ctgctgcgta cggctccctc      19680
gcgctaccgg ctcgaactga ttgtgcatca catcgtctgc gacggctgga gcctggcgct      19740
cctgtggcag gacttcctcg acgcataccg ccgggtcgcg gtgggcgagc cgggccccgg      19800
cccctctccc catcgcttcc gcgaccacgt ccgctgggaa cgccgcaccg agtcggcccg      19860
atggccggcg caggccgacc gggtcacccg ccgcttcgcc gaccggccgg aggagctgcc      19920
gctgcccatc gctccggctc ccgtcgacga gcacgacgac ggagacgacg tctcgctgcc      19980
cctgccggcg gggctgggca cggcgctcgc ccgagcgggt gccgagggtg gtcacacccg      20040
gctgaccctc gcgctggccg cgctcgccgt cctgctgcat cggatcagcg gttcggagga      20100
cctggtgatc gccgtaccga tggccgggcg ggtgcgcccc gaggacgagg ggaccgtggg      20160
tctcttcgtg aacacggcgc ttgccaggat ccgcctggcc ggggcccgcg acgtgcccac      20220
gctggtagcc cgcgccaggg acgaggccgc ggaggtgctg gactgccaga cgtacccctt      20280
cgaccagctc gtcagccggc tcggggtgcc ccgcgacggc acgcgcatgc cgctcgccag      20340
ggtgtcgctg gccgtccagg acttcgccga ggccccctg cccgacccgg atctcggctt       20400
cacgtgggtc gagcacgatc cggccgagcg acagagcaag ctggacctgg cgttcagcct      20460
gaccagtggc ggcgcggccg gacagccgac gctcaccgtc acgtaccggc cctcactctt      20520
ccgccgtcgg accgtggacg cctgggccga gcagtacctg atcgctctgg agaacgtcac      20580
ccgtgcggtg acgggggggtg cgtcatgagg ctggaccgac accacgagct cttccggacc     20640
tcggtgcgcg ccgtgctgga gcggctcttc ctgccggagc tggaggactg ggagaaggcg      20700
ggagagatgc ccacgcacga gctctaccgc tcactgggcg aggagggcct gctcgggctg      20760
acgctgcccg tcgacgacgg cggcctcggg ctcgatctgg gctactccca cgtatgggcg      20820
cgggaactcg gcagactccc ggcaggctcc ccggccatga gcctgtcggt gcagaccgac      20880
atcgtgctgc ccctgctcgc cgaggagggc gggacggggcg tccgtgacgc ctacctccgg      20940
tccgcggtac gcgtgagct ggtcgcggcc ctggccgcca ccgagcccgg cggcggctcg       21000
gacctggccg ccgtgcggac cacggccgta cgggacgccg acggactgcg gctgaacggc      21060
gacaaggcgt tcctcaccaa cggttccgtg gccgacttcg ccgtcgtgct ctgccatctc      21120
cttccgtccg gggcggacga gggcgggaac ccgccggacg gactcgactc gctgaccctg      21180
gtgctggtcc ccaccgggct cccggcgtg cgccaggaac ggcacaccgg caaactcggc       21240
aaccgcgcgt gcgaccacgg tcggctgtcc ttcaccgacg tacgtgtgcc ggaggagaac      21300
ctcctgggca agcccggctc cggatacgag gcgctgactc gcgtcttcac ccgcgagcgc      21360
accttcctgg ccgcggtctg cacggcacgt gccgcgacca tgctcgacag ggccaccacg      21420
```

```
tacgcgcggg gccgggccgt gctcggcagg ccgttgctcc agcaccaggc gatcgccttc    21480
cggctggccg aactcgacgc cgagctggcg ctgatcgagc agtacacgga cgcggtcttc    21540
cagcgactcc aggaagacgc cgccgctctg cggcaggcga gcatcgccaa gctccgcgcc    21600
agccggctgg agcgcgagtg cgccgatctc ctgctccaac tgcacggcgg agcgggctac    21660
ctggaaggcg ggccggtcga gcgaggctac cgcgacgccc gtgcctacgc cttggccggc    21720
ggcgcggacg aagcgctgct gcatctgatc gccggtcatc cgcggaccga cgtctgaccc    21780
gccgacgacc gcacccgcac ccgcacccga gaggactcgc accgacatga ccatccaagc    21840
cgtgcccgaa cctgccacca ggacggagca cctgctgttt ctcgaccgag ccgccgtgcg    21900
cacctgcgcc gcgggcatcg accccgtggc ggccgtggag gacgtgctgc gcgcccatgc    21960
ggcggggcac accgcgctcc ccgccgaggg ctatctgccc tgggccaact cccatggggc    22020
gtactgccgt tccatcgcga tgctcggctc ggtcggcgcc gccgaccga ccgtcccgac    22080 ggcctacggg atgaaattga tcaacgccgc cacgtccaac cctgcccagg gcagggagcg    22140
cgcgggtggg gtcagcttcc tgttcgaccc cgagaccgcg cgcccggccg tcgtggccga    22200
ggccgcctac ctgtcggcgc tgcgcaccgg cgcgtacacc atgtccagcc tgcgccacct    22260
cggtccggag cggttccagg aagtgaccct catcggctgc ggcgcccagg cgcggaccca    22320
cgccgagctg ctggcccggt acttccccga cgtccgcacg ctgcatgtgc acgacctgct    22380
gccggagcgc gcgtccgcgt tcgcctcctg ggtggagggc agcgagctgc cgttcaccgt    22440
ggtcccgcac ggccgggccg ccgaggccgc gcggcgagc acggtcgtca tcaccctgac    22500
catcaccgac accggctatc tctcccccgga ccacctgcgg ccgggcacgt tcgtcgccca    22560
cgtatccctg gacgatctgc tgcccgaggt gttcgaccgg gcgcaggcgc tgtacgtcga    22620
cgacgtcgag ctggtccgtg acaatccgcg ccgcgtcctg ggccggctgc tgggcgaggg    22680
ccgggtgctc gccccccggca ccccgaaacc cgggaccagc accatccgcg gcaccctcgg    22740
tgacgtcctc accgcggcgg tgcctgccga gcgccccggc accggggtcg tcgtcagcaa    22800
cccccttcgg atggccgtcc tcgacgtcgg tctgctggcc cgggtgtacg cccgggccgc    22860
cgccgacggc cacggcaccc gcctcgacct cctcggagca gaccggtgac cgaaccccgc    22920
ggcctgtact ccttggccga cctggacgac gcgagcgtcc agcgcatcgt ccgccggacc    22980
atcgaactcc acgccgaccg cgacgcccac accgcccgc tggccgggct cgtcgccggg    23040
ctcctcttca ccaagacctc cacccgcacc cgcacggcgt tcacctcggg cgccatccgg    23100
ctcggcgggg cgccgatcgc cttcggaccc acggatctgc agaccaacac aggggagtcc    23160
gccgccgaca ccggcaggat gctcgccggg atgctcgacc tgctcgtcgt gcgcaccgcg    23220
ggcccgatgc gtgaactgcg ggagctctcg ggtgagggcg aactccccgt ggtcaacgcg    23280
atgtcggcgg aggagcaccc cacccagggc ctggccgacc tggccacact gattcaccac    23340
ttcggcgggc tcgacggcgt ccgtgtgctg tacgtcggcg agggcaacaa caccgccgtc    23400
gcgctcgccc gggtactgtc ccggcagccc ggctgccacg ccgtcttcgc ctctccggcc    23460
ggttacaggc ttccggacgc cgtgctggcc gagaccgcgg ccatcgcgga tcggcgcggc    23520
ggctccgtca cccaggcgca cgccccgggc gacgtggtcg gcgaggtcca cgccgtgtac    23580
acctcgcgct ggcagacgac gggcagtacc aagcccgacc cgtcctggcg ggacgtcttc    23640
cggcccttcc acgtcgacgc cgcgctgatg aaccgctggc cggacgcggt gttcctgcac    23700
gatctgcccg cccaccgggg cgaagaggtc tccggcgagg tgctggacgg caagtcctcg    23760
```

```
ctggcctgga cgcaggcagg gctgaaggcc gccggcgcga tggccgtcct ggaatgggtg    23820
gtcacgacgt gaggacgcgg atcgcgctcc gtaccgagca ggtggcccg  ctctcccccg    23880 cccagtacag cctctggttc ctcgaccagc tcaccggacc ctccagcgag tacgtccagc    23940
cgtacgcgta ccggctgcgc ggaccgctgg acacctcggc gctggaggac gccctgaacg    24000
cgctggtcga gcggcatgag ccgcttcgta cgcgcgtcga ccaggtggcg ggcgagcccc    24060
ggcaggccgt ccggcgccac cacccgcgac cgctgcggcg actggatctc tcgcaggacc    24120
cggcacgggc cgggcgggag gcggcagcct tcgcgctgcg cccttcgac  ctggcgggtg    24180 aggatcccct gcgcacgctg ctcgtccggc tgggccagcg ggaccacctg ctggtctgct    24240
cactgcacca catctgctgc gacgggctgt ccctcgcggt cctcggcgag gacctcgccg    24300
cgctgtaccg ggcggcggcg cacgggcagg atgtcggaca ggcgctgccg ccgttgccgg    24360
tgcattaccg cgacaccgtc ctcgcccggg cgcggcaggc cgactgcccc gccgggcggc    24420
cggcgctggc gcgctggcgc gcacgactgg agggtgccgc gccgctgcgg ctgcccaccg    24480
accgtgcccg gcccgaagtc cgtacggcgc gcggcgaccg cgtcgaggtc gtcgtccccg    24540
ccgacgtcac ctcggcggct cgcgcggccg cggcccgtca ccgggtgacc ctctacatgg    24600
tgatgctgtc ggtgttcgcg atgctgctgc accgccgtgg cggcggccgg gacctctgcg    24660
tcggtactcc cgtgtccggc cggtccgccc ccgaggaaga ggcgctgatc ggcctgttca    24720
ccaacaccgt ggtgctccgt ctggacctct cggacgaccg ggacctggcg gaactgctgc    24780
accaggtgcg cggccgggcg ctggccgcat accaggacgg ccacgtcccc ttcgagcacg    24840
tggtggacga actgcggccg ccccgcgacc tgtcacgcac cccgtcttc  caggtgatgt    24900 tcagtttcca ggacttcgag gaggacgccc tggccctcga cgggctgcgc tgcacgccct    24960
gggagatccc ggtcggcagc agcaagttcg acctcgaact cgaactcggc cgcgagggtg    25020
accggctgcg cggcttcctg gagtacagca ccgatctgta cgaggccggc acggcccgtg    25080
ggatggcgga cgagtacctc gccctgctgc gcgaggccct gggcctcccc ggcgactctc    25140
ccggcggagc cgccgatcct gttcgatcct ccgatccttc tcccgaggag cccacacgat    25200
gaacgacacc cctgcggaca ccgcgtacca ggtcgtcctg aacgacgagg agcagtactc    25260
cgtgtggccg gtgggccggc cgctcccggc cggctggcgg gccgagggca ctgtcggtgg    25320
ccgccaggcg tgcctggacc acatcgagac ggtctggacc gacctgcgtc cgctcagcgc    25380
ccgcgcatga ccaccatgcc cacgaccggc acggccgccg accggagcac cgacaccgtg    25440
cccgcactgc tcgccgaggt ggcccgccgc atgcccggcg ccccgcgct  catcaccccg    25500 gaccggaccc tcacccacga cgaactcgac gacctcaccg cgaggttggc cggcctgctg    25560
cgccggcacg gcatcggcag ggggcagcgg atcgccgtgc tcgccgaccg tacctggcaa    25620
ggggtctgct gcccgctggc ggtgctgcgg gcaggcgccg cctatgtgcc gctcgacccg    25680
tccgatccgg aggaccgcct gcgcgaggtg gtcgcgctca ccggtgcgcg ggccgtcctc    25740
ggccgggccg agtcgctcgg cgagttgccc ggcctcggca tccccgtgat ccccgccgaa    25800
ccgcccggcg acctcgcggg cggggccccg ccggccacgc gggccgatgc cgagccgccg    25860
ttgccggacg acctcgcgta cgtcatgctc acctccggca ccaccggcac tcccaaggcg    25920
gtcctggtgc cgcaccgtgc cgtgacccgc ccgccaggt  ctctcgtccc gctgttcggc    25980
gtcacatcca ccgaccgggt tctgcactgg acttcgctga tctgggacac cagcggcgag    26040
gagatctatc cggctctcct cggcggtgcc gccctggtgg tcgacggacg ggtcgagact    26100
cgctccgtac cggccctgct cgcggcggtc cgcgagcacc gcgtcacggt cgtcgacctg    26160
```

```
ccgacggcga tgtggaacga gctcgcgcac tatctggccc tgggcggcga ggagttgccg  26220
cccgcgctcc ggctggtcgt catcggcggg gaggcggccc acgcccggac cgtacggctg  26280
tggaacgaac gcgtcccgga ccgggttcgc ctgctcaaca cctacggaca gaccgagacc  26340
gtgatggtga cccacgcggc ggagttggga ggtccggcgg gccgggcgct gcgggacggc  26400
gatcccgtgc ccatcggccg tccgttgccc cacatccgcc aggtcctggt cccctcggat  26460
gacgggccgg atgagctgtg gaccggcggg cccggcctcg cctggggata cgccgaccgt  26520
cccgccctca ccgcggcggc cttcggaccc gcccccggcg ccggcggacg gttctaccgc  26580
accggtgacc tggtgcgaac cctgcccgac ggttcgctcg tccacgcggg ccgcgccgac  26640
cgccggctca aggtgcgtgg ggttcgtgtc gaacccgccg aggtggagcg ggcgatgacg  26700
acctgtccgg gagtcgtggc cgccgccgtc ttccccgtgg gggacgaccc ggaacacctg  26760
cgcctgtacg gggcgttcgt cccgtcgaag agcggacccg ccaccgagcg ggaggtggcg  26820
gagcactgtg cgcggcggct accgcgctcc ctgctgccgc accgtatcgc cgtggtgacc  26880
gcgctgcccc tgctgcgcac gggcaaggtc gaccgggcgg cgctccaggc tctcttcacc  26940
gacgccacca cgccctccga aggggcgtcg gccgggtccg cgtccgggcc gtcgctcacc  27000
gcgcgactcg tggagctctg cggccgggca ctgggcgctc cgtgcggcgc cggcgaatcc  27060
ctcttcgcac ggggcggtga ctccctgacc gtgacccgcc tcatctcgct cgtccatcgg  27120
gaactggaga ccgatctgac gtttcaggac gtgttcgacc acccgacccc gcaagaactg  27180
gcgcagctag tcgaagtctc cggacccttc cgaggagagc cccagtgaca aggccgaccg  27240
cccctccccc gcccgagccg gcatcctgcc cccagccgta cgactaccgc cgccgggaac  27300
tcgtggaacc tgactggcgc agactgcccg gctggcatga cgtcaccgcg gcccagtggc  27360
acgacgtcca gtggcaacgg gcgcactgcg tcaagaacgc ccgccagtta cgggccgtgg  27420
tcggcgacgg actcgacgac aagttctacg acgacctcac ggaggaccag gagcacatgg  27480
ccaccatggc catgctgatc accccgcaga tgctcaacac catcgcgccg gagacccccg  27540
ccgactccga cggttaccac gacgccttct acgccgaccc cgtacgccgg tacatggtcc  27600
cggtccgttc cgaccgcgac ctccggtggc cgagtcaccc gttgtcgtcc cggggactccc  27660 tgcacgaggc ggagatgtgg gtggtcgagg gactgactcg ccgctacccg acgaaggtgc  27720
tcgccgaact ggtcgccacc tgcccgcagt actgcgggca ttgcacgcgg atggatctcg  27780
tcggcggctc caccccccagt gtggacaaac agcggctgac gctgcgcccc gccgaccggc  27840
aggaggcgat cctcgaccac ctgcgccgca caccgggcgt ccgggacgtg gtggtctccg  27900
gcggcgacgt ggccaacgtg ccctggccac ggctggagtc cttcctgctg cgcctgctgg  27960
agatcgactc cgtccgggac atcaggctgg ccagcaaggc gctggtgggc ctgccccagc  28020
actggctcca gccgcaggtc gtgtcaggcc tggagaacgt cgccggtgtc gccgcccggc  28080
gcggcgtcca tctggccgtc cacacccacg ccaatcacgt ccagtcggtg acgccgctgg  28140
tggcggaggg ggcccgagcc ctgctcgacg ccggagtccg cgacgtgcgc aaccagggcg  28200
tgctgatgcg cggggtcaac gacagcacgg cggccctgct cgacctgtgc ttcgccctgc  28260
aggacgaggc gggcatcctc ccgtactact tctacatgtg cgacatggtg cccggggcgg  28320
agcactggcg gacatcactc gccgaggccc aggacctcca gcacgcgatc atgggctatc  28380 tgccccggcta cgccactccg cgcatcgtct gcgacgtgcc gtacgtcggc aagaggtggg  28440
tgcaccaggc cgtcgagtac gaccgggagc gcggcatctc gtactggacg aagaactacc  28500
```

-continued

```
gcaccgcgat cgagctcgac gacccggacg cgctgacccg ccgctacccc ttccacgatc   28560
cgctgtccac gctgcccgag agcgggtggc gctggtggga acggcaggtc gcggcgcgtg   28620
agggccaggc atgcgcctga ccccccggcc gggtaggtgc gcggcccagc ggcccctacc   28680
ggtagccgct gaggccgtcg gcgagttcct cctcgtcgcc gtcgcgctgc gcgtagaggg   28740
cctgctggag tgcgaaggtg cctcggatcc ccgagatccg ctcggccgtt ccgttgtcgg   28800
cccagccgcc gagcgcgagc actcggccca gcagttcctc gccgtagctc gccccgatgg   28860
cggccaggtc ctcagccggg tcgccgatgc cgacctcgtc ccagtcgacg acgccgctca   28920
tgcgcggcac tccgtccacc gtctcccaca ggacgttctc gccgccgagg tcaccgtgga   28980
ccaccgcgga ggtgagatgg ggcagggcgt cgagcgcggc gagctcgcgc tcggcacgct   29040
cccggccgcc gtcggacatc agcgggaaca gttcggtacg caccccgtg gcgaactcct    29100 gccactcgtt cgcgggagcc tccggcagcg cggcgcgcac cttctcctcg tcgcccgccg   29160
ccgcgagccc ggacagcagg gtcgcgtact gtcgggcgac ggcctccgcc acctccgggc   29220
tggtgagcac atcgtcctcc aacggtgctc cgggaatgcg gctcagcacc aggtacggcg   29280
gctcgtccgt gccctgggcg ccgccctcgg acagcggctg cggcgtgcga aacccgaggt   29340
cgatcccggc aagagcgcgc aggacgtccg ccctgccggg cagacggtcg gcggccgccc   29400
gggtgcgggc gaagcagacc acccggtgcg atccgatcac cacatggtgg aactgcccct   29460
cgtggacggc gagtccgccc acggtgtccc cgggcaggag ccggctcagc agatcgcggt   29520
gcgtctcaat gattctcatg gtgggcgaag tctccacttc tcagatgtgc gccggctgac   29580
gcctggcgca tgccgacgtg tcgagtcatc agaaactggg gtgtgacgat ggatccggtc   29640
gagtacgaga tgctgcggca catgtggttc ccggtcgccc gggtcgccga cctgaagaac   29700
ggcgtcgcga gcggcagcat cctcggcgag gaactcgtgg tctacgggga cgagggctcc   29760
gtcaccgtcg cgcagggctt ctgcccgcac cggggcgtgg ccctacgact cgggcagctg   29820
cgcgacggag cactggaatg cccctaccac ggttggttgt tcgaaacggg cagcgggcgg   29880
tgcacgcgca ttccgtcgct cccgccgggc cggggcaggc cgcacacggc gctgcgcacc   29940
catcccgccg aggtcgccta cggcctggtg tggagttgtc tgggcgatcc gttcctgcct   30000
ctgccgcggt tgcccgagta cgtcgacgac agctggcgac tcggcgcggg cgagccgtac   30060
acgctgaact gcggtatgcg gctgctgacc gagaacttcc gggacaaggc ccacttcccc   30120
ttcgtccacg cggactcgat gggccatgtg gacaaggtgg tgcagcccta tcgcatcagc   30180
agagacggct ggcggctcgg ctggtcctcc tcgctgggct ccgaaggggt gcccgaggac   30240
ctcgcgcagg agttgagcca tcggctggac taccacatca ccatgccggt gttcgcctcg   30300
atctgcgtct cctcgccgtc cggtgggcgc cggctggtcg cgcaggtggc cactcccgtc   30360
tcggcggacg gcaaggcggt acggcagttc tggctggcgg gcacggacgc cgagtcgacc   30420
gcacagggag ccgtcctggc cgacgtactc ggcttcgaac ggcaggtctt cgaggaggac   30480
caccccatcg tggagaacca gtggcccgtc gaggcgcctc tggacgttca ctctcaggtg   30540
cacacacccg cggaccggtt cagcatcacc taccggaagg tgtacgggga actgctgatg   30600
aatttcaagg aaagccggtg acgtgggcag tcgcgacatc gaacccgctc cgggaggtct   30660
caggtctgcg gaaggagaga cggggagccg aggccgagcc gccacaccag ttgggcggcg   30720
tggacccggt cgcggagttc gagcttcgcg aggacgcgtg agacatggct cttgaccgtg   30780
gcctcgctga cccggagtgt gcgcgcgatc tcccggttgc tccgtccgtc tccgacgagg   30840
aggagtacct gctgctcccg ttcgctgagc agctccagtt ccgccggtct gtccgtgcgg   30900
```

```
cggggcacca gatggaagtt cctgacgaga cgtcgggtga catgggtcgg caggaagcct    30960
ccaccggcag cgacggcctg gatcgccgcg tcgaagtcct cgcgcggaga gctgagcgga    31020
acgtagccgt gcaccccggc cgcgagcgcc gccgacagca gttcgtcggt gtcccgttcg    31080
gccgccatga cggtgttccc cgagacagcc tcgggcagcc ggctcagcgc agggaggccg    31140
tcggggagca ccaggaggt tccggcgacg acgacatccg cgacaaccg ggtcgactgg     31200
tgaaccaact cctttcggtc caccgccgtg ccgaccacct cggcattggc gatctccgag    31260
aggaggacga caaccccctc ccgatagaca tccctgtcct ccgccaacag gatccggacc    31320
cgggcgcctg gctcatccgc cggggggcgca ccgcacggtc gatgcggcac gagccaccct   31380
gatgaggtct gccccatatt tccccctgc tcgctttaca cacccgtaat cggcgccggg     31440
ccacgagcaa tagtagatct aaaacttctt gggcatcgct ttaccgctaa tcgattgacc    31500
gaaaaacagt ttcagtcaaa caatttggc caccgaggat cattcgcagg gaaggcactc     31560
cacggcgctc aggcagttca gacgcgacat ggagagcggc agggacaccc atttcaagtc    31620
ttccgaacac ggctggcttg agtcacttga cagaggcatc cggcatgccg tatgcgccat    31680
tacttgcctt attaatttcc ctgacactgg ccagaaaatg ccagatatga atttaacacc    31740
actggaggtt cgtgactatg aaatgcaggg tactggggag cgcccttac acgcggcaag     31800
ccttggcggg cgccgcactg ctcatcgccg gcaccgtgat ggggcccgcc gcagcgtcga    31860
gcggagacga acgggacacc tcgcgggcac gcaacgtgat cctgctggtc ggtgacggca    31920
tgggcgactc cgagatcacc ctcgcgcgca actacaccgt cggcgcgggc gggaggctcc    31980
acatggacgg tttccccatg accgggtcgt acaccaccta ctcggtggac cgcgacggac    32040
gtcccaacta cgtcaccgac tccgccgcca gcgccacagc ctgggccacc ggccacaaga    32100
cggtgaacga ccggatctcc aagacggccg acaccgaccg cgccgtgccc acgatcctgg    32160
agctcgcccg gcaaggcgga ctcgccaccg gcagcgtcac cagcgccgag ctgacggacg    32220
ccaccccgc cgccctcacc tcgcacgtca ccgaccgcag ttgccagggc ccagccgaca    32280
tggagcggtg cccgacggac acgcgggcgg cgggcggccc gggctccatc gccgagcaga    32340
cggtcgccca ccgcgtcgac gtcctcctcg gcggtggcag gcaacgcttc gaccagacca    32400
tcacccaggg tccggagcgt ggctccacgg tgctgcagcg tgcgcgtcag cacggctatc    32460
gcgtggtgac ggacgccagg ggcctggacg ccgtccgccc cggacgcccg gttctgggcc    32520
ttttcgcacc ggaggagctg ccggtcgcct ggaccggaac gccggccgcg gccggcggca    32580
ccgcaccaca gcgctgcgtg accgaccgcg aaccctccga cggcatcccg agtctggagg    32640
tgctgacgcg caaggccatc gcgctgctgg atgcccgagc acgccagaag ggcgcgggga    32700
aggggttctt ccttcaggtc gaaggcgccg ccatcgacaa gcagaatcac gatgccgacc    32760
cctgcggcca gatcggtgag accgtcgcct tcgaccgagc cgtcaaagcc gccagggagt    32820
acgccgcacg gcaccctgac accctcgtca tcaccaccgc cgaccacggg cacagcagtc    32880
agatcgtgcc catggcggcc aggcccgcag gactctccgc gacgctgatc acggacgagg    32940
gcgcccgat gaaggtcagc tacgccacgc acgcgggcga ggagggacag gagcacagcg    33000
gcgtacaggt acgcatcgcg gccgaggggc ccgaggcgca cagagtgctc ggcaccacgg    33060
accagaccca actgttcacc actctccgca tcggtctcaa cctgcggtga cctgcaacag    33120
cccctcggcg gtcactcggc gcgcctgttg caggaagggc tttcgtctcg tcggtactgg    33180
tggcgtcggc tttccccgga gagaagccgg agattatccg cgccgctggg gagcgcctgg    33240
```

```
ggagaatcgg ccagatagcg cgagacgagc ctgaaacccg tcctgccgta agcgagggcg    33300
tggagccgcc catcgccggt taaccgaacc ggcgtatccg cagatgaatg ttgtccaccg    33360
tccgccccga gcacccgtgc gaatcagtcc acccgagggg actcacttct tccggcgcac    33420
gcggaatcca gccgaatctc caccccgcgg actgcgtgcg cctgtcgccg accgctttcc    33480
gctatatccc tctggcgctc tccaccgccg gatttcccac cggctcccaa aactgatcga    33540
gggccggttt cggattgctc cgaaaccggc cctcgatcaa cgactgtctc cagtcgggac    33600
gacaggattt gaacctgcga ccccttgacc cccagtcaag tgcgctacca agctgcgcca    33660
cgtcccgccg cgttccctcc cggtctcccg ggtggccgcg caggacaaac attacctcac    33720
tcggaggacc ggatcgacgc acgtgcctgc tgggcgcggg cggccaggcc ctcggcaccg    33780
caggtcatcg cctgcttctg cgcgcgggcc agctcccggt gcgacccgat cgcagcgccg    33840
tactcgaacc gggcgagggc gtgttcgtag ccggaggtcg atttctccag gtggccgacc    33900
gcttcggcga gcagttccgc ggaacgctcc ggcggggcga acagagcgac acagcgcagg    33960
gcctcgccca tggcggtggg tgtgccgagc cgctcggcgt gcacacggtt gcgggcggcg    34020
aggtgagcgg cgcgggccgg gtcctcgtcg accagggccc gagcgaggtc ggcggcccag    34080
ggagcccaga tgccgttgaa gcgttcccgg gcctccaggg cggcgcccgc cgcttcgagt    34140
tcggcgatcg cctccttcgt acgccccccg gccagcagca gacggccccg gatgcacggt    34200
ccgtccggca gcaccatggc gctggggtag ggcggtccga agtggtagcg gtcggcgatg    34260
ctgcgtgctt cctcggtccg gccgcgggcc agcagggtgt cgatgagcag acacgtcgca    34320
tcccagtgca cgggcagccc ggagccgacg cggtcggcga ggcgcagtcc ctcgcgcagg    34380
aagccctcgg cctccgcgag gcggccgcga cggcggtgga ccatgccgag cagggtgtgg    34440
gcgaacgcca ggtgggcccc gctccagccg gagatctcga aggcccggac ggcttcgccg    34500
aagaggctct cggcccggtc cagctggtcc acgaagctgt acgtgatgcc gaccatggtg    34560
gggagctcga agccccactc ggtgtcggtc cagccgagcc cgcgcgccgg gctgccgtcg    34620
accagggcgc gttcgcagag gtccacgatc agctgggcgt tctcgccgcg cagcatgccg    34680
tcgaaggcgc gcagggtgag cagtgcccgc tcggcgttgt cacggcccct gaggtggtcg    34740
gcgttgcggg tgagccggcg ggaacgggtc ggcccgtcgt cctcgacggc ctgcatgccc    34800
tcccacatga agtgcgcggc ctggagccgc atcagtccgg ggcccggatc ggtccgcgcg    34860
gcctcggcgg ccagcgcgag cgccgcttcc ttgagctggt tgttgtgggc gagcgcggcg    34920
gcgagccgga acgtggcgtc gacccgcagt ccgtcgtcga gccccggcat gtccagcgcg    34980
gcgcgcaggt gctggaccgt ggtgggcggt gagctgagca gggtcgcgca gcccagctcg    35040
tacagcagag ccgcccggtc cttggggcgc ggcggttcct ccagcgcccg ttccaggcag    35100
cgccgggccg cttcgggcgc accgacggcg aggtgctgcc gggcggcttc ccgcagttgg    35160
gcgaccagct cctgatcgtc gtccgggtgg acctccagca gatgtctgga ggccgcggca    35220
ggcccgagcc cggcccgggt gatcgcccag gcggctcgcc cgtgcatggc ggtgcgggtg    35280
gccgacggga tcgagcggta gaccgcggac gcgatcagcg ggtggacgaa ctccagcggg    35340
tcgaatccgc tgacgatacg ggcgtcgcgc agccgggccg tgcagtcggc ggcctccgcc    35400
gggctcatgc cggcgagggt ggcggccagt tcctgggaga tgtcggtgcc gagcacggca    35460
gccgcccagg cgaaccggtt ggcgttcgta ccgagccgct ccagccgggc gacgagcccg    35520 ctgcccggg cggaggcgcc gagcgcacgg agttcacccg cggactcctc cacgggcggc    35580
agttcgtggt cctggacctt ggcgaccagt tcgaccgcct cgtacgggtt gccgccggtc    35640
```

```
accgcccaca cctcacggca gaacgggtcg tcggcgtgct cgccgagcgc cgaccggacc   35700
agtacggcgg tggcgtccgg tgtcagggcg cgcagcgcga cgcgggtcac cttctcctgg   35760
ccgtgggagt cacgctcggc cgcccggtcc gcgacgtagc cggcgttgcg ttcggccatc   35820
tcctgcggac ggtgcgcctg caccaccagg accggcagtt caccgaggcg ggcggtgaac   35880
gaggccagcc aggcgaggga ttcaccgtcc gcccagtgcg cgtcgtccac gatgagcagc   35940
aacgggcggt ggctgagccg ggaggcgagc cggccgacga cgtagtccag gccgtcgcgc   36000
acaccttgcg ggtcgggctg cggtccgctc ggctcggcca gcccgagggc cggggcgatg   36060
atctcgaacc agtcgccgaa cagggcccgg gtctcgtccg gcgggaactg gtcgagggcg   36120
ggctgcagca actggcgtac gacgtggaac ggtacggagg tgacggtctc gcctccccgg   36180
ccggaccaga cggtgcagcg gtcggcggcc atcgcctgga tctcgtcgag cagcgcggtc   36240
ttgccgatcc ctccctctcc gctgaagcca ggaaccctcc ggcggcctgc gcgccgcaca   36300
gggcgtccag cgcctcggca gcgacggcga gttccggttc acgttcgtac aacggccggg   36360
acggcttcat gcccaccctt cccacagagg ctgtgttctc g                      36401

<210> SEQ ID NO 2
<211> LENGTH: 2123
<212> TYPE: PRT
<213> ORGANISM: Streptomyces sp.

<400> SEQUENCE: 2

Met Glu Ala Arg Asp Asp Ala His His Leu Leu Ala Leu Thr Ala Ser
1               5                   10                  15

Asn Ala Ala Ala Ser Asn Gly Pro Gly Gly Arg Asp Ala Thr Leu His
            20                  25                  30

Glu Leu Val Gly Ala Gln Ala Ala Thr Pro Gly Ala Thr Ala Val
        35                  40                  45

Val His Asp Asp Gly Leu Leu Thr Tyr Ala Glu Leu Asp Glu Arg Ser
    50                  55                  60

Thr Arg Leu Ala His Arg Leu Arg Ala Leu Gly Val Arg Ala Glu Thr
65                  70                  75                  80

Pro Val Gly Val Met Leu Glu Arg Asp Pro Glu Leu Val Val Ala Leu
                85                  90                  95

Leu Gly Val Leu Lys Ala Gly Gly Ala Phe Val Pro Val Asp Pro Thr
            100                 105                 110

Tyr Pro Ala Ala Arg Ile Arg His Met Leu Asp Asp Ser Gly Ala Arg
        115                 120                 125

Ala Val Leu Leu Arg Gln Glu Leu Arg Asp Arg Leu Pro Glu Asp Leu
    130                 135                 140

Arg Asp Gly Thr Gly Gln Val Ala Val Val Pro Val Gly Ala Glu Ser
145                 150                 155                 160

Gly Ala Gly Thr Ser Thr Arg Arg Pro Val Thr Pro Val Glu Gln Glu
                165                 170                 175

Pro Arg Pro Glu Arg Leu Ala Tyr Ile Val Tyr Thr Ser Gly Ser Thr
            180                 185                 190

Gly Leu Pro Lys Gly Val Met Val Glu His Arg Gly Ile Val Ser Tyr
        195                 200                 205

Leu Leu Gly Met Leu Glu His Phe Pro Met Gly Pro Arg Asp Arg Met
    210                 215                 220

Leu Gln Val Thr Ser Leu Ser Phe Asp Val Ser Val Tyr Glu Ile Phe
225                 230                 235                 240
```

-continued

```
Leu Pro Leu Leu Thr Gly Gly Ala Thr Val Leu Pro Arg Ser Gly Ser
            245                 250                 255

His Thr Asp Ala Ala Tyr Leu Ser Gly Leu Ile Ala Glu His Gly Val
        260                 265                 270

Thr Ser Phe His Met Val Pro Ser Leu Leu Arg Thr Phe Val Asp Gly
    275                 280                 285

Leu Asp Pro Arg Gln Cys Ala Gly Leu Arg Arg Ile Phe Val Ser Gly
290                 295                 300

Glu Ala Leu Asp Thr Thr Leu Val Val Asp Val His Asp Arg Leu Pro
305                 310                 315                 320

Cys Asp Val Val Asn Leu Tyr Gly Ala Thr Glu Val Ser Val Asp Ser
                325                 330                 335

Thr Trp Trp Thr Ala Pro Arg Asp Leu Pro Asp Ala Pro Val Leu Val
            340                 345                 350

Gly Arg Pro Met Ala Gly Ala Thr Ala Tyr Val Leu Asp Asp Glu Met
        355                 360                 365

Arg Arg Leu Ala Pro Asn Glu Val Gly Glu Val Tyr Leu Gly Gly Ala
370                 375                 380

Ser Val Thr Arg Gly Tyr His Gly Arg Ala Ala Leu Thr Ala Gln Arg
385                 390                 395                 400

Phe Leu Pro Asp Pro Tyr Gly Pro Pro Gly Ser Arg Leu Tyr Arg Thr
                405                 410                 415

Gly Asp Leu Gly Arg Val Glu Asp Asn Gly Glu Leu Arg Leu Leu Gly
            420                 425                 430

Arg Ile Asp His Gln Val Lys Leu His Gly Arg Ile Glu Pro Gly
        435                 440                 445

Glu Ile Glu Ala Ala Met Thr Ala His Pro His Val Ser Leu Ala Ala
    450                 455                 460

Ala Val Pro Ala Gly Ala Gly Ala Gly Thr Leu Thr Gly Phe Phe
465                 470                 475                 480

Thr Gly Ala Glu Ala Asp Ala Glu Glu Leu Arg Gly Phe Leu Ala Gln
                485                 490                 495

Arg Leu Pro Ala Ala Leu Val Pro Ser Arg Leu Val Ala Leu Asp Thr
            500                 505                 510

Leu Pro Leu Ser Pro Asn Gly Lys Ile Asp Arg Asn Ala Leu Ala Asp
        515                 520                 525

Ile Ala Ala Arg Gln Asp Leu Ala Ala Val Pro Pro Ala Pro Glu His
    530                 535                 540

Thr Asp Pro Val Leu Arg Ala Val Leu Asp Ala Thr Ala Asp Val Leu
545                 550                 555                 560

Gly Gly Thr Pro Val Ala Pro His Glu Asn Phe Asp Lys Gly Gly
                565                 570                 575

Asn Ser Leu His Ala Thr Arg Leu Val Ala Lys Leu Arg Ser Ala Leu
            580                 585                 590

Asp Thr Ala Ile Gly Val Arg Thr Val Phe Glu His Gln Thr Pro Ala
        595                 600                 605

Gln Leu Ala Asp Ala Leu Arg Val Thr Leu Asp Asp Ala Pro Asp Ser
    610                 615                 620

Gly Ala Arg Gly Thr Ala Glu Gly Glu Leu Ser Ala Ala Gln His Arg
625                 630                 635                 640

Met Trp Leu Leu Ala Gln Ile Ser Glu Thr Pro Ala Glu Tyr Ala Ile
                645                 650                 655
```

```
Thr Leu Ala Leu His Leu Ala Gly Ala Leu Asp Thr Glu Ala Leu Gly
        660                 665                 670

Trp Ala Val Asp Ala Val Val Arg Arg His Asp Ser Leu Arg Ser Cys
        675                 680                 685

Phe Pro Asp Arg Asp Gly Thr Pro Val Arg Ala Glu Val Pro Ala Glu
        690                 695                 700

Ala Leu Arg Leu Ile His Ala Pro Pro Glu Pro Gly Gly Asp Pro Asp
705                 710                 715                 720

Glu Val Val Arg Arg Val Val Ala Glu Thr Ala Gly Leu Asp Leu
                725                 730                 735

Val Ala Gly Pro Leu Phe Arg Pro Val Leu Val Pro Leu Gly Ala Glu
        740                 745                 750

Glu Tyr Leu Leu Val Ile Val Leu His His Ile Val Ala Asp Gly Trp
        755                 760                 765

Ser Thr Glu Val Leu Leu Glu Asp Ile Ala Ala His Tyr Arg Ala Arg
        770                 775                 780

Thr Gly Gly Glu Ala Val Pro Gly Arg Pro Val Val Ser Tyr Arg Arg
785                 790                 795                 800

Tyr Val Asp Ile Glu Arg Arg Asn Glu Arg Asp Gly Val Thr Asp Arg
                805                 810                 815

Asp Leu Glu Tyr Phe Thr Thr Glu Leu His Gly Ile Pro Glu Glu Val
        820                 825                 830

Thr Leu Pro Leu Asp Arg Pro Arg Pro Ala Gln Arg Thr Gly Arg Gly
        835                 840                 845

Ala Thr Leu Arg Pro Ala Phe Gly Pro Arg Gly Ala Asp Ala Val Arg
        850                 855                 860

Arg Leu Ala Ala Ala His Arg Thr Thr Pro Phe Val Val Leu Leu Ala
865                 870                 875                 880

Gly Leu Ser Thr Leu Val His Arg Ala Gly Gly His Glu Asp Val Val
                885                 890                 895

Ile Gly Ser Ala Val Ala Gly Arg Phe Asp Ala Glu Leu Asp Asp Leu
        900                 905                 910

Val Gly Leu Cys Leu Asn Ser Val Ala Leu Arg Trp Pro Val Gly Pro
        915                 920                 925

Thr Thr Ala Phe Ala Thr Val Val Glu Arg Ala Glu Arg Ser Leu Leu
        930                 935                 940

Asp Ala Met Asp His Ser Ala Val Pro Phe Ala Arg Val Val Glu Lys
945                 950                 955                 960

Leu Gly Val Arg Arg Asp Ala Arg Arg Thr Pro Val Phe Gln Val Ile
                965                 970                 975

Ala Leu Tyr Asp Asp Phe Pro Asp Ser Pro Asp Leu Pro Gly Leu Ser
        980                 985                 990

Val Arg Ala Leu Glu Thr Asp Asp Gly Thr Ala Gln Cys Asp Val Leu
        995                 1000                1005

Phe Thr Phe Arg Pro Pro Thr Asp Asp Gly Met Ser Leu Gly Ile
        1010                1015                1020

Glu Phe Ser Thr Asp Val Tyr Asp His Thr Thr Val Leu Cys Trp
        1025                1030                1035

Ala Glu Gln Leu Glu Thr Leu Leu Thr Ala Ala Ala Asp Ala Pro
        1040                1045                1050

Gly Thr Glu Val Ala Arg Leu Pro Leu Leu Ser Gly Ser Ala Leu
        1055                1060                1065

Asp Ala Leu Leu Thr Leu Gly Ala Gly Pro Val Arg Pro Leu Pro
```

-continued

```
        1070            1075            1080
Asp Asp Leu Thr Leu Thr Gly Leu Leu Ala Arg Gln Val Ala Leu
        1085            1090            1095
Ala Pro Gln Arg Thr Ala Leu Thr Trp Arg Glu Ala Thr Gly Thr
        1100            1105            1110
Val Ala Thr Leu Ser Tyr Ala Gly Phe Asp Glu Arg Ser Ser Arg
        1115            1120            1125
Val Ala His Ala Leu Arg Glu Tyr Gly Val Gly Ala Asn Thr Pro
        1130            1135            1140
Val Ala Leu Cys Leu Ala Arg Gly Ala Asp Val Leu Pro Ala Val
        1145            1150            1155
Tyr Gly Val Leu Lys Ala Gly Gly Gly Tyr Val Pro Ile Glu Pro
        1160            1165            1170
Asp Asn Pro Pro Glu Arg Ile Ala Gly Leu Val Arg Asp Ser Gly
        1175            1180            1185
Ala Arg Val Leu Leu Thr Gln Arg Arg Gln Thr Ala Ser Leu Pro
        1190            1195            1200
Lys Leu Pro Gly Val Thr Val Leu Val Val Asp Asp His Glu Ala
        1205            1210            1215
Leu Ser Arg Phe Pro Ala Thr Val Pro Lys Pro Val Pro Arg Pro
        1220            1225            1230
Gln Asp Leu Ala Tyr Val Ile Tyr Thr Ser Gly Ser Thr Gly Arg
        1235            1240            1245
Pro Lys Gly Val Met Val Glu His His Ser Val Val Asn Tyr Leu
        1250            1255            1260
Thr Thr Leu Gln Glu Lys Phe Arg Leu Thr Ser Asp Asp Arg Leu
        1265            1270            1275
Leu Leu Lys Ser Pro Leu Ser Phe Asp Val Ser Val Arg Glu Val
        1280            1285            1290
Phe Trp Ala Leu Ser Thr Gly Ala Thr Leu Val Val Ala Glu Ala
        1295            1300            1305
Gly Arg His Ala Asp Pro Asp Tyr Leu Val Glu Ala Ile Glu Arg
        1310            1315            1320
Glu Arg Val Thr Val Val His Phe Val Pro Ser Met Leu His Val
        1325            1330            1335
Leu Leu Glu Thr Leu Asp Gly Pro Gly Arg Cys Pro Thr Leu Arg
        1340            1345            1350
Gln Val Met Thr Ser Gly Glu Thr Leu Pro Val Gln Thr Ala Arg
        1355            1360            1365
Arg Cys Leu Glu Leu Leu Gly Ala Glu Leu Arg Asn Met Tyr Gly
        1370            1375            1380
Pro Thr Glu Thr Thr Val Glu Met Thr Asp Cys Glu Val Arg Gly
        1385            1390            1395
Arg Thr Asp Thr Glu Arg Leu Pro Ile Gly Arg Pro Phe Pro Asn
        1400            1405            1410
Thr Arg Val Tyr Val Leu Asp Asp Glu Leu Arg Leu Val Pro Arg
        1415            1420            1425
Gly Thr Val Gly Glu Leu Tyr Val Ser Gly Ala Pro Val Ala Arg
        1430            1435            1440
Gly Tyr Leu Gly Arg Pro Ala Leu Thr Ala Asp Arg Phe Leu Pro
        1445            1450            1455
Asp Pro Tyr Gly Pro Pro Gly Ser Arg Met Tyr Arg Thr Gly Asp
        1460            1465            1470
```

-continued

```
Leu Gly Arg Phe Thr Gly Glu Gly Leu Leu Asp Phe Gln Gly Arg
    1475                1480                1485

Gly Asp Phe Gln Val Gln Leu Arg Gly His Arg Ile Glu Pro Gly
    1490                1495                1500

Glu Ile Glu Thr Val Leu Cys Glu Gln Pro Gly Val Thr Ala Ala
    1505                1510                1515

Val Ala Val Val Arg Arg Pro Asp Ser Pro Glu Ala Ala His Leu
    1520                1525                1530

Val Ala Tyr Ala Val Arg Ala Glu Glu Pro His Gly Thr Asp Gln
    1535                1540                1545

Ala Leu Arg Ala Lys Leu Ala Glu Arg Leu Pro His Tyr Met Val
    1550                1555                1560

Pro Thr Ala Val Val Thr Met Asp Ala Leu Pro Leu Thr Val Asn
    1565                1570                1575

Gly Lys Leu Asp Arg Ala Ala Leu Pro Asp Pro Trp Glu Ala Arg
    1580                1585                1590

Ala Thr Gly Asp Ser Gly Ser Asp Gly Ala Ala Val Pro Ala Leu
    1595                1600                1605

Asn Gly Arg Arg Glu Leu Ala Leu Ala Glu Ile Trp Arg Ser Leu
    1610                1615                1620

Leu Ser Thr Asp Glu Val Gly Pro Gln Asp Asn Phe Phe Ser Leu
    1625                1630                1635

Gly Gly His Ser Leu Leu Val Ala Thr Leu Ser Ala Arg Val Arg
    1640                1645                1650

Ala Glu Leu Gly Val Arg Ala Pro Leu Thr Leu Phe Leu Arg His
    1655                1660                1665

Pro Val Leu Arg Asp Leu Ala Ala Leu Pro Glu Pro Asp Gly
    1670                1675                1680

Gly Arg Ala Pro Arg Asp Asp Ala Gly Leu Arg Gln Arg Gly Thr
    1685                1690                1695

Asp Arg Ala Pro Leu Ser Ala Ala Gln Arg Arg Val Trp Ile Asp
    1700                1705                1710

Glu Gln Leu Trp Pro Gly Thr Ala Ala Tyr Thr Val Pro Glu Ala
    1715                1720                1725

Phe Trp Leu His Gly Pro Leu Asp Glu Ala Ala Phe Glu Gly Ala
    1730                1735                1740

Leu His Asp Leu Met Ala Arg His Glu Ala Leu Arg Val Arg Ile
    1745                1750                1755

Val Gly Gly Glu Asp Pro Trp Leu Ala Val Asp Asp Pro Met Ala
    1760                1765                1770

Val Arg Leu Ser Arg Ala Asp Met Arg Glu Asp Gly Glu Thr Ala
    1775                1780                1785

Val Gln Arg Leu Leu Glu Gln Ala Gly Arg Val Phe Ala Leu
    1790                1795                1800

Asp Gly Pro Leu Val Glu Ala Thr Leu Ala Arg Thr Asp Ala Glu
    1805                1810                1815

Glu Trp Val Phe Leu Leu Thr Ala His His Leu Val Val Asp Gly
    1820                1825                1830

Trp Ser Phe Asp Ile Leu Trp Arg Asp Leu Glu Ile Leu Tyr Arg
    1835                1840                1845

Asp Arg Val Ala Gly Gly Gly Ile Ser Leu Pro Pro Pro Gln Leu
    1850                1855                1860
```

-continued

```
Thr Phe Thr Asp Cys Thr Trp Trp Glu Ser Glu Arg Val Ala Ala
    1865                1870                1875

Gly Gly Asn Arg Pro His Leu Ala Phe Trp Arg Gln Glu Leu Ala
    1880                1885                1890

Gly Ile Ala His Gly Ala Gly Pro Ala Asp Ala Thr Asp Thr Asp
    1895                1900                1905

Arg Ser Gly Ser Ser Arg Ala Val Arg Leu Gly Gly Glu Leu Ser
    1910                1915                1920

Asp Gln Leu Arg Leu Ile Ala Ala Glu Leu Gly Val Thr Pro Phe
    1925                1930                1935

Val Leu Thr Leu Thr Ala Phe Ala Leu Ala Val Thr Ala Glu Gly
    1940                1945                1950

Ser Ala Glu Gln Val Ile Gly Val Glu Val Ala Gly Arg Thr Asp
    1955                1960                1965

Gln Arg Val Ala Asp Val Val Gly Leu Phe Ile Asn His Val Pro
    1970                1975                1980

Leu Arg Leu Arg Arg Arg Pro Gly Leu Thr Ala Arg Gln Ala Val
    1985                1990                1995

Ala Ala Leu Asp Asp Ala Trp Arg Gly Val Leu Glu His Ser Asp
    2000                2005                2010

Val Ser Phe Asp Thr Ile Val Asp Gly Leu Gly Glu Gln Arg Gly
    2015                2020                2025

Ala Gly Arg Gly Pro Gly Ser Asp Ile Ala Phe Ser Tyr Leu Asp
    2030                2035                2040

Ala Arg Thr Pro Pro Arg Leu Asp Gly Ile Arg Val Thr Pro Leu
    2045                2050                2055

Glu Pro Val Phe Asn Gly Thr Ala Lys Phe Gly Leu Leu Leu Glu
    2060                2065                2070

Val Phe Asp Thr Pro Asp Gly Leu Val Gly Val Phe Glu His Gln
    2075                2080                2085

Leu Ala Arg Phe Gly His Gly Arg Met Thr Arg Ile Arg Asn Arg
    2090                2095                2100

Trp Glu Ala Leu Leu Leu Gly Leu Leu Ala Asp Val Asp Val Pro
    2105                2110                2115

Leu Asp Pro Gln Gly
    2120
```

<210> SEQ ID NO 3
<211> LENGTH: 346
<212> TYPE: PRT
<213> ORGANISM: Streptomyces sp.

<400> SEQUENCE: 3

```
Met Ala Ala Tyr Pro Val Thr Pro Val Arg Thr Val Arg Thr Glu Ile
1               5                   10                  15

Ala Gly Ile Pro Arg Thr Ile Thr Leu Lys Leu Glu Gly His Ser Pro
                20                  25                  30

Trp Arg Ser Val Lys Gly Arg Thr Ala Leu Ser Leu Ile Arg Ser Val
            35                  40                  45

Ala Gly Asp Leu Thr Ala Pro Asp Ala Thr Val Glu Ser Thr Ser
        50                  55                  60

Gly Asn Leu Gly Leu Ala Leu Ser Ala Ile Cys Arg Asp Leu Gly Leu
65                  70                  75                  80

Arg Phe Ile Ala Val Val Asp His Arg Gln Ser Pro Val Ile Gln Gln
                85                  90                  95
```

```
Ala Ile Glu Ala Asn Gly Gly Glu Leu Asp Trp Val Arg Thr Pro Asp
            100                 105                 110

Asp Ala Thr Thr His Leu Gln Asp Arg Leu Ala Arg Val Arg Glu Leu
            115                 120                 125

Glu Arg Asp Leu Pro His Ala Val Trp Pro Asn Gln Tyr Glu Asn Asp
            130                 135                 140

Ala Asn Trp Arg Ile His Glu Thr Trp Thr Ala Pro Glu Phe Asp Ala
145                 150                 155                 160

Gln Val Thr His Arg Ala Gln Ala Leu Phe Ala Gly Val Ser Thr Gly
            165                 170                 175

Gly Thr Leu Ala Gly Leu Ser Arg His Phe Arg Arg Thr Arg Pro Gly
            180                 185                 190

Leu Arg Ile Val Ala Val Asp Val Arg Gly Ser Thr Val Phe Gly Gly
            195                 200                 205

Val Pro Arg Pro Arg Thr Leu Thr Gly Ile Gly Ala Gly Arg Arg Ser
            210                 215                 220

Ala Phe Leu Thr Arg Ala Ser Thr Asp Val Leu Leu Val Asp Glu
225                 230                 235                 240

Arg Gln Ala Val Ala Cys Cys His Thr Leu Arg Ala Asp Thr Gly Thr
            245                 250                 255

Ala Val Gly Gly Ser Ser Gly Ala Val Leu Ala Gly Cys Leu Glu Tyr
            260                 265                 270

Leu Tyr Arg His Pro Glu Val Arg His Ala Leu Cys Leu Cys Pro Asp
            275                 280                 285

Leu Gly Asp His Tyr Gly Pro Thr Val Tyr His Pro Ala Trp Leu Asp
            290                 295                 300

Arg Met Gly Leu Pro Ser Glu Ala His Arg Leu Arg His Arg Thr Gly
305                 310                 315                 320

Ala Ala Cys Pro Gly Phe Glu Pro Val Asp Asp Ile Thr Pro Ala Pro
            325                 330                 335

Ser Ala Pro Ser Glu Glu Asp Ala Ser Arg
            340                 345

<210> SEQ ID NO 4
<211> LENGTH: 358
<212> TYPE: PRT
<213> ORGANISM: Streptomyces sp.

<400> SEQUENCE: 4

Met Thr Glu Ser Pro Thr Thr His His Gly Ala Ala Pro Pro Asp Ser
1               5                   10                  15

Val Ala Thr Pro Val Arg Pro Trp Ser Glu Phe Arg Leu Thr Pro Ala
            20                  25                  30

Glu Ala Ala Ala Ala Ala Leu Ala Ala Arg Cys Ala Gln Arg Tyr
            35                  40                  45

Asp Glu Thr Asp Gly Pro Glu Phe Leu Leu Asp Ala Pro Val Ile Ala
            50                  55                  60

His Glu Leu Pro Arg Arg Leu Arg Thr Phe Met Ala Arg Ala Arg Leu
65                  70                  75                  80

Asp Ala Trp Pro His Ala Leu Val Val Arg Gly Asn Pro Val Asp Asp
            85                  90                  95

Ala Ala Leu Gly Ser Thr Pro Val His Trp Arg Thr Ala Arg Thr Pro
            100                 105                 110

Gly Ser Arg Pro Leu Ser Phe Leu Leu Met Leu Tyr Ala Gly Leu Leu
```

```
                    115                 120                 125
Gly Asp Val Phe Gly Trp Ala Thr Gln Gln Asp Gly Arg Val Val Thr
    130                 135                 140

Asp Val Leu Pro Ile Lys Gly Gly Glu His Thr Leu Val Ser Ser Ser
145                 150                 155                 160

Ser Arg Gln Glu Leu Gly Trp His Thr Glu Asp Ala Phe Ser Pro Tyr
                165                 170                 175

Arg Ala Asp Tyr Val Gly Leu Leu Ser Leu Arg Asn Pro Asp Gly Val
            180                 185                 190

Ala Thr Thr Leu Ala Gly Val Pro Leu Asp Asp Leu Asp Glu Arg Thr
        195                 200                 205

Leu Asp Val Leu Phe Gln Glu Arg Phe Leu Ile Arg Pro Asp Asp Ser
    210                 215                 220

His Leu Gln Val Asn Asn Ser Thr Ala Gln Gln Gly Arg Val Glu Phe
225                 230                 235                 240

Glu Gly Ile Ala Gln Ala Ala Asp Arg Pro Glu Pro Val Ala Ile Leu
                245                 250                 255

Thr Gly His Arg Ala Ala Pro His Leu Arg Val Asp Gly Asp Phe Ser
            260                 265                 270

Ala Pro Ala Glu Gly Asp Glu Glu Ala Ala Ala Leu Gly Thr Leu
        275                 280                 285

Arg Lys Leu Ile Asp Ala Ser Leu Tyr Glu Leu Val Leu Asp Gln Gly
    290                 295                 300

Asp Val Ala Phe Ile Asp Asn Arg Arg Ala Val His Gly Arg Arg Ala
305                 310                 315                 320

Phe Gln Pro Arg Tyr Asp Gly Arg Asp Arg Trp Leu Lys Arg Ile Asn
                325                 330                 335

Ile Thr Arg Asp Leu His Arg Ser Arg Lys Ala Trp Ala Gly Asp Ser
            340                 345                 350

Arg Val Leu Gly Gln Arg
        355

<210> SEQ ID NO 5
<211> LENGTH: 389
<212> TYPE: PRT
<213> ORGANISM: Streptomyces sp.

<400> SEQUENCE: 5

Met Thr Gly Pro Leu Gly Ala Gly Pro Gln Ala Leu Pro Ala Ala Pro
1               5                   10                  15

Leu Glu Asp Trp Leu Arg Glu Arg Tyr Phe Gln Ala Lys Thr Asp Ile
                20                  25                  30

Ser Ser Gly Val His Asn Tyr Thr Phe Gly Glu Leu Arg Ala Leu
            35                  40                  45

Asp Pro Ala Leu Leu Gly Thr Arg Glu Leu Asp Gln Leu Met Phe Arg
        50                  55                  60

Asp Gly Pro Ser Leu Gly Asp Glu Arg Leu Arg Ala Ala Val Ala Ala
65                  70                  75                  80

Arg Val Arg Pro Gly Pro Gly His Val Val Met Thr Thr His Gly Ser
                85                  90                  95

Ser Glu Ala Leu Tyr Leu Ala Phe Ala Ala Leu Val Arg Pro Gly Asp
            100                 105                 110

Glu Val Val Val Ala Thr Pro Ala Tyr His Ser Leu Ser Gly Leu Ala
        115                 120                 125
```

```
Thr Ala Ala Gly Ala Ser Leu Arg Pro Trp Pro Leu Arg Pro Glu Asn
    130                 135                 140

Gly Phe Ala Pro Asp Leu Asp Leu Arg Ala Val Leu Ser Asp Arg
145                 150                 155                 160

Thr Arg Leu Val Val Asn Phe Pro His Asn Pro Ser Gly Ala Cys
                165                 170                 175

Val Asp Pro Arg Gly Arg Thr Glu Leu Leu Asp Leu Val Ala Asn Ser
            180                 185                 190

Gln Ala Val Leu Leu Trp Asp Gly Ala Phe Thr Asp Leu Val His Asp
        195                 200                 205

His Pro Pro Leu Ala Glu Pro Ser Gln Asp Leu Asp Arg Val Leu Ser
    210                 215                 220

Phe Gly Thr Leu Ser Lys Ala Tyr Gly Leu Pro Gly Leu Arg Val Gly
225                 230                 235                 240

Trp Cys Val Val Pro Gln Asp Leu Val Ser Glu Leu Val Arg Ile Arg
                245                 250                 255

Asp Tyr Leu Thr Leu Ser Leu Ser Pro Leu Val Glu Arg Val Ala Ala
                260                 265                 270

Val Ala Val Glu His Ala Asp Ala Leu Ile Thr Pro Arg Leu Thr Glu
            275                 280                 285

Ala Arg His Asn Arg Arg Arg Val Leu Glu Trp Ala Ala Ala Ser Glu
        290                 295                 300

Gly Ala Ile Asp Cys Pro Val Pro Arg Gly Gly Val Thr Ala Phe Pro
305                 310                 315                 320

Arg Phe Thr Ala His Thr Asp Val Thr Asp Leu Cys Glu Arg Leu Leu
                325                 330                 335

Ala Arg His Gly Val Leu Val Val Pro Gly Arg Val Phe Gly Gln Ala
            340                 345                 350

Asp Arg Met Arg Ile Gly Phe Ser Cys Pro Arg Pro Glu Leu Glu Arg
        355                 360                 365

Gly Leu Ala Ala Ile Ser Glu Glu Leu Gly Thr His Ala Arg Gly Arg
370                 375                 380

Arg Arg Gly Thr Gly
385

<210> SEQ ID NO 6
<211> LENGTH: 447
<212> TYPE: PRT
<213> ORGANISM: Streptomyces sp.

<400> SEQUENCE: 6

Met Thr Ser Thr Pro Cys Gly Gly Thr Ala Glu Gln Lys Ser Ala Ser
1               5                   10                  15

Ala Gly Glu Ala Ala Glu Glu Lys Pro Ala Ser Leu Arg Arg Asn Arg
            20                  25                  30

Asp Phe Arg Phe Trp Trp Gly Thr Met Leu Ser Ala Ile Gly Asp
        35                  40                  45

Glu Leu Thr Ala Val Ala Leu Pro Leu Ile Val Leu Leu Ile Thr Asp
    50                  55                  60

Ser Pro Leu His Ala Gly Leu Val Gly Ser Val Glu Ser Ile Pro Pro
65                  70                  75                  80

Leu Leu Leu Ser Leu Pro Leu Gly Met Leu Val Asp Arg Val Ser Arg
                85                  90                  95

Arg Ala Val Met Leu Ala Ala Ser Leu Leu Ser Ala Ala Ser Ile Ala
                100                 105                 110
```

```
Thr Val Ala Ile Ala Phe Leu Leu Asp Gly Leu Ser Leu Pro Gln Leu
            115                 120                 125

Tyr Val Val Ala Phe Val Asn Ser Leu Ala Ala Thr Ala Tyr Arg Ile
        130                 135                 140

Ala Asp Thr Ala Ala Leu Pro Gly Ile Thr Gly Pro His Lys Leu Gly
145                 150                 155                 160

Glu Ala Ala Ser Gln Ser Glu Thr Ile Phe Gly Thr Ser Ala Leu Ile
                165                 170                 175

Ala Pro Pro Leu Ala Gly Leu Met Phe Glu Thr Met Ser Pro Ala Ala
            180                 185                 190

Pro Phe Leu Leu Asp Ala Leu Ser Phe Val Ala Val Ala Ala Ala Ile
        195                 200                 205

Leu Ala Ile Arg Ser Arg Leu Gly Pro Glu Gly Ala Pro Glu Pro Leu
210                 215                 220

Arg Trp Arg Arg Glu Leu Thr Ala Gly Met Arg Ile Thr Ala Arg Leu
225                 230                 235                 240

Pro Leu Val Arg Ala Leu Thr Leu Leu Thr Thr Leu Gly Asp Phe Leu
                245                 250                 255

Phe Ala Gly Ile Gly Leu Leu Leu Ile Val Leu Ala Lys Gly Ser Gly
            260                 265                 270

Ala Ser Gly Phe Glu Val Gly Ala Val Phe Thr Ala Ala Gly Val Gly
        275                 280                 285

Ser Leu Leu Gly Ala Ala Leu Ala Pro Arg Ile Glu Ala Gly Leu Gly
290                 295                 300

Leu Arg Thr Ala Val Val Gly Lys His Trp Leu Thr Ala Leu Leu Phe
305                 310                 315                 320

Pro Leu Leu Val Asp Leu Pro Gly Trp Gly Ile Gly Leu Val Trp
                325                 330                 335

Gly Leu Val Ala Leu Gln Val Ala Val Leu Asn Val Ile Gln Met Lys
            340                 345                 350

Tyr Leu Met Ser Gln Val His Ser Asp Gln Leu Gly Arg Val Gln Gly
        355                 360                 365

Phe Met Thr Phe Leu Ser Lys Ser Ser Leu Pro Leu Gly Tyr Ala Leu
370                 375                 380

Thr Gly Leu Leu Leu Asp Arg Trp Gly Thr Arg Gly Thr Ile Val Phe
385                 390                 395                 400

Phe Glu Val Val Leu Leu Cys Leu Ala Val Tyr Ala Leu Leu Gly Arg
                405                 410                 415

Gly Leu Arg Ala Ser His Val Thr Arg Ser Glu Asp Ala Gly Ser Gly
            420                 425                 430

Ala Pro Asp Asp Gln Pro Leu Pro Ser Arg Arg Gly Ser Glu Arg
        435                 440                 445

<210> SEQ ID NO 7
<211> LENGTH: 1073
<212> TYPE: PRT
<213> ORGANISM: Streptomyces sp.

<400> SEQUENCE: 7

Met Thr Asp Leu Asp Phe Thr Ser Trp Asp Leu Arg Thr Glu Ala Asp
1               5                   10                  15

Arg Arg Ala Phe Pro Gly Gly Leu Asp Gly Pro Ala Pro Ser Trp Asn
            20                  25                  30

Thr Asp Thr Thr Leu Val Arg Ile Val Trp Glu Gln Val Thr Arg Thr
```

-continued

```
                35                  40                  45
Pro His Ala Glu Ala Val Arg Val Gly Asp Arg Ala Leu Thr Tyr Arg
             50                  55                  60

Glu Leu Ala Asp Ser Ala Ala Arg Val Ala Arg Trp Ala Ala Gly Leu
 65                  70                  75                  80

Arg Ser Asp Arg Glu Arg Glu Leu Arg Ile Gly Val Val Ala His Arg
                 85                  90                  95

Ser Leu Pro Val Tyr Pro Val Leu Leu Gly Val Leu Ala Ala Gly Gly
                100                 105                 110

Ser Tyr Val Pro Leu Asp Pro Ala Ala Pro Val Arg Arg Leu Arg Glu
                115                 120                 125

Val Ala Arg Arg Ala Glu Leu Ala Ala Val Val Thr Asp Ala Glu Gly
            130                 135                 140

Trp Ala Gly Leu Gly Leu Ser Asp Ile Ala Gly Leu Leu Val Asp Arg
145                 150                 155                 160

Ala Leu Pro Phe Gln Arg Gly Arg Leu Gly Gly Thr Leu Thr Glu
                165                 170                 175

Phe Glu Ser Leu Pro Glu Ala Asp Gly Ala Leu Pro Gly Ala Gly Arg
                180                 185                 190

Pro Gly Gly Pro Arg Pro Asp Asp Val Ala Tyr Thr Val Phe Thr Ser
                195                 200                 205

Gly Ser Thr Gly Ala Pro Lys Gly Val Leu Val Glu His Arg Gly Ala
                210                 215                 220

Val Asn Leu Ala Arg Trp Val Ala Gly Thr Thr Asp Leu Gly Pro Gly
225                 230                 235                 240

Ser Arg Val Thr Gln Asn Ala Ser Leu His Phe Asp Ala Ser Val Gln
                245                 250                 255

Gln Ile Phe Ser Ala Trp Ser Ala Gly Ala Thr Leu Leu Pro Val Pro
                260                 265                 270

Glu Thr Val Arg Val Asp Gly Ala Arg Leu Tyr Gly Trp Leu Ala Glu
                275                 280                 285

Gln Gly Val Thr His Trp Asp Ser Val Pro Ser Leu Trp Ala Pro Val
            290                 295                 300

Val Glu His Cys Ala Gly Arg Ile Ala Ala Gly Glu Thr Val Leu Pro
305                 310                 315                 320

Ala Leu Arg Ala Val Leu Leu Ala Gly Glu Val Leu Pro Ala Ala Arg
                325                 330                 335

Val Asn Glu Trp Arg Pro Trp Gln Gln Gly His Arg Leu Phe Asn Ile
                340                 345                 350

Tyr Gly Pro Thr Glu Val Thr Val Asp Ala Thr Ala Tyr Glu Val Thr
                355                 360                 365

Gly Pro Val Thr Gly Gly Ala Pro Pro Ile Gly Arg Pro Leu Pro Gly
            370                 375                 380

Leu Arg Ala Leu Val Leu Asp Ala Asp Gly His Pro Cys Pro Pro Glu
385                 390                 395                 400

Ala Asp Gly Glu Leu Leu Leu Gly Gly Ile Gly Val Ala Arg Gly Tyr
                405                 410                 415

Leu Asp Asp Pro Ala Leu Thr Arg Glu Arg Phe Val Ala Arg Glu Gly
                420                 425                 430

Ala Arg Trp Tyr Arg Thr Gly Asp Leu Val Arg Tyr Thr Ala Glu Gly
                435                 440                 445

Asp Leu Val Phe Ser Gly Arg Arg Asp Asp Gln Val Lys Val His Gly
            450                 455                 460
```

-continued

```
Val Arg Ile Glu Leu Ala Glu Val Arg Ala Leu His Ala Asp Pro
465                 470                 475                 480

Arg Val Ala Glu Ala Ile Ala Val Val Leu Asp Asp Ala Gln Gly Arg
                485                 490                 495

His Glu Leu Ala Ala Ala Val Thr Thr Arg Thr Pro Val Ala Gly Ala
                500                 505                 510

Ala Leu Arg Ala Ser Leu Ala Glu Glu Leu Pro Ala Ala Met Val Pro
                515                 520                 525

Thr Arg Val Leu Val Asp Ala Leu Pro Arg Thr Ala Asn Gly Lys
    530                 535                 540

Ala Asp Arg Arg Ala Gly Ala Arg Met Val Arg Asp Phe Ala Asp Pro
545                 550                 555                 560

Gly Asp Gly Gly Thr Arg Pro Ala Ala Leu Thr Ala Thr Gly Arg Arg
                565                 570                 575

Leu Leu Thr Ile Trp Arg Gln Val Leu Gly Leu Pro Gln Leu Gly Pro
                580                 585                 590

Asp Asp Asp Phe Phe Arg Ser Gly Gly Asp Ser Ile Ala Thr Leu Arg
                595                 600                 605

Val Arg His Glu Cys Ala Gly Ala Gly Leu Pro Ile Gln Ser Val Asp
                610                 615                 620

Met Phe Ala His Pro Thr Val Arg Arg Leu Ala Arg His Leu Asp Arg
625                 630                 635                 640

Thr Pro Ala Glu Arg Pro Ala Thr Ala Arg Ser Val Pro Gly Ile Gly
                645                 650                 655

Ala Ser Thr Leu Leu Pro Ala Gln Arg Arg Leu Ala Val Ala Thr Leu
                660                 665                 670

Leu Ser Asp Arg Val Pro Gln Leu Gly Leu Val Gln Glu Ser His Glu
                675                 680                 685

Tyr Glu Glu Glu Leu Asp Ala Asp Ala Leu Arg Thr Ala Leu Asp Leu
                690                 695                 700

Leu Ala Glu Arg His Glu Val Leu Arg Thr Gly Val Glu Ser Arg Thr
705                 710                 715                 720

Asp Gly Phe Arg Ala Arg Thr Glu Glu Arg Val Thr Val Pro Leu Thr
                725                 730                 735

Val His Arg Ser Asp Gly Ser Gly Ala Ala Ala Arg Arg Glu Leu Ala
                740                 745                 750

Arg Ser His Ala Asp Ala Val Leu Arg Glu Gly Phe Asp Leu Ser Ala
                755                 760                 765

Pro Pro Leu Leu Lys Val Ala Ala Phe Glu Leu Glu Arg Gly Arg Phe
                770                 775                 780

Thr Leu Val Trp Thr Leu His His Val Ile Ser Asp Gly Trp Ser Trp
785                 790                 795                 800

Glu Leu Leu Gln His Glu Phe Glu Met Leu Tyr Ser Gly Leu Arg Gln
                805                 810                 815

Gly Arg Phe Arg Pro Leu Pro Ala Pro Ala Leu Pro Leu Arg Glu Leu
                820                 825                 830

Val His Arg Leu Ala Glu Ser Pro Ser Pro Ala Pro Ser Pro Glu Trp
                835                 840                 845

Leu Thr Glu Leu Arg Ala Gly Pro Leu Pro Leu Pro Pro Gly Arg
    850                 855                 860

Val Gly Gly Asp Thr Asp Arg Ala His Val Asp Trp Ala Val Thr Arg
865                 870                 875                 880
```

-continued

```
Glu Thr Asp Ala Ala Leu Arg Ala Val Ala Thr Ala Ala Gly Cys Ala
                885                 890                 895

Pro Ser Thr Gly Tyr Leu Leu Ala Tyr Ala Glu Ala Leu Gly Arg Val
            900                 905                 910

Cys Arg Gln Arg Ala Phe Pro Leu Gly Ile Val Ser Ser Gly Arg Asn
        915                 920                 925

Ala Asp Ile Pro His Ile Glu Arg Ala Val Ala Cys Leu Ala Arg Ser
    930                 935                 940

Leu Pro Val Pro Val Asp Leu Ser Gly Thr Thr Gly Glu Arg Leu Arg
945                 950                 955                 960

Arg Leu His Gly His Leu Ala Ala Val Leu Ala Gln Asp Cys Ala Asp
                965                 970                 975

Pro Asp Glu Leu Leu Ala Gly Leu Ala Pro Ala Val Arg Asp Pro Ala
            980                 985                 990

Ala Ala Phe Val Phe Gln Asn Tyr Pro Asp Ala Pro Ala Glu Pro Val
        995                 1000                1005

Pro Leu Arg Arg Val Pro Ala Ala Ser Trp Trp Arg Glu Thr Gly
    1010                1015                1020

Ser Glu Pro Leu Ala Leu Val Cys His Glu Gly Gly Val Glu Gly
    1025                1030                1035

Phe His Cys Arg Leu Glu Tyr Asp Pro Ala Glu Val Ser Ala Ala
    1040                1045                1050

Trp Ala Ala Val Leu Ala Arg Glu Ile Arg Arg Ala Gln Asp Arg
    1055                1060                1065

Leu Ala Ala Thr Glu
    1070
```

<210> SEQ ID NO 8
<211> LENGTH: 1088
<212> TYPE: PRT
<213> ORGANISM: Streptomyces sp.

<400> SEQUENCE: 8

```
Met Thr Thr Thr Ser His Ala Ala Thr Asp Pro Ala Leu Ala Leu Asp
1               5                   10                  15

Thr Leu Thr Pro Glu Glu Arg Ala Ala Trp Arg Ala Leu Asn Asp
            20                  25                  30

Gln Ala Arg Ser Trp Pro Glu Gly Leu Ala Leu Ala His Arg Leu Glu
        35                  40                  45

Glu Ala Ala Arg Arg Ala Asp Glu Pro Ala Val Gln Ala Asp Asp
    50                  55                  60

Gly Thr Tyr Thr Tyr Arg Glu Leu His Ala Glu Ala Asp Arg Ile Ala
65                  70                  75                  80

Ala Leu Leu Ala Glu Gln Gly Val Thr Glu Gly Ser Thr Val Ala Val
                85                  90                  95

Ala Thr Ala Arg Arg Leu Gly Glu Tyr Ala Ala Leu Leu Ala Ala Leu
            100                 105                 110

Lys Leu Asn Cys Ala Tyr Leu Pro Leu Ala Ala Asp Gly Pro Ala Arg
        115                 120                 125

Arg Leu Glu Phe Met Leu Ala Asp Ser Ala Ala Ala Leu Val Ala
    130                 135                 140

Asp Ala Pro Ala Ala Leu Leu Ser Glu Ala Gly Val Gly Ser Ser
145                 150                 155                 160

Leu Thr Ala Arg Val Val Ala Gly Ala Ser Arg Ala Ala Pro Ala Gly
                165                 170                 175
```

-continued

```
Trp Thr Thr Gly Glu Pro Ala Pro Arg Gly Arg Pro Ser Ala Glu
            180                 185                 190
Pro Trp Asp Arg Thr Ala Tyr Val Val Tyr Thr Ser Gly Ser Thr Gly
        195                 200                 205
Thr Pro Lys Gly Val Met Thr Gly Glu Glu Ala Leu Leu Asn Phe Cys
    210                 215                 220
Ala Trp Tyr Ile Asp Arg His Asp Val Leu Pro His Asp Arg Leu Cys
225                 230                 235                 240
Gln Thr Ala Pro Leu Thr Phe Asp Pro Ser Val Gln Gln Leu Phe Pro
                245                 250                 255
Ala Trp Leu Thr Gly Ala Cys Leu Val Val Pro Asp Glu Val Gln
            260                 265                 270
Arg Asp Gly Gly Glu Phe Leu Asp Trp Leu Ala Ala Glu Arg Ile Thr
        275                 280                 285
His Leu Asp Ile Val Thr Pro His Trp Val Gln Leu Leu Asp Val Ala
    290                 295                 300
Ala Arg Arg Gly Arg Ala Ala Leu Pro Ala Leu Arg Trp Ile Val Val
305                 310                 315                 320
Gly Gly Glu Thr Tyr Phe Phe His Gln Thr His Arg Trp His Arg Val
                325                 330                 335
Val Asp Ser Pro Ala Arg Leu Asn Thr Ile Tyr Gly Pro Thr Glu Ala
            340                 345                 350
Thr Val Asn Ala Thr Glu Phe Leu Val Asp Pro Gly Val Thr Glu Gly
        355                 360                 365
Gln Val Pro Ile Gly Arg Pro Leu Pro Asn Tyr Arg Ala Tyr Val Leu
    370                 375                 380
Asp Glu Thr Gly Ala Leu Cys Pro Pro Asn Ile Thr Gly Glu Leu Tyr
385                 390                 395                 400
Leu Ala Gly Thr Gly Leu Ala Gln Arg Tyr Cys Ser Leu Glu Ala Thr
                405                 410                 415
Glu Arg Ser Phe His Glu Arg Thr Val Ala Glu Asp Ser Thr Glu Arg
            420                 425                 430
Leu Tyr Arg Thr Gly Asp Leu Ala Arg Leu Val Glu Phe Asp Gly Gln
        435                 440                 445
Trp Ala Leu Glu Phe Gln Gly Arg Thr Asp Thr Gln Val Lys Val Ser
    450                 455                 460
Gly Tyr Arg Ile Glu Leu Glu Glu Val Gln Ala Ala Leu Ala Ala Val
465                 470                 475                 480
Pro Gly Val Thr Ala Ala Val Val Leu Arg Thr Glu Pro Ala Lys
                485                 490                 495
Gln Ile Val Cys Gly Tyr Val Ala Pro Gly Leu Thr Gly Glu Gln Val
            500                 505                 510
Arg Ala Glu Leu Ala Glu Arg Leu Pro Glu Tyr Met Leu Pro His Val
        515                 520                 525
Ile Ala Pro Leu Pro Ala Leu Pro Leu Thr Ala Asn Gly Lys Val Asp
    530                 535                 540
Lys Asp Arg Leu Leu Ala Leu Ala Ala Glu Arg His Ala Gly Ala Ala
545                 550                 555                 560
Thr Gly Gly Glu Glu Pro Arg Gly Pro Val Glu Ser Ala Ile Ala Ala
                565                 570                 575
Ile Trp Ala Glu Val Leu Gly Val Pro Arg Val Gly Ala Asp Asp Asp
            580                 585                 590
```

-continued

```
Phe Phe Val Arg Gly Gly Ser Ser Leu Leu Ala Phe Arg Val Val Ala
            595                 600                 605

Leu Leu Arg Glu Lys Gly Val Ala Ile Arg Ala Ala Asp Leu Leu Gln
            610                 615                 620

Ala Arg Thr Val Arg Ala Leu Ala Glu Arg Ala Thr Thr Asp Gly Gln
625                 630                 635                 640

Leu Ala Ala Ala Asp Gly Thr Asp Ala Pro Asp Asp Gly Ala Asp Asp
                645                 650                 655

Ile Ala Leu Leu Pro Asp Pro Arg His Glu Leu Ala Asp Asp Thr Gly
            660                 665                 670

Gln His Leu Asp Leu Pro Pro Ala Thr Ser Leu Ala Leu Leu Thr Gly
            675                 680                 685

Asp Thr Glu Asp Val Gly Asp His Ala Val Leu Thr Leu Gly Leu Pro
690                 695                 700

Leu Asp Ile Asp Pro Asp Ala Val Arg Glu Ala Leu Thr Glu Val Val
705                 710                 715                 720

Arg Arg His Pro Leu Leu Arg Thr Arg Leu Asp Thr Ser Gln Ala Arg
                725                 730                 735

Leu Arg Leu Arg Ala Leu His Val Val Arg Phe Asp Leu Pro Val Leu
            740                 745                 750

Glu Gly Asn Ser Pro Ser Leu Val Asp Arg Val Arg Pro Leu Leu Phe
            755                 760                 765

Gly His Thr Gly Leu Arg Arg Gln Leu Pro Val Ala Ala Ala Leu Val
            770                 775                 780

Arg Leu Pro Gly Gly Thr Arg Leu Leu Leu Ala Val Arg His Leu Leu
785                 790                 795                 800

Val Asp Gly Asn Ala Leu Arg Arg Ile Ser Arg Glu Leu Ala Ala Glu
                805                 810                 815

Leu Gly Leu Gly Ala Arg Pro Thr Pro Ser Ala Pro Leu Thr Glu Gln
            820                 825                 830

Leu Ala Glu Leu Arg Glu Arg Ala Arg Gly Met Arg Pro Val Arg His
            835                 840                 845

Leu Asn Ala Tyr Leu Glu Ala Glu Arg Gln Ala Gln Arg Arg Leu Ala
            850                 855                 860

Pro Arg Leu Thr Ala Glu His Thr Val Thr Glu Met Ala Ala Gly Glu
865                 870                 875                 880

Leu Pro Ala Ser Phe Leu Asp Gly Thr Arg Gly Ala Leu Glu Pro Arg
                885                 890                 895

Leu Leu Ala Ala Ala Ala Leu Ala Val Arg Arg Trp Leu Gly Leu Thr
            900                 905                 910

Ala Val Pro Leu Ser Leu Pro Arg Gln Gly Ser Pro Ala Glu Thr Val
            915                 920                 925

Ala Asn Leu Ser Asp Val Val Pro Leu Leu Ile Thr Ala Asp Gly Asp
            930                 935                 940

Gly Asp Gly Glu Ala Gly Arg Ala Leu Gly Ala Ala Thr Ala Ala Trp
945                 950                 955                 960

Ala Glu His Ala Arg Pro Glu Ala His Trp Ser Ala Ala Leu Leu Met
                965                 970                 975

His Cys Pro Gly Leu Ala His Arg Trp Pro Gly Arg Arg Glu Val Leu
            980                 985                 990

Thr Ser Ser Phe Leu Val Ala Val  Glu Leu Ala Glu Ala  Thr Thr Ala
            995                 1000                1005

Gly Leu  Gly Thr Ala Val Pro  Gly Thr Gly Gly Arg  Met Thr Asp
```

-continued

```
                1010                1015                1020
His Asp Ser Pro Thr Ala Ala Asp Pro Ala Arg Ser Gly Ser Val
    1025                1030                1035

Gln Phe Thr Val Ala Ala Gly Ser Ala Gly Pro Ser Leu Arg Leu
    1040                1045                1050

Ile Gly Trp Asp Leu Pro Ala Ala Val Leu Glu Glu Leu Ala Pro
    1055                1060                1065

Leu Trp Arg Ala Ala Leu Ala Asp Val Ala Asp Leu Arg Val Ser
    1070                1075                1080

Gly Gly Glu Ala Val
    1085

<210> SEQ ID NO 9
<211> LENGTH: 262
<212> TYPE: PRT
<213> ORGANISM: Streptomyces sp.

<400> SEQUENCE: 9

Met Ser Glu Leu Thr Asp Thr Arg Trp Leu Arg Pro Cys Ala Gly His
1               5                   10                  15

Trp Arg Glu Gly Thr Gly Pro Val Leu Leu Cys Leu Pro His Ala Gly
                20                  25                  30

Gly Gly Ala Leu Ser Tyr Ala Gly Trp Asp Arg His Pro Leu Gly Gly
            35                  40                  45

Phe Glu Pro Val Ala Val Cys Leu Pro Gly Arg Glu Asp Arg Phe Ala
        50                  55                  60

Glu Asp Pro Val Ser Gly Trp Ala Ala Leu Val Ser Ala Ile Ala Asp
65                  70                  75                  80

Ser Leu Thr Pro Leu Ala His Arg Pro Leu Ala Val Phe Gly His Ser
                85                  90                  95

Met Gly Ala Leu Thr Gly Tyr Glu Leu Leu Arg Glu Leu Ala Arg Arg
                100                 105                 110

Lys Arg Pro Ala Pro Leu Leu Leu Ala Val Ser Ala His Arg Ala Pro
            115                 120                 125

Gln Glu Met Pro Thr Ala Ala Gly Pro Pro Arg Ser Pro Arg Glu Leu
        130                 135                 140

Leu Asp Tyr Val Arg Arg Leu Asp Asp Gly Thr Ala Glu Leu Leu
145                 150                 155                 160

Asp Asp Pro Glu Trp Arg Asp Leu Val Leu Arg Pro Leu Gly Ala Asp
                165                 170                 175

Leu Arg Leu His Asp Thr Tyr Arg Ser Ser Ala Glu Pro Pro Gly Gln
            180                 185                 190

Pro Pro Leu Ala Thr Pro Phe Val Val Leu Thr Gly Glu Asp Asp Pro
        195                 200                 205

Thr Val Ser Asp Arg Thr Tyr Ala Gly Trp Ala Ala Leu Thr His Ala
    210                 215                 220

Val Ser Ala Arg Arg Val Tyr Pro Gly Gly His Phe Tyr Leu Arg Glu
225                 230                 235                 240

Gln Arg Asp Arg Leu Leu Thr Glu Leu Gly Arg Asp Leu Glu Asn Ala
                245                 250                 255

Met Arg Gly Glu Leu Arg
            260

<210> SEQ ID NO 10
<211> LENGTH: 550
```

```
<212> TYPE: PRT
<213> ORGANISM: Streptomyces sp.

<400> SEQUENCE: 10

Met Thr Ala Ile Pro Gly Ser Arg Ser Pro Ala Val Met Asp Thr Pro
1               5                   10                  15

Asp Ala Ala Val Ala Leu Leu Asp Thr Thr Ser Thr Ala Leu Arg Asp
            20                  25                  30

Val Leu Asp Leu His Arg Ile Asp Pro Glu Ala Asn Phe Phe Ser Leu
        35                  40                  45

Gly Gly Asn Ser Leu Leu Ala Val Arg Val Ala Gly Arg Leu Ser His
    50                  55                  60

Ala Leu Gly Gln Arg Ile Pro Ala Thr Ala Val Leu Asn His Pro Thr
65                  70                  75                  80

Ala Arg Gly Leu Ala Arg His Leu Ala Glu Leu Val Ser Glu Pro Ala
                85                  90                  95

Ser Pro Ala Ser Pro Ala Pro Ser Ala Pro Ala Asp Ala Thr Gly
            100                 105                 110

Thr Asp Arg Phe Pro Leu Ser Ala Ala Gln Arg Arg Val Trp Leu Leu
            115                 120                 125

His Glu Val Asp Pro Glu Arg Leu Asp His Leu Val Thr Val Ser Phe
        130                 135                 140

Glu Val Thr Gly Glu Leu Asp Pro Val Val Ala Arg Thr Ala Trp His
145                 150                 155                 160

Arg Val Val Glu Arg His Glu Ala Leu Arg Thr Arg Phe Glu Pro Ser
                165                 170                 175

Ala Pro Gly Gly Glu Glu Pro Cys Gln Val Val Glu Ser Glu Pro Leu
            180                 185                 190

Thr Glu Phe Thr Phe Leu Asp Thr Val Arg Phe Pro Glu Ala Val Arg
        195                 200                 205

Val Arg Ile Val Asp Glu Arg Val Ala Leu Leu Arg Arg Thr Pro Leu
    210                 215                 220

Ser Leu Arg Thr Gly Pro Leu Ser Arg Ile Ala Leu Leu Arg Thr Ala
225                 230                 235                 240

Pro Ser Arg Tyr Arg Leu Glu Leu Ile Val His His Ile Val Cys Asp
                245                 250                 255

Gly Trp Ser Leu Ala Leu Leu Trp Gln Asp Phe Leu Asp Ala Tyr Arg
            260                 265                 270

Arg Val Ala Val Gly Glu Pro Gly Pro Gly Pro Ser Pro His Arg Phe
        275                 280                 285

Arg Asp His Val Arg Trp Glu Arg Arg Thr Glu Ser Ala Arg Trp Pro
    290                 295                 300

Ala Gln Ala Asp Arg Val Thr Arg Arg Phe Ala Asp Arg Pro Glu Glu
305                 310                 315                 320

Leu Pro Leu Pro Ile Ala Pro Ala Pro Val Asp Glu His Asp Asp Gly
                325                 330                 335

Asp Asp Val Ser Leu Pro Leu Pro Ala Gly Leu Gly Thr Ala Leu Ala
            340                 345                 350

Arg Ala Gly Ala Glu Gly Gly His Thr Arg Leu Thr Leu Ala Leu Ala
        355                 360                 365

Ala Leu Ala Val Leu Leu His Arg Ile Ser Gly Ser Glu Asp Leu Val
    370                 375                 380

Ile Ala Val Pro Met Ala Gly Arg Val Arg Pro Glu Asp Glu Gly Thr
385                 390                 395                 400
```

```
Val Gly Leu Phe Val Asn Thr Ala Leu Ala Arg Ile Arg Leu Ala Gly
                405                 410                 415

Ala Arg Asp Val Pro Thr Leu Val Ala Arg Ala Arg Asp Glu Ala Ala
            420                 425                 430

Glu Val Leu Asp Cys Gln Thr Tyr Pro Phe Asp Gln Leu Val Ser Arg
        435                 440                 445

Leu Gly Val Pro Arg Asp Gly Thr Arg Met Pro Leu Ala Arg Val Ser
    450                 455                 460

Leu Ala Val Gln Asp Phe Ala Glu Ala Pro Leu Pro Asp Pro Asp Leu
465                 470                 475                 480

Gly Phe Thr Trp Val Glu His Asp Pro Ala Glu Arg Gln Ser Lys Leu
                485                 490                 495

Asp Leu Ala Phe Ser Leu Thr Ser Gly Ala Ala Gly Gln Pro Thr
            500                 505                 510

Leu Thr Val Thr Tyr Arg Pro Ser Leu Phe Arg Arg Thr Val Asp
        515                 520                 525

Ala Trp Ala Glu Gln Tyr Leu Ile Ala Leu Glu Asn Val Thr Arg Ala
    530                 535                 540

Val Thr Gly Gly Ala Ser
545                 550

<210> SEQ ID NO 11
<211> LENGTH: 390
<212> TYPE: PRT
<213> ORGANISM: Streptomyces sp.

<400> SEQUENCE: 11

Met Arg Leu Asp Arg His His Glu Leu Phe Arg Thr Ser Val Arg Ala
1               5                   10                  15

Val Leu Glu Arg Leu Phe Leu Pro Glu Leu Glu Asp Trp Glu Lys Ala
            20                  25                  30

Gly Glu Met Pro Thr His Glu Leu Tyr Arg Ser Leu Gly Glu Glu Gly
        35                  40                  45

Leu Leu Gly Leu Thr Leu Pro Val Asp Asp Gly Leu Gly Leu Asp
    50                  55                  60

Leu Gly Tyr Ser His Val Trp Ala Arg Glu Leu Gly Arg Leu Pro Ala
65                  70                  75                  80

Gly Ser Pro Ala Met Ser Leu Ser Val Gln Thr Asp Ile Val Leu Pro
                85                  90                  95

Leu Leu Ala Glu Glu Gly Gly Thr Gly Val Arg Asp Ala Tyr Leu Arg
            100                 105                 110

Ser Ala Val Arg Gly Glu Leu Val Ala Ala Leu Ala Thr Glu Pro
        115                 120                 125

Gly Gly Gly Ser Asp Leu Ala Ala Val Arg Thr Thr Ala Val Arg Asp
    130                 135                 140

Ala Asp Gly Leu Arg Leu Asn Gly Asp Lys Ala Phe Leu Thr Asn Gly
145                 150                 155                 160

Ser Val Ala Asp Phe Ala Val Leu Cys His Leu Leu Pro Ser Gly
                165                 170                 175

Ala Asp Glu Gly Gly Asn Pro Pro Asp Gly Leu Asp Ser Leu Thr Leu
            180                 185                 190

Val Leu Val Pro Thr Gly Leu Pro Gly Val Arg Gln Glu Arg His Thr
        195                 200                 205

Gly Lys Leu Gly Asn Arg Ala Cys Asp His Gly Arg Leu Ser Phe Thr
```

-continued

```
               210                 215                 220
Asp Val Arg Val Pro Glu Glu Asn Leu Leu Gly Lys Pro Gly Ser Gly
225                 230                 235                 240

Tyr Glu Ala Leu Thr Arg Val Phe Thr Arg Glu Arg Thr Phe Leu Ala
                245                 250                 255

Ala Val Cys Thr Ala Arg Ala Ala Thr Met Leu Asp Arg Ala Thr Thr
            260                 265                 270

Tyr Ala Arg Gly Arg Ala Val Leu Gly Arg Pro Leu Leu Gln His Gln
                275                 280                 285

Ala Ile Ala Phe Arg Leu Ala Glu Leu Asp Ala Glu Leu Ala Leu Ile
        290                 295                 300

Glu Gln Tyr Thr Asp Ala Val Phe Gln Arg Leu Gln Glu Asp Ala Ala
305                 310                 315                 320

Ala Leu Arg Gln Ala Ser Ile Ala Lys Leu Arg Ala Ser Arg Leu Glu
                325                 330                 335

Arg Glu Cys Ala Asp Leu Leu Leu Gln Leu His Gly Gly Ala Gly Tyr
            340                 345                 350

Leu Glu Gly Gly Pro Val Glu Arg Gly Tyr Arg Asp Ala Arg Ala Tyr
                355                 360                 365

Ala Leu Ala Gly Gly Ala Asp Glu Ala Leu Leu His Leu Ile Ala Gly
        370                 375                 380

His Pro Arg Thr Asp Val
385                 390

<210> SEQ ID NO 12
<211> LENGTH: 360
<212> TYPE: PRT
<213> ORGANISM: Streptomyces sp.

<400> SEQUENCE: 12

Met Thr Ile Gln Ala Val Pro Glu Pro Ala Thr Arg Thr Glu His Leu
1               5                   10                  15

Leu Phe Leu Asp Arg Ala Ala Val Arg Thr Cys Ala Ala Gly Ile Asp
                20                  25                  30

Pro Val Ala Val Glu Asp Val Leu Arg Ala His Ala Ala Gly His
            35                  40                  45

Thr Ala Leu Pro Ala Glu Gly Tyr Leu Pro Trp Ala Asn Ser His Gly
        50                  55                  60

Ala Tyr Cys Arg Ser Ile Ala Met Leu Gly Ser Val Gly Ala Ala Asp
65                  70                  75                  80

Pro Thr Val Pro Thr Ala Tyr Gly Met Lys Leu Ile Asn Ala Ala Thr
                85                  90                  95

Ser Asn Pro Ala Gln Gly Arg Glu Arg Ala Gly Gly Val Ser Phe Leu
            100                 105                 110

Phe Asp Pro Glu Thr Ala Arg Pro Ala Val Val Ala Glu Ala Ala Tyr
        115                 120                 125

Leu Ser Ala Leu Arg Thr Gly Ala Tyr Thr Met Ser Ser Leu Arg His
130                 135                 140

Leu Gly Pro Glu Arg Phe Gln Glu Val Thr Leu Ile Gly Cys Gly Ala
145                 150                 155                 160

Gln Ala Arg Thr His Ala Glu Leu Leu Ala Arg Tyr Phe Pro Asp Val
                165                 170                 175

Arg Thr Leu His Val His Asp Leu Leu Pro Glu Arg Ala Ser Ala Phe
            180                 185                 190
```

-continued

```
Ala Ser Trp Val Glu Gly Ser Glu Leu Pro Phe Thr Val Pro His
        195                 200                 205
Gly Arg Ala Ala Glu Ala Ala Ala Ser Thr Val Val Ile Thr Leu
210                 215                 220
Thr Ile Thr Asp Thr Gly Tyr Leu Ser Pro Asp His Leu Arg Pro Gly
225                 230                 235                 240
Thr Phe Val Ala His Val Ser Leu Asp Asp Leu Leu Pro Glu Val Phe
                245                 250                 255
Asp Arg Ala Gln Ala Leu Tyr Val Asp Asp Val Glu Leu Val Arg Asp
                260                 265                 270
Asn Pro Arg Arg Val Leu Gly Arg Leu Leu Gly Glu Arg Val Leu
            275                 280                 285
Ala Pro Gly Thr Pro Lys Pro Gly Thr Ser Thr Ile Arg Gly Thr Leu
290                 295                 300
Gly Asp Val Leu Thr Ala Ala Val Pro Ala Glu Arg Pro Gly Thr Gly
305                 310                 315                 320
Val Val Val Ser Asn Pro Phe Gly Met Ala Val Leu Asp Val Gly Leu
                325                 330                 335
Leu Ala Arg Val Tyr Ala Arg Ala Ala Asp Gly His Gly Thr Arg
            340                 345                 350
Leu Asp Leu Leu Gly Ala Asp Arg
        355                 360

<210> SEQ ID NO 13
<211> LENGTH: 308
<212> TYPE: PRT
<213> ORGANISM: Streptomyces sp.

<400> SEQUENCE: 13

Met Thr Glu Pro Arg Gly Leu Tyr Ser Leu Ala Asp Leu Asp Asp Ala
1               5                   10                  15
Ser Val Gln Arg Ile Val Arg Arg Thr Ile Glu Leu His Ala Asp Arg
            20                  25                  30
Asp Ala His Thr Arg Pro Leu Ala Gly Leu Val Ala Gly Leu Leu Phe
        35                  40                  45
Thr Lys Thr Ser Thr Arg Thr Arg Thr Ala Phe Thr Ser Gly Ala Ile
    50                  55                  60
Arg Leu Gly Gly Ala Pro Ile Ala Phe Gly Pro Thr Asp Leu Gln Thr
65                  70                  75                  80
Asn Thr Gly Glu Ser Ala Ala Asp Thr Gly Arg Met Leu Ala Gly Met
                85                  90                  95
Leu Asp Leu Leu Val Val Arg Thr Ala Gly Pro Met Arg Glu Leu Arg
            100                 105                 110
Glu Leu Ser Gly Glu Gly Glu Leu Pro Val Val Asn Ala Met Ser Ala
        115                 120                 125
Glu Glu His Pro Thr Gln Gly Leu Ala Asp Leu Ala Thr Leu Ile His
    130                 135                 140
His Phe Gly Gly Leu Asp Gly Val Arg Val Leu Tyr Val Gly Glu Gly
145                 150                 155                 160
Asn Asn Thr Ala Val Ala Leu Ala Arg Val Leu Ser Arg Gln Pro Gly
                165                 170                 175
Cys His Ala Val Phe Ala Ser Pro Ala Gly Tyr Arg Leu Pro Asp Ala
            180                 185                 190
Val Leu Ala Glu Thr Ala Ala Ile Ala Asp Arg Arg Gly Gly Ser Val
        195                 200                 205
```

```
Thr Gln Ala His Ala Pro Gly Asp Val Val Gly Glu Val His Ala Val
    210                 215                 220
Tyr Thr Ser Arg Trp Gln Thr Thr Gly Ser Thr Lys Pro Asp Pro Ser
225                 230                 235                 240
Trp Arg Asp Val Phe Arg Pro Phe His Val Asp Ala Ala Leu Met Asn
                245                 250                 255
Arg Trp Pro Asp Ala Val Phe Leu His Asp Leu Pro Ala His Arg Gly
            260                 265                 270
Glu Glu Val Ser Gly Glu Val Leu Asp Gly Lys Ser Ser Leu Ala Trp
        275                 280                 285
Thr Gln Ala Gly Leu Lys Ala Ala Gly Ala Met Ala Val Leu Glu Trp
    290                 295                 300
Val Val Thr Thr
305

<210> SEQ ID NO 14
<211> LENGTH: 457
<212> TYPE: PRT
<213> ORGANISM: Streptomyces sp.

<400> SEQUENCE: 14

Met Arg Thr Arg Ile Ala Leu Arg Thr Glu Gln Val Ala Pro Leu Ser
1               5                   10                  15
Pro Ala Gln Tyr Ser Leu Trp Phe Leu Asp Gln Leu Thr Gly Pro Ser
            20                  25                  30
Ser Glu Tyr Val Gln Pro Tyr Ala Tyr Arg Leu Arg Gly Pro Leu Asp
        35                  40                  45
Thr Ser Ala Leu Glu Asp Ala Leu Asn Ala Leu Val Glu Arg His Glu
    50                  55                  60
Pro Leu Arg Thr Arg Val Asp Gln Val Ala Gly Glu Pro Arg Gln Ala
65                  70                  75                  80
Val Arg Arg His His Pro Arg Pro Leu Arg Arg Leu Asp Leu Ser Gln
                85                  90                  95
Asp Pro Ala Arg Ala Gly Arg Glu Ala Ala Phe Ala Leu Arg Pro
            100                 105                 110
Phe Asp Leu Ala Gly Glu Asp Pro Leu Arg Thr Leu Leu Val Arg Leu
        115                 120                 125
Gly Gln Arg Asp His Leu Leu Val Cys Ser Leu His His Ile Cys Cys
    130                 135                 140
Asp Gly Leu Ser Leu Ala Val Leu Gly Glu Asp Leu Ala Ala Leu Tyr
145                 150                 155                 160
Arg Ala Ala His Gly Gln Asp Val Gly Gln Ala Leu Pro Pro Leu
                165                 170                 175
Pro Val His Tyr Arg Asp Thr Val Leu Ala Arg Ala Arg Gln Ala Asp
            180                 185                 190
Cys Pro Ala Gly Arg Pro Ala Leu Ala Arg Trp Arg Ala Arg Leu Glu
        195                 200                 205
Gly Ala Ala Pro Leu Arg Leu Pro Thr Asp Arg Ala Arg Pro Glu Val
    210                 215                 220
Arg Thr Ala Arg Gly Asp Arg Val Glu Val Val Pro Ala Asp Val
225                 230                 235                 240
Thr Ser Ala Ala Arg Ala Ala Ala Arg His Arg Val Thr Leu Tyr
                245                 250                 255
Met Val Met Leu Ser Val Phe Ala Met Leu Leu His Arg Arg Gly Gly
```

```
                260                 265                 270
Gly Arg Asp Leu Cys Val Gly Thr Pro Val Ser Gly Arg Ser Ala Pro
            275                 280                 285
Glu Glu Glu Ala Leu Ile Gly Leu Phe Thr Asn Thr Val Val Leu Arg
        290                 295                 300
Leu Asp Leu Ser Asp Asp Arg Asp Leu Ala Glu Leu Leu His Gln Val
305                 310                 315                 320
Arg Gly Arg Ala Leu Ala Ala Tyr Gln Asp Gly His Val Pro Phe Glu
                325                 330                 335
His Val Val Asp Glu Leu Arg Pro Pro Arg Asp Leu Ser Arg Thr Pro
            340                 345                 350
Val Phe Gln Val Met Phe Ser Phe Gln Asp Phe Glu Glu Asp Ala Leu
        355                 360                 365
Ala Leu Asp Gly Leu Arg Cys Thr Pro Trp Glu Ile Pro Val Gly Ser
        370                 375                 380
Ser Lys Phe Asp Leu Glu Leu Glu Leu Gly Arg Glu Gly Asp Arg Leu
385                 390                 395                 400
Arg Gly Phe Leu Glu Tyr Ser Thr Asp Leu Tyr Glu Ala Gly Thr Ala
                405                 410                 415
Arg Gly Met Ala Asp Glu Tyr Leu Ala Leu Leu Arg Glu Ala Leu Gly
            420                 425                 430
Leu Pro Gly Asp Ser Pro Gly Ala Ala Asp Pro Val Arg Ser Ser
        435                 440                 445
Asp Pro Ser Pro Glu Glu Pro Thr Arg
    450                 455

<210> SEQ ID NO 15
<211> LENGTH: 63
<212> TYPE: PRT
<213> ORGANISM: Streptomyces sp.

<400> SEQUENCE: 15

Met Asn Asp Thr Pro Ala Asp Thr Ala Tyr Gln Val Val Leu Asn Asp
1               5                   10                  15
Glu Glu Gln Tyr Ser Val Trp Pro Val Gly Arg Pro Leu Pro Ala Gly
                20                  25                  30
Trp Arg Ala Glu Gly Thr Val Gly Gly Arg Gln Ala Cys Leu Asp His
            35                  40                  45
Ile Glu Thr Val Trp Thr Asp Leu Arg Pro Leu Ser Ala Arg Ala
        50                  55                  60

<210> SEQ ID NO 16
<211> LENGTH: 610
<212> TYPE: PRT
<213> ORGANISM: Streptomyces sp.

<400> SEQUENCE: 16

Met Pro Thr Thr Gly Thr Ala Ala Asp Arg Ser Thr Asp Thr Val Pro
1               5                   10                  15
Ala Leu Leu Ala Glu Val Ala Arg Met Pro Gly Ala Pro Ala Leu
                20                  25                  30
Ile Thr Pro Asp Arg Thr Leu Thr His Asp Glu Leu Asp Asp Leu Thr
            35                  40                  45
Ala Arg Leu Ala Gly Leu Leu Arg Arg His Gly Ile Gly Arg Gly Gln
        50                  55                  60
Arg Ile Ala Val Leu Ala Asp Arg Thr Trp Gln Gly Val Cys Cys Pro
```

```
                65                  70                  75                  80
Leu Ala Val Leu Arg Ala Gly Ala Ala Tyr Val Pro Leu Asp Pro Ser
                    85                  90                  95
Asp Pro Glu Asp Arg Leu Arg Glu Val Val Ala Leu Thr Gly Ala Arg
                100                 105                 110
Ala Val Leu Gly Arg Ala Glu Ser Leu Gly Glu Leu Pro Gly Leu Gly
                115                 120                 125
Ile Pro Val Ile Pro Ala Glu Pro Pro Gly Asp Leu Ala Gly Gly Ala
                130                 135                 140
Pro Pro Ala Thr Arg Ala Asp Ala Glu Pro Pro Leu Pro Asp Asp Leu
145                 150                 155                 160
Ala Tyr Val Met Leu Thr Ser Gly Thr Thr Gly Thr Pro Lys Ala Val
                    165                 170                 175
Leu Val Pro His Arg Ala Val Thr Arg Ala Arg Ser Leu Val Pro
                180                 185                 190
Leu Phe Gly Val Thr Ser Thr Asp Arg Val Leu His Trp Thr Ser Leu
                195                 200                 205
Ile Trp Asp Thr Ser Gly Glu Glu Ile Tyr Pro Ala Leu Leu Gly Gly
                210                 215                 220
Ala Ala Leu Val Val Asp Gly Arg Val Glu Thr Arg Ser Val Pro Ala
225                 230                 235                 240
Leu Leu Ala Ala Val Arg Glu His Arg Val Thr Val Asp Leu Pro
                    245                 250                 255
Thr Ala Met Trp Asn Glu Leu Ala His Tyr Leu Ala Leu Gly Gly Glu
                    260                 265                 270
Glu Leu Pro Pro Ala Leu Arg Leu Val Val Ile Gly Gly Glu Ala Ala
                275                 280                 285
His Ala Arg Thr Val Arg Leu Trp Asn Glu Arg Val Pro Asp Arg Val
                290                 295                 300
Arg Leu Leu Asn Thr Tyr Gly Gln Thr Glu Thr Val Met Val Thr His
305                 310                 315                 320
Ala Ala Glu Leu Gly Gly Pro Ala Gly Arg Ala Leu Arg Asp Gly Asp
                    325                 330                 335
Pro Val Pro Ile Gly Arg Pro Leu Pro His Ile Arg Gln Val Leu Val
                340                 345                 350
Pro Ser Asp Asp Gly Pro Asp Glu Leu Trp Thr Gly Gly Pro Gly Leu
                355                 360                 365
Ala Trp Gly Tyr Ala Asp Arg Pro Ala Leu Thr Ala Ala Phe Gly
                370                 375                 380
Pro Ala Pro Gly Ala Gly Gly Arg Phe Tyr Arg Thr Gly Asp Leu Val
385                 390                 395                 400
Arg Thr Leu Pro Asp Gly Ser Leu Val His Ala Gly Arg Ala Asp Arg
                    405                 410                 415
Arg Leu Lys Val Arg Gly Val Arg Val Glu Pro Ala Glu Val Glu Arg
                420                 425                 430
Ala Met Thr Thr Cys Pro Gly Val Val Ala Ala Val Phe Pro Val
                    435                 440                 445
Gly Asp Asp Pro Glu His Leu Arg Leu Tyr Gly Ala Phe Val Pro Ser
                450                 455                 460
Lys Ser Gly Pro Ala Thr Glu Arg Glu Val Ala Glu His Cys Ala Arg
465                 470                 475                 480
Arg Leu Pro Arg Ser Leu Leu Pro His Arg Ile Ala Val Val Thr Ala
                    485                 490                 495
```

```
Leu Pro Leu Leu Arg Thr Gly Lys Val Asp Arg Ala Ala Leu Gln Ala
            500                 505                 510

Leu Phe Thr Asp Ala Thr Thr Pro Ser Glu Gly Ala Ser Ala Gly Ser
        515                 520                 525

Ala Ser Gly Pro Ser Leu Thr Ala Arg Leu Val Glu Leu Cys Gly Arg
    530                 535                 540

Ala Leu Gly Ala Pro Cys Gly Ala Gly Glu Ser Leu Phe Ala Arg Gly
545                 550                 555                 560

Gly Asp Ser Leu Thr Val Thr Arg Leu Ile Ser Leu Val His Arg Glu
                565                 570                 575

Leu Glu Thr Asp Leu Thr Phe Gln Asp Val Phe Asp His Pro Thr Pro
            580                 585                 590

Gln Glu Leu Ala Gln Leu Val Glu Val Ser Gly Pro Phe Arg Gly Glu
        595                 600                 605

Pro Gln
    610

<210> SEQ ID NO 17
<211> LENGTH: 445
<212> TYPE: PRT
<213> ORGANISM: Streptomyces sp.

<400> SEQUENCE: 17

Met Glu Pro Asp Trp Arg Arg Leu Pro Gly Trp His Asp Val Thr Ala
1               5                   10                  15

Ala Gln Trp His Asp Val Gln Trp Gln Arg Ala His Cys Val Lys Asn
                20                  25                  30

Ala Arg Gln Leu Arg Ala Val Val Gly Asp Gly Leu Asp Asp Lys Phe
            35                  40                  45

Tyr Asp Asp Leu Thr Glu Asp Gln Glu His Met Ala Thr Met Ala Met
        50                  55                  60

Leu Ile Thr Pro Gln Met Leu Asn Thr Ile Ala Pro Glu Thr Pro Ala
65                  70                  75                  80

Asp Ser Asp Gly Tyr His Asp Ala Phe Tyr Ala Asp Pro Val Arg Arg
                85                  90                  95

Tyr Met Val Pro Val Arg Ser Asp Arg Asp Leu Arg Trp Pro Ser His
                100                 105                 110

Pro Leu Ser Ser Arg Asp Ser Leu His Glu Ala Glu Met Trp Val Val
            115                 120                 125

Glu Gly Leu Thr Arg Arg Tyr Pro Thr Lys Val Leu Ala Glu Leu Val
        130                 135                 140

Ala Thr Cys Pro Gln Tyr Cys Gly His Cys Thr Arg Met Asp Leu Val
145                 150                 155                 160

Gly Gly Ser Thr Pro Ser Val Asp Lys Gln Arg Leu Thr Leu Arg Pro
                165                 170                 175

Ala Asp Arg Gln Glu Ala Ile Leu Asp His Leu Arg Arg Thr Pro Gly
                180                 185                 190

Val Arg Asp Val Val Ser Gly Gly Asp Val Ala Asn Val Pro Trp
            195                 200                 205

Pro Arg Leu Glu Ser Phe Leu Leu Arg Leu Glu Ile Asp Ser Val
        210                 215                 220

Arg Asp Ile Arg Leu Ala Ser Lys Ala Leu Val Gly Leu Pro Gln His
225                 230                 235                 240

Trp Leu Gln Pro Gln Val Val Ser Gly Leu Glu Asn Val Ala Gly Val
```

```
                    245                 250                 255
Ala Ala Arg Arg Gly Val His Leu Ala Val His Thr His Ala Asn His
            260                 265                 270

Val Gln Ser Val Thr Pro Leu Val Ala Glu Gly Ala Arg Ala Leu Leu
        275                 280                 285

Asp Ala Gly Val Arg Asp Val Arg Asn Gln Gly Val Leu Met Arg Gly
    290                 295                 300

Val Asn Asp Ser Thr Ala Ala Leu Leu Asp Leu Cys Phe Ala Leu Gln
305                 310                 315                 320

Asp Glu Ala Gly Ile Leu Pro Tyr Tyr Phe Tyr Met Cys Asp Met Val
                325                 330                 335

Pro Gly Ala Glu His Trp Arg Thr Ser Leu Ala Glu Ala Gln Asp Leu
            340                 345                 350

Gln His Ala Ile Met Gly Tyr Leu Pro Gly Tyr Ala Thr Pro Arg Ile
        355                 360                 365

Val Cys Asp Val Pro Tyr Val Gly Lys Arg Trp Val His Gln Ala Val
    370                 375                 380

Glu Tyr Asp Arg Glu Arg Gly Ile Ser Tyr Trp Thr Lys Asn Tyr Arg
385                 390                 395                 400

Thr Ala Ile Glu Leu Asp Asp Pro Asp Ala Leu Thr Arg Arg Tyr Pro
                405                 410                 415

Phe His Asp Pro Leu Ser Thr Leu Pro Glu Ser Gly Trp Arg Trp Trp
            420                 425                 430

Glu Arg Gln Val Ala Ala Arg Glu Gly Gln Ala Cys Ala
        435                 440                 445

<210> SEQ ID NO 18
<211> LENGTH: 293
<212> TYPE: PRT
<213> ORGANISM: Streptomyces sp.

<400> SEQUENCE: 18

Met Glu Thr Ser Pro Thr Met Arg Ile Ile Glu Thr His Arg Asp Leu
1               5                   10                  15

Leu Ser Arg Leu Leu Pro Gly Asp Thr Val Gly Gly Leu Ala Val His
            20                  25                  30

Glu Gly Gln Phe His His Val Val Ile Gly Ser His Arg Val Val Cys
        35                  40                  45

Phe Ala Arg Thr Arg Ala Ala Ala Asp Arg Leu Pro Gly Arg Ala Asp
    50                  55                  60

Val Leu Arg Ala Leu Ala Gly Ile Asp Leu Gly Phe Arg Thr Pro Gln
65                  70                  75                  80

Pro Leu Ser Glu Gly Gly Ala Gln Gly Thr Asp Glu Pro Pro Tyr Leu
                85                  90                  95

Val Leu Ser Arg Ile Pro Gly Ala Pro Leu Glu Asp Asp Val Leu Thr
            100                 105                 110

Ser Pro Glu Val Ala Glu Ala Val Ala Arg Gln Tyr Ala Thr Leu Leu
        115                 120                 125

Ser Gly Leu Ala Ala Ala Gly Asp Glu Glu Lys Val Arg Ala Ala Leu
    130                 135                 140

Pro Glu Ala Pro Ala Asn Glu Trp Gln Glu Phe Ala Thr Gly Val Arg
145                 150                 155                 160

Thr Glu Leu Phe Pro Leu Met Ser Asp Gly Gly Arg Glu Arg Ala Glu
                165                 170                 175
```

```
Arg Glu Leu Ala Ala Leu Asp Ala Leu Pro His Leu Thr Ser Ala Val
            180                 185                 190

Val His Gly Asp Leu Gly Gly Glu Asn Val Leu Trp Glu Thr Val Asp
        195                 200                 205

Gly Val Pro Arg Met Ser Gly Val Val Asp Trp Asp Glu Val Gly Ile
    210                 215                 220

Gly Asp Pro Ala Glu Asp Leu Ala Ala Ile Gly Ala Ser Tyr Gly Glu
225                 230                 235                 240

Glu Leu Leu Gly Arg Val Leu Ala Leu Gly Gly Trp Ala Asp Asn Gly
                245                 250                 255

Thr Ala Glu Arg Ile Ser Ala Ile Arg Gly Thr Phe Ala Leu Gln Gln
            260                 265                 270

Ala Leu Tyr Ala Gln Arg Asp Gly Asp Glu Glu Leu Ala Asp Gly
        275                 280                 285

Leu Ser Gly Tyr Arg
    290
```

<210> SEQ ID NO 19
<211> LENGTH: 343
<212> TYPE: PRT
<213> ORGANISM: Streptomyces sp.

<400> SEQUENCE: 19

```
Met Pro Thr Cys Arg Val Ile Arg Asn Trp Gly Val Thr Met Asp Pro
1               5                   10                  15

Val Glu Tyr Glu Met Leu Arg His Met Trp Phe Pro Val Ala Arg Val
            20                  25                  30

Ala Asp Leu Lys Asn Gly Val Ala Ser Gly Ser Ile Leu Gly Glu Glu
        35                  40                  45

Leu Val Val Tyr Gly Asp Glu Gly Ser Val Thr Val Ala Gln Gly Phe
    50                  55                  60

Cys Pro His Arg Gly Val Ala Leu Arg Leu Gln Leu Arg Asp Gly
65                  70                  75                  80

Ala Leu Glu Cys Pro Tyr His Gly Trp Leu Phe Glu Thr Gly Ser Gly
                85                  90                  95

Arg Cys Thr Arg Ile Pro Ser Leu Pro Pro Gly Arg Gly Arg Pro His
            100                 105                 110

Thr Ala Leu Arg Thr His Pro Ala Glu Val Ala Tyr Gly Leu Val Trp
        115                 120                 125

Ser Cys Leu Gly Asp Pro Phe Leu Pro Leu Pro Arg Leu Pro Glu Tyr
    130                 135                 140

Val Asp Ser Trp Arg Leu Gly Ala Gly Glu Pro Tyr Thr Leu Asn
145                 150                 155                 160

Cys Gly Met Arg Leu Leu Thr Glu Asn Phe Arg Asp Lys Ala His Phe
                165                 170                 175

Pro Phe Val His Ala Asp Ser Met Gly His Val Asp Lys Val Val Gln
            180                 185                 190

Pro Tyr Arg Ile Ser Arg Asp Gly Trp Arg Leu Gly Trp Ser Ser Ser
        195                 200                 205

Leu Gly Ser Glu Gly Val Pro Glu Asp Leu Ala Glu Glu Leu Ser His
    210                 215                 220

Arg Leu Asp Tyr His Ile Thr Met Pro Val Phe Ala Ser Ile Cys Val
225                 230                 235                 240

Ser Ser Pro Ser Gly Gly Arg Arg Leu Val Ala Gln Val Ala Thr Pro
                245                 250                 255
```

```
Val Ser Ala Asp Gly Lys Ala Val Arg Gln Phe Trp Leu Ala Gly Thr
            260                 265                 270

Asp Ala Glu Ser Thr Ala Gln Gly Ala Val Leu Ala Asp Val Leu Gly
            275                 280                 285

Phe Glu Arg Gln Val Phe Glu Glu Asp His Pro Ile Val Glu Asn Gln
            290                 295                 300

Trp Pro Val Glu Ala Pro Leu Asp Val His Ser Gln Val His Thr Pro
305                 310                 315                 320

Ala Asp Arg Phe Ser Ile Thr Tyr Arg Lys Val Tyr Gly Glu Leu Leu
            325                 330                 335

Met Asn Phe Lys Glu Ser Arg
            340

<210> SEQ ID NO 20
<211> LENGTH: 236
<212> TYPE: PRT
<213> ORGANISM: Streptomyces sp.

<400> SEQUENCE: 20

Met Pro His Arg Pro Cys Gly Ala Pro Ala Asp Glu Pro Gly Ala
1               5                   10                  15

Arg Val Arg Ile Leu Leu Ala Glu Asp Arg Asp Val Tyr Arg Glu Gly
            20                  25                  30

Leu Phe Val Leu Leu Ser Glu Ile Ala Asn Ala Glu Val Val Gly Thr
            35                  40                  45

Ala Val Asp Arg Lys Glu Leu Val His Gln Ser Thr Arg Leu Ser Pro
        50                  55                  60

Asp Val Val Val Ala Gly Thr Ser Leu Val Leu Pro Asp Gly Leu Pro
65                  70                  75                  80

Ala Leu Ser Arg Leu Pro Glu Ala Val Ser Gly Asn Thr Val Met Ala
                85                  90                  95

Ala Glu Arg Asp Thr Asp Glu Leu Leu Ser Ala Ala Leu Ala Ala Gly
            100                 105                 110

Val His Gly Tyr Val Pro Leu Ser Ser Pro Arg Glu Asp Phe Asp Ala
        115                 120                 125

Ala Ile Gln Ala Val Ala Ala Gly Gly Gly Phe Leu Pro Thr His Val
    130                 135                 140

Thr Arg Arg Leu Val Arg Asn Phe His Leu Val Pro Arg Arg Thr Asp
145                 150                 155                 160

Arg Pro Ala Glu Leu Glu Leu Ser Glu Arg Glu Gln Gln Val Leu
                165                 170                 175

Leu Leu Val Gly Asp Gly Arg Ser Asn Arg Glu Ile Ala Arg Thr Leu
            180                 185                 190

Arg Val Ser Glu Ala Thr Val Lys Ser His Val Ser Arg Val Leu Ala
        195                 200                 205

Lys Leu Glu Leu Arg Asp Arg Val His Ala Ala Gln Leu Val Trp Arg
    210                 215                 220

Leu Gly Leu Gly Ser Pro Ser Leu Leu Pro Gln Thr
225                 230                 235

<210> SEQ ID NO 21
<211> LENGTH: 452
<212> TYPE: PRT
<213> ORGANISM: Streptomyces sp.

<400> SEQUENCE: 21
```

-continued

```
Met Thr Met Lys Cys Arg Val Leu Gly Ser Ala Pro Tyr Thr Arg Gln
1               5                   10                  15

Ala Leu Ala Gly Ala Ala Leu Leu Ile Ala Gly Thr Val Met Gly Pro
            20                  25                  30

Ala Ala Ala Ser Ser Gly Asp Glu Arg Asp Thr Ser Arg Ala Arg Asn
            35                  40                  45

Val Ile Leu Leu Val Gly Asp Gly Met Gly Asp Ser Glu Ile Thr Leu
        50                  55                  60

Ala Arg Asn Tyr Thr Val Gly Ala Gly Gly Arg Leu His Met Asp Gly
65                  70                  75                  80

Phe Pro Met Thr Gly Ser Tyr Thr Thr Tyr Ser Val Asp Arg Asp Gly
                85                  90                  95

Arg Pro Asn Tyr Val Thr Asp Ser Ala Ala Ser Ala Thr Ala Trp Ala
                100                 105                 110

Thr Gly His Lys Thr Val Asn Asp Arg Ile Ser Lys Thr Ala Asp Thr
            115                 120                 125

Asp Arg Ala Val Pro Thr Ile Leu Glu Leu Ala Arg Gln Gly Gly Leu
130                 135                 140

Ala Thr Gly Ser Val Thr Ser Ala Glu Leu Thr Asp Ala Thr Pro Ala
145                 150                 155                 160

Ala Leu Thr Ser His Val Thr Asp Arg Ser Cys Gln Gly Pro Ala Asp
                165                 170                 175

Met Glu Arg Cys Pro Thr Asp Thr Arg Ala Ala Gly Gly Pro Gly Ser
                180                 185                 190

Ile Ala Glu Gln Thr Val Ala His Arg Val Asp Val Leu Leu Gly Gly
            195                 200                 205

Gly Arg Gln Arg Phe Asp Gln Thr Ile Thr Gln Gly Pro Glu Arg Gly
        210                 215                 220

Ser Thr Val Leu Gln Arg Ala Arg Gln His Gly Tyr Arg Val Val Thr
225                 230                 235                 240

Asp Ala Arg Gly Leu Asp Ala Val Arg Pro Gly Arg Pro Val Leu Gly
                245                 250                 255

Leu Phe Ala Pro Glu Glu Leu Pro Val Ala Trp Thr Gly Thr Pro Ala
                260                 265                 270

Ala Ala Gly Gly Thr Ala Pro Gln Arg Cys Val Thr Asp Arg Glu Pro
            275                 280                 285

Ser Asp Gly Ile Pro Ser Leu Glu Val Leu Thr Arg Lys Ala Ile Ala
        290                 295                 300

Leu Leu Asp Ala Arg Ala Arg Gln Lys Gly Ala Gly Lys Gly Phe Phe
305                 310                 315                 320

Leu Gln Val Glu Gly Ala Ala Ile Asp Lys Gln Asn His Asp Ala Asp
                325                 330                 335

Pro Cys Gly Gln Ile Gly Glu Thr Val Ala Phe Asp Arg Ala Val Lys
                340                 345                 350

Ala Ala Arg Glu Tyr Ala Ala Arg His Pro Asp Thr Leu Val Ile Thr
            355                 360                 365

Thr Ala Asp His Gly His Ser Ser Gln Ile Val Pro Met Ala Ala Arg
        370                 375                 380

Pro Ala Gly Leu Ser Ala Thr Leu Ile Thr Asp Glu Gly Ala Pro Met
385                 390                 395                 400

Lys Val Ser Tyr Ala Thr His Ala Gly Glu Glu Gly Gln Glu His Ser
                405                 410                 415
```

```
Gly Val Gln Val Arg Ile Ala Ala Glu Gly Pro Glu Ala His Arg Val
            420                 425                 430

Leu Gly Thr Thr Asp Gln Thr Gln Leu Phe Thr Thr Leu Arg Ile Gly
        435                 440                 445

Leu Asn Leu Arg
    450

<210> SEQ ID NO 22
<211> LENGTH: 860
<212> TYPE: PRT
<213> ORGANISM: Streptomyces sp.

<400> SEQUENCE: 22

Met Arg Arg Ala Gly Arg Arg Val Pro Gly Phe Ser Gly Glu Gly
1               5                   10                  15

Gly Ile Gly Lys Thr Ala Leu Leu Asp Glu Ile Gln Ala Met Ala Ala
                20                  25                  30

Asp Arg Cys Thr Val Trp Ser Gly Arg Gly Gly Glu Thr Val Thr Ser
            35                  40                  45

Val Pro Phe His Val Val Arg Gln Leu Leu Gln Pro Ala Leu Asp Gln
50                  55                  60

Phe Pro Pro Asp Glu Thr Arg Ala Leu Phe Gly Asp Trp Phe Glu Ile
65                  70                  75                  80

Ile Ala Pro Ala Leu Gly Leu Ala Glu Pro Ser Gly Pro Gln Pro Asp
                85                  90                  95

Pro Gln Gly Val Arg Asp Gly Leu Asp Tyr Val Val Gly Arg Leu Ala
            100                 105                 110

Ser Arg Leu Ser His Arg Pro Leu Leu Ile Val Asp Asp Ala His
            115                 120                 125

Trp Ala Asp Gly Glu Ser Leu Ala Trp Leu Ala Ser Phe Thr Ala Arg
130                 135                 140

Leu Gly Glu Leu Pro Val Leu Val Val Gln Ala His Arg Pro Gln Glu
145                 150                 155                 160

Met Ala Glu Arg Asn Ala Gly Tyr Val Ala Asp Arg Ala Ala Glu Arg
                165                 170                 175

Asp Ser His Gly Gln Glu Lys Val Thr Arg Val Ala Leu Arg Ala Leu
            180                 185                 190

Thr Pro Asp Ala Thr Ala Val Leu Val Arg Ser Ala Leu Gly Glu His
        195                 200                 205

Ala Asp Asp Pro Phe Cys Arg Glu Val Trp Ala Val Thr Gly Gly Asn
210                 215                 220

Pro Tyr Glu Ala Val Glu Leu Val Ala Lys Val Gln Asp His Glu Leu
225                 230                 235                 240

Pro Pro Val Glu Glu Ser Ala Gly Glu Leu Arg Ala Leu Gly Ala Ser
                245                 250                 255

Ala Arg Gly Ser Gly Leu Val Ala Arg Leu Glu Arg Leu Gly Thr Asn
            260                 265                 270

Ala Asn Arg Phe Ala Trp Ala Ala Val Leu Gly Thr Asp Ile Ser
            275                 280                 285

Gln Glu Leu Ala Ala Thr Leu Ala Gly Met Ser Pro Ala Glu Ala Ala
    290                 295                 300

Asp Cys Thr Ala Arg Leu Arg Asp Ala Arg Ile Val Ser Gly Phe Asp
305                 310                 315                 320

Pro Leu Glu Phe Val His Pro Leu Ile Ala Ser Ala Val Tyr Arg Ser
                325                 330                 335
```

```
Ile Pro Ser Ala Thr Arg Thr Ala Met His Gly Arg Ala Ala Trp Ala
            340                 345                 350

Ile Thr Arg Ala Gly Leu Gly Pro Ala Ala Ser Arg His Leu Leu
            355                 360                 365

Glu Val His Pro Asp Asp Gln Glu Leu Val Ala Gln Leu Arg Glu
            370                 375                 380

Ala Ala Arg Gln His Leu Ala Val Gly Ala Pro Glu Ala Ala Arg Arg
385                 390                 395                 400

Cys Leu Glu Arg Ala Leu Glu Glu Pro Pro Arg Pro Lys Asp Arg Ala
            405                 410                 415

Ala Leu Leu Tyr Glu Leu Gly Cys Ala Thr Leu Leu Ser Ser Pro Pro
            420                 425                 430

Thr Thr Val Gln His Leu Arg Ala Ala Leu Asp Met Pro Gly Leu Asp
            435                 440                 445

Asp Gly Leu Arg Val Asp Ala Thr Phe Arg Leu Ala Ala Ala Leu Ala
450                 455                 460

His Asn Asn Gln Leu Lys Glu Ala Ala Leu Ala Leu Ala Ala Glu Ala
465                 470                 475                 480

Ala Arg Thr Asp Pro Gly Pro Gly Leu Met Arg Leu Gln Ala Ala His
            485                 490                 495

Phe Met Trp Glu Gly Met Gln Ala Val Glu Asp Asp Gly Pro Thr Arg
            500                 505                 510

Ser Arg Arg Leu Thr Arg Asn Ala Asp His Leu Lys Gly Arg Asp Asn
            515                 520                 525

Ala Glu Arg Ala Leu Leu Thr Leu Arg Ala Phe Asp Gly Met Leu Arg
            530                 535                 540

Gly Glu Asn Ala Gln Leu Ile Val Asp Leu Cys Glu Arg Ala Leu Val
545                 550                 555                 560

Asp Gly Ser Pro Ala Arg Gly Leu Gly Trp Thr Asp Thr Glu Trp Gly
            565                 570                 575

Phe Glu Leu Pro Thr Met Val Gly Ile Thr Tyr Ser Phe Val Asp Gln
            580                 585                 590

Leu Asp Arg Ala Glu Ser Leu Phe Gly Glu Ala Val Arg Ala Phe Glu
            595                 600                 605

Ile Ser Gly Trp Ser Gly Ala His Leu Ala Phe Ala His Thr Leu Leu
            610                 615                 620

Gly Met Val His Arg Arg Gly Arg Leu Ala Glu Ala Glu Gly Phe
625                 630                 635                 640

Leu Arg Glu Gly Leu Arg Leu Ala Asp Arg Val Gly Ser Gly Leu Pro
            645                 650                 655

Val His Trp Asp Ala Thr Cys Leu Leu Ile Asp Thr Leu Leu Ala Arg
            660                 665                 670

Gly Arg Thr Glu Glu Ala Arg Ser Ile Ala Asp Arg Tyr His Phe Gly
            675                 680                 685

Pro Pro Tyr Pro Ser Ala Met Val Leu Pro Asp Gly Pro Cys Ile Arg
            690                 695                 700

Gly Arg Leu Leu Leu Ala Glu Gly Arg Thr Lys Glu Ala Ile Ala Glu
705                 710                 715                 720

Leu Glu Ala Ala Gly Ala Ala Leu Glu Ala Arg Glu Arg Phe Asn Gly
            725                 730                 735

Ile Trp Ala Pro Trp Ala Ala Asp Leu Ala Arg Ala Leu Val Asp Glu
            740                 745                 750
```

```
Asp Pro Ala Arg Ala Ala His Leu Ala Ala Arg Asn Arg Val His Ala
    755             760             765

Glu Arg Leu Gly Thr Pro Thr Ala Met Gly Glu Ala Leu Arg Cys Val
    770             775             780

Ala Leu Phe Ala Pro Pro Glu Arg Ser Ala Glu Leu Leu Ala Glu Ala
785             790             795                 800

Val Gly His Leu Glu Lys Ser Thr Ser Gly Tyr Glu His Ala Leu Ala
            805             810                 815

Arg Phe Glu Tyr Gly Ala Ala Ile Gly Ser His Arg Glu Leu Ala Arg
            820             825             830

Ala Gln Lys Gln Ala Met Thr Cys Gly Ala Glu Gly Leu Ala Ala Arg
        835             840             845

Ala Gln Gln Ala Arg Ala Ser Ile Arg Ser Ser Glu
850             855             860
```

METABOLIC ENGINEERING OF VIOMYCIN BIOSYNTHESIS

CROSS REFERENCE TO RELATED APPLICATIONS

This application claims the benefit of U.S. Provisional Application No. 60/496,760 filed Aug. 21, 2003, which is incorporated herein by reference to the extent not inconsistent herewith.

GOVERNMENT SUPPORT

This invention was made with United States government support USDA/CSREES 03-CRHF-0-6055. The United States government has certain rights in the invention.

FIELD OF INVENTION

The invention relates to antibiotic production and more specifically relates to the gene cluster responsible for viomycin antibiotic production and resistance. Materials of the invention have utility in transforming cells to produce various tuberactinomycins, derivatives thereof, and novel compounds useful in the preparation of biologically active compounds.

BACKGROUND OF THE INVENTION

It was recently estimated that between the years 1998 and 2030 there will be 225 million new cases of tuberculosis (TB) and 79 million TB-related deaths (Murray, C. J. L., and J. A. Salomon, 1998). These numbers are astonishing considering that treatments for this disease, in the forms of vaccines or chemotherapy, have been available for more than 50 years (Kramnik, I., et al., 2000). *Mycobacterium tuberculosis*, the causative agent of TB, is notoriously slow-growing and, during infection, can persist in a latent form in many individuals. These attributes contribute to the reasons why typical chemotherapy regimens for TB last 6-9 months (Bloom, B. R., and J. D. McKinney, 1999) and why TB is so persistent. This prolonged treatment presents significant hurdles in developing new antibiotics and in retaining the efficacy of currently used antibiotics. Side effects and toxicity from a particular compound can be magnified when a patient takes a drug for this length of time, and there are increased incidences of poor adherence to the chemotherapy regimen by unmonitored patients, resulting in the development of multidrug-resistant TB (MDR-TB) infections. These facts, together with alarming interactions between HIV and TB infections that can result in increased numbers of infected individuals and MDR-TB (Dye, C., et al., 2002; Gupta, R., et al., 2001; Lawn, S. D., et al., 2002; Barnes, P. F., et al., 1991; Bloom, B. R., and C. J. Murray, 1992), make it of paramount importance to develop new chemotherapy agents or introduce modifications to current agents to reduce toxicity and increase activity against MDR-TB.

One of the earliest antibiotics developed for the treatment of a bacterial infection was streptomycin, and its initial (and continued) use was for the treatment of tuberculosis (TB), the clinical manifestation of a *M. tuberculosis* infection. For over 50 years additional antibiotics and a vaccine have been developed to fight this infection. However, despite these developments this organism remains a significant human health concern.

Currently, the successful treatment of TB typically requires the simultaneous use of at least three drugs. These drugs are grouped into "first-line" and "second-line" antibiotics. The first-line drugs (e.g. streptomycin) are used first because they are less toxic and less expensive. It has been recommended that the second-line drugs (including viomycin, tuberactinomycins and capreomycins) be reserved specifically for the treatment of MDR-TB (Croft, J., et al., 1997). Use of the second-line drugs is increasing because resistance to many, if not all, of first-line drugs is increasing (Frieden, T. R., et al., 1993; Goble, M., et al., 1993), and it has been proposed that MDR-TB will soon be the norm (Davies, J. 1996). It has, however, been more than 25 years since a new drug to combat TB has been introduced (Duncan, K., and J. C. Sacchettini, 2000). Thus there is a continuing need in the art for the identification of antibiotics useful for the treatment of TB and particularly MDR-TB.

The tuberactinomycin family (TUBs) of antibiotics, including viomycin (VIO), tuberactinomycins (TUBs), capreomycins (CAPs) and tuberactinamines (FIG. 1) are a family of cyclic peptide natural products that are important second-line antibiotics for the treatment of MDR-TB. In fact, certain TUBs are included on the World Health Organization's "List of Essential Medicines" because of their anti-MDR-TB activity (WHO, 2002). Initial interest in the tuberactinomycins stemmed from the observation that VIO, the first tuberactinomycin to be isolated (Bartz, Q. R., et al., 1951; Ehrlich, J., et al., 1951; Finlay, A. C., et al., 1951), had the unusual property of having higher antimicrobial activity against mycobacterial species than against other bacteria (Ehrlich, J., et al., 1951; Finlay, A. C., et al., 1951; Marsh, W. S., et al., 1953 U.S. Pat No. 2,633,445; Mayer, R. L., et al., 1954). Importantly, VIO was active against strains of *M. tuberculosis* that were resistant to streptomycin (Hobby, G. L., et al., 1953). More recently, TUBs (Nagata, A., et al., 1968) and CAPs (Herr, E. B. J., et al., 1962 U.S. Pat. No. 3,143,168) were found to share a similar spectrum of antimicrobial activity with VIO. Currently, TUB N (FIG. 1) is used in Asia for the treatment of *M. tuberculosis* (Tsukamura, M., et al., 1989) and *M. avium* complex (Shigeto, E., et al., 2001) infections, while the CAPs are used in combination with other anti-TB drugs to treat MDR-TB (Goble, M. 1994).

New TUB derivatives are needed to combat the ever-expanding mycobacterial resistance to these drugs. A recent study analyzing 46 different strains of *M. tuberculosis* from TB patients found that 10% of these strains were resistant to CAP (Fattorini, L., et al., 1999). The continued spread of resistance without the development of new therapeutic alternatives will be devastating for patients who have limited options for treatment. It has recently been reported that 15 of 158 TB patients required treatment with CAP because the use of the standard aminoglycosides (amikacin, kanamycin, or streptomycin) was not appropriate (Tahaoglu, K., et al., 2001). Without the option of CAP, these patients would face an uncertain future.

In addition to their historical use in treating TB, the TUBs and analogs thereof have become lead compounds for use in treating other bacterial infections such as vancomycin-resistant enterococci and methicillin-resistant *Staphylococcus aureus* (Dirlam, J. P., et al., 1997; Linde II, R. G., et al., 1997; Lyssikatos, J. P., et al., 1997), and in targeting catalytic RNAs to disrupt viral replication (Jenne, A., et al., 2001; Rogers, J., et al., 1996; Schroeder, R., et al., 2000; von Ahsen, U., et al., 1991; Wank, H., et al., 1994; Wank, H., and R. Schroeder, 1996). In these cases, the TUBs are also considered important as the starting compounds for the development of more potent drugs.

Tuberactinomycins are reported to inhibit group I intron RNA splicing at high concentrations (Wank, H., et al., 1994). At subinhibitory concentrations, they are reported to stimulate oligomerization of group I intron RNA and intermolecular reactions (Wank, H., and R. Schroeder, 1996). The former finding is of interest for targeting group I introns in pathogenic microorganisms, since this type of intron is not found in humans (Hermann, T., and E. Westhof, 1998). The latter finding is of interest for developing therapeutic ribozymes that can fix mutated RNAs involved in inherited diseases (James, H. A., and I. Gibson, 1998).

TUBs are also reported to inhibit the human hepatitis delta virus ribozyme (Rogers, J., et al., 1996), and recently it was reported that VIO binds to subdomains IIIe/f of the hepatitis C virus (HCV) internal ribosome entry site, blocking HCV translation (Vos, S., et al., 2002). These studies indicate that derivatives of tuberactinomycins will be useful as antiviral agents.

Recent studies using TUB derivatives for the treatment of infections by the animal pathogen *Pasteurella haemolytica* and the human pathogens vancomycin-resistant enterococci and methicillin-resistant *Staphylococcus aureus* (Dirlam, J. P., et al., 1997; Linde II, R. G., et al., 1997; Lyssikatos, J. P., et al., 1997) found that modifications to the cyclic pentapeptide core of TUBs could enhance their activity against these pathogens. This work extends earlier findings that chemical modifications of these antibiotics can extend their use to non-mycobacterial bacteria (Kitagawa, T., et al., 1979, 1976, 1975; Wakamiya et al., 1977). Thus, new TUB derivatives are likely candidate drugs for the treatment of other bacterial infections.

New antibiotics and variants or derivatives of known antibiotics can be obtained by screening of natural sources, by manipulation of biosynthetic pathways in antibiotic producing organisms or by a combination of biosynthesis and chemical synthesis.

Gene Clusters

The study of the biosynthesis of natural products has made significant advancements in recent years due to the understanding that bacteria cluster the genes encoding all the enzymes involved in the biosynthesis of a particular natural product into one region of its genome (Chater, K. F., and C. J. Bruton. 1985; Du, L., et al., 2000; van Wageningen, A. M. A., et al., 1998). Analysis of this sequence allows a researcher to develop testable models for how the necessary precursors are synthesized, condensed, and modified to generate the final metabolite. In addition to the basic understanding of how a compound is biosynthesized, this information has the ability to direct metabolic engineering of the pathway to generate previously unattainable structural diversity in the metabolite of interest. This approach can be used to transform the developmental process of new pharmaceutically and agriculturally important compounds.

Chater and Bruton (1985) recognized that genes conferring resistance to, as well as controlling regulation and production of, methylenomycin are clustered in *S. violaceus-ruber* and *S. coelicolor*. The close linkage between the gene conferring resistance to the antibiotic and the other genes involved in biosynthesis of the antibiotic provides the basis for isolating an antibiotic cluster if the gene conferring antibiotic resistance is known.

Subsequent studies have confirmed that genes that confer resistance to an antibiotic and genes involved in the biosynthesis of that antibiotic, including penicillin, cephalosporin and cephamycins, and associated secondary metabolites, are organized in clusters. (Martin, 1992; See review by Martin and Liras, 1989). These biosynthetic clusters typically contain at least one pathway-specific regulatory gene and at least one resistance gene. U.S. Pat. No. 4,935,340 (Baltz et al., Method of Isolating Antibiotic Biosynthetic Genes, 1990) reports a method for identifying and isolating an antibiotic biosynthetic gene via hybridization with a labeled antibiotic resistance-conferring gene. This method relies on the fact that the majority of antibiotic biosynthetic genes from antibiotic-producing organisms are linked to antibiotic resistance-conferring genes. In particular, Baltz et al. used the erythromycin resistance-conferring gene to identify erythromycin biosynthetic genes via their hybridization method. In addition, they identified a recombinant vector that encoded erythromycin biosynthesis to drive erythromycin expression in a host (*Streptomyces lividans* TK23) that when untransformed produced no measurable amount of erythromycin.

A biosynthetic gene cluster for vancomycin group antibiotics was identified from *Amycolatopsis orientalis* (van Wageningen et al. 1997). In particular, 39 putative genes spanning 72 kb of contiguous DNA, including genes encoding for chloroeremomycin biosynthesis, were identified. Other antibiotic gene clusters that have been identified include those for rifamycin (August et al., 1998. Chem Biol. 5:69-70), tetracenomycin (Guilfoile & Hutchinson, 1992, Journal of Bacteriology, 174: 3651 & 3659) and actinorhodin (Caballero et al, 1991, Mol Gen Genet., 228: 372-80).

The mitomycin biosynthetic gene cluster was recently isolated and characterized from *S. iavendulae* (Sherman et al., U.S. Pat No. 6,495,348). The mitomycin gene cluster contains 47 mitomycin biosynthetic genes spanning 55 kb of contiguous DNA. These genes include those which encode for polypeptides which function to generate precursor molecules, such as those for mitosane ring system assembly, and those to functionalize sites on the core mitosane ring system. U.S. Pat. No. 6,495,348 and others (see e.g. Chater; U.S. Pat. No. 4,935,340), report that genes that encode enzymes for natural product assembly, including antibiotic production, are clustered on the *Streptomyces* genome. Furthermore, genes associated with antibiotic resistance (mrt and mrd) were located within the mitomycin gene cluster. This is consistent with previous studies that indicated antibiotic biosynthetic gene clusters typically contain one or more genes that confer antibiotic protection (Seno and Baltz, 1989).

By disrupting a repressor gene, mitomycin production in *S. Iavendulae* is reported to increase several-fold (U.S. Pat No. 6,495,348). *E. coli* were transformed to co-express MRD and MCT, the mitomycin-resistance conferring proteins, so that transformed cells had a high level of resistance to mitomycin. This resistance was mediated by increased mitomycin export out of the cell. Thus, as in Baltz et al., the use of antibiotic biosynthetic clusters in expression cassettes can be used to drive expression of antibiotics in host cells that normally do not produce measurable quantities of the antibiotic, and to increase the production and yield for cells that normally produce the antibiotic.

Organisms that do not naturally produce a particular biological product can be transformed with biosynthetic genes to produce that biological product. This is exemplified in U.S. Pat. No. 6,391,583 (Hutchinson et al., Method of Producing Antihypercholesterolemic Agents, 2002), where increased production of a cholesterol lowering compound, lovastatin, in both lovastatin-producing and non-lovastatin-producing producing organisms, was disclosed using a cluster of 17 genes from a native-lovastatin-producing strain of bacteria (*A. terreus*). By inactivating certain genes contained within the lovastatin cluster, different HMG-CoA reductase inhibitors were generated in the host organism. By mutating certain genes it was possible to prevent lovastatin production. By introducing extra copies of other genes into *A. terreus*, it was possible to increase lovastatin production up to 7-fold. Introducing the entire lovastatin-cluster into a normally non-lovastatin producing cell can result in lovastatin production in the cell.

These studies show that it is well known in the art to use gene clusters to affect production of a biologically active product, including increasing production in a native producer, abolishing production of the biologically active product, and forcing production of the biologically active product in a host cell that normally does not produce the biologically active product. It is also known that by selectively inactivating certain genes by mutation, or transforming a host cell with only certain genes, it is possible to selectively generate particular precursors of the biologically active product, which themselves can be biologically active, and to generate novel derivatives of these precursors. In addition, directed biosynthesis wherein an alternative precursor is applied to these transformed cells can be utilized to manufacture novel antibiotics.

Thus, there is a continuing need in the art for identification and isolation of antibiotic biosynthetic genes, including genes that result in enhanced production of antibiotics and confer resistance to antibiotics. Understanding the antibiotic's biosynthetic pathway also allows novel antibiotics to be manufactured biosynthetically.

Chemical Variants

It is also known in the art that individual precursors of antibiotics can be isolated and purified from a transformed cell culture, and chemically modified to generate novel derivatives thereof. This is a semi-synthetic method of synthesis. In addition, it is well known in the art that altering fermentation conditions can alter antibiotic production and provide useful starting points for the production of new semi-synthetic antibiotics. Gastaldo L, and Marinelli F. Microbiology. 2003 June; 149(Pt 6):1523-32.

Such techniques involve a combination of biosynthetic and chemical techniques. For instance, it can be difficult to manufacture antibiotics solely by chemical means. However, isolating a precursor molecule produced biosynthetically in an organism permits the generation of novel analogs by chemical means. For example, Dirlam et al. (1997) modified a synthetic reaction reported by Momoto and Shiba (1977) that used ureido exchange reactions on tuberactinomycin N. 6a-(3',4'-dichlorophenylamino)capreomycin was prepared by treating capreomycin sulfate with a 40-fold excess of 3,4-dichloroaniline in 2 N HCl/dioxane at 65° C. for 4 hours. Phenyl urea analogs could be generated in a similar manner. Other analogs were generated by reduction of the C-6-C-6a double bond by use of triethylsilane in trifluoroacetic acid. The activity of these derivatives was measured by assaying for antibacterial activity in different bacteria.

In addition to C-6a aryl urea modification, C-19 modification to viomycin and β-lysine substitutions and modification by chemical means have been reported. Lyssikatos et al., 1997; Linde et al., 1997. Such chemical modification studies were conducted in the hope of identifying antibiotic derivatives with improved potency. The free amino groups of the β-lysine residue in viomycin have also been chemically modified (Kitagawa et al., 1976) in an effort to determine the importance of the β-lysine residue in VIO's antimicrobial activity. Wakamiya et al. (1977) disclosed the antimicrobial activity for various TUB analogs where different amino acids were attached to the free α-amino group of the α,β-diaminopropionic acid residue in TUB N.

The ability to chemically generate antibiotic derivatives is limited by the amount, variety and purity of the starting material. Thus, need in the art remains for the generation of novel, chemically-pure antibiotic derivatives to serve as templates for chemical modification to generate improved antibiotics.

SUMMARY OF THE INVENTION

The present invention provides isolated and purified nucleic acid molecules, e.g., DNA, comprising a viomycin biosynthetic gene cluster, a functional variant or a functional fragment thereof. More specifically, the invention provides isolated and purified nucleic acid molecules comprising the viomycin gene cluster including one or more genes which confer resistance to viomycin.

Another embodiment is an isolated and purified nucleic acid molecule comprising at least a functional fragment of viomycin gene cluster whose nucleic acid sequence encodes at least one gene product of a vioA, vioB, vioC, vioD, vioE, vioF, vioG, vioH, vioI, vioJ, vioK, vioL, vioM, vioN, vioO, vioP, vioQ, vioR, vioS or vioT gene. Isolated and purified nucleic acid molecules of this invention include those which encode at least two gene products selected from the group consisting of a vioA, vioB, vioC, vioD, vioE, vioF, vioG, vioH, vioI, vioJ, vioK, vioL, vioM, vioN, vioO, vioP, vioQ, vioR, vioS or vioT gene product. Isolated and purified nucleic acid molecules of this invention include those which encode at least three gene products selected from the group consisting of a vioA, vioB, vioC, vioD, vioE, vioF, vioG, vioH, vioI, vioJ, vioK, vioL, vioM, vioN, vioO, vioP, vioQ, vioR, vioS or vioT gene product. Isolated and purified nucleic acid molecules of this invention include those which encode at least four gene products selected from the group consisting of a vioA, vioB, vioC, vioD, vioE, vioF, vioG, vioH, vioI, vioJ, vioK, vioL, vioM, vioN, vioO, vioP, vioQ, vioR, vioS or vioT gene product. Isolated and purified nucleic acid molecules of this invention include those which encode at least five gene products selected from the group consisting of a vioA, vioB, vioC, vioD, vioE, vioF, vioG, vioH, vioI, vioJ, vioK, vioL, vioM, vioN, vioO, vioP, vioQ, vioR, vioS or vioT gene product. Isolated and purified nucleic acid molecules of this invention include those which encode at least the vioC and vioD gene products. Isolated and purified nucleic acid molecules of this invention include those which encode at least the vioC and vioD gene products and further encode one or more gene products selected from the group consisting of a vioA, vioB, vioE, vioF, vioG, vioH, vioI, vioJ, vioK, vioL, vioM, vioN, vioO, vioP, vioQ, vioR, vioS or vioT gene product. Isolated and purified nucleic acid molecules of this invention include those which encode at least the vioM, vioN, vioO and vioP gene products. Isolated and purified nucleic acid molecules of this invention include those which encode at least the vioM, vioN, vioO and vioP gene products.and further encode one or more gene products selected from the group consisting of a vioA, vioB, vioC, vioD, vioE, vioF, vioG, vioH, vioI, vioJ, vioK, vioL, vioQ, vioR, vioS or vioT gene product. Any isolated and purified nucleic acid molecules of this invention can in addition encode one or more genes which function for resistance to an antibiotic, particularly one or more genes which function for resistance to viomycin.

The isolated and purified nucleic acid molecule can also encode the gene products of vioB, vioC, vioD, vioG and one or more of the gene products of a vioA, vioE, vioF, vioH, vioI, vioJ, vioK, vioL, vioM, vioN, vioO, vioP, vioQ, vioR, vioS or vioT gene.

The isolated and purified nucleic acid molecules of the invention can also comprise a nucleic acid sequence that encodes one or more of the proteins of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22. The isolated and purified nucleic acid molecules of the invention can also comprise a nucleic acid sequence that encodes two or more of the proteins of SEQ ID NO:2-Seq ID NO:22. The isolated and purified nucleic acid molecules of the invention can also comprise a nucleic acid sequence that encodes three or more of the proteins of SEQ ID NO:2-Seq ID NO:22. The isolated and purified nucleic acid molecules of the invention can also comprise a nucleic acid sequence that encodes four or more of the proteins of SEQ ID NO:2-Seq ID NO:22. The isolated and purified nucleic acid molecules of the invention can also comprise a nucleic acid sequence that encodes five or more of the proteins of SEQ ID NO:2-Seq ID NO:22. In general the isolated and purified nucleic acid molecules of the invention can comprise a nucleic acid sequence that encodes any combination of the proteins VioA, VioB, VioC, VioD, VioE, VioF, VioG, VioH, VioI, VioJ, VioK, VioL, vVoM, VioN, VioO, VioP, VioQ, VioR, VioS or VioT. In general the isolated and purified nucleic acid molecules of the invention can comprise a nucleic acid sequence that encodes any combination of the proteins of SEQ ID NO:2-SEQ ID NO:22.

One embodiment of the present invention is an isolated and purified nucleic acid molecule comprising a functional fragment of a viomycin gene cluster whose nucleic acid sequence has at least 80% sequence identity with one or more of vioA (SEQ ID NO:1, from 415 to 6786), vioB (SEQ ID NO:1, from 6981 to 8021), vioC (SEQ ID NO:1, from 8018 to 9094), vioD (SEQ ID NO:1, from 9091 to 10260), vioE (SEQ ID NO:1, from 10257 to 11600), vioF (SEQ ID NO:1, from 11597 to 14818), vioG (SEQ ID NO:1, from 14908 to 18174), vioH (SEQ ID NO:1, from 18171 to 18959), vioI (SEQ ID NO:1, from 18956 to 20608), vioJ (SEQ ID NO:1, from 20605 to 21777), vioK (SEQ ID NO:1, from 21827 to 22909), vioL (SEQ ID NO:1, from 22906 to 23832), vioM (SEQ ID NO:1, from 23829 to 25202), vioN (SEQ ID NO:1, from 25199 to 25390), vioO (SEQ ID NO:1, from 25396 to 27228), vioP (SEQ ID NO:1, from 27303 to 28640), vioQ (SEQ ID NO:1, from 29590 to 30621), vioR (SEQ ID NO:1, from 31370 to 30660), vioS (SEQ ID NO:1, from 31752 to 33110), or vioT(SEQ ID NO:1, from 36299 to 33717).

Another embodiment is an isolated and purified nucleic acid molecule comprising a functional fragment of a viomycin gene cluster whose nucleic acid sequence has at least 80% sequence identity withone or more of vioA (SEQ ID NO:1, from 415 to 6786), vioE (SEQ ID NO:1, from 10257 to 11600), vioF (SEQ ID NO:1, from 11597 to 14818), vioH (SEQ ID NO:1, from 18171 to 18959), vioI (SEQ ID NO:1, from 18956 to 20608), vioJ (SEQ ID NO:1, from 20605 to 21777), vioK (SEQ ID NO:1, from 21827 to 22909), vioL (SEQ ID NO:1, from 22906 to 23832), vioM (SEQ ID NO:1, from 23829 to 25202), vioN (SEQ ID NO:1, from 25199 to 25390), vioO (SEQ ID NO:1, from 25396 to 27228), vioP (SEQ ID NO:1, from 27303 to 28640), vioQ (SEQ ID NO:1, from 29590 to 30621), vioR (SEQ ID NO:1, from 31370 to 30660), vioS (SEQ ID NO:1, from 31752 to 33110), or vioT(SEQ ID NO:1, from 36299 to 33717).

The isolated and purified nucleic acid molecules of the invention can also comprise SEQ ID NO:1 from 415 to 28640 and from 29590 to 36299, or a degenerate variant thereof.

Another embodiment of the isolated and purified nucleic acid molecules of the invention comprises SEQ ID NO:1 from 415 to 36299, or a degenerate variant thereof.

Isolated and purified nucleic acid molecules comprising functional gene combinations of individual genes within the viomycin gene cluster are included in the invention. One embodiment is an isolated and purified nucleic acid molecule which encodes the gene products of VioM, VioN, VioO and VioP genes. Another embodiment is an isolated and purified nucleic acid molecule which encodes the gene products of VioC and VioD genes.

The isolated and purified nucleic acid molecules of the invention can be obtained from any source that contains any one or more genes of the viomycin gene cluster. In particular, one or more genes of the viomycin gene cluster may be obtained from a strain of *Streptomyces*. It is preferred that the isolated and purified nucleic acid molecule of the invention is nucleic acid from *Streptomyces* sp. ATCC11861 (which is equivalently classified as *Streptomyces vinaecus*), *Streptomyces californicus*, or *Streptomyces olivoreticuli* subsp. *olivoreticuli*, although isolated and purified nucleic acid molecules from other organisms which produce viomycin, or biological or functional equivalents thereof, are also within the scope of the invention. More preferably the isolated and purified nucleic acid molecule of the invention is nucleic acid from *Streptomyces* sp. ATCC11861. The nucleic acid molecules of the invention are double-stranded or single-stranded.

The invention also relates to nucleic acid molecules which comprise the nucleic acid sequence complementary to the sequence of one or more genes of the viomycin biosynthetic gene cluster.

The nucleic acid molecules of the invention also comprise the viomycin gene cluster wherein genes within the cluster, alone or in combination with other genes within the cluster, are absent or disrupted. One embodiment is a nucleic acid molecule comprising at least a functional fragment of a viomycin gene cluster wherein one or more of the vioA, vioB, vioC, vioD, vioE, vioF, vioG, vioH, vioI, vioJ, vioK, vioL, vioM, vioN, vioO, vioP, vioQ, vioR, vioS or vioT genes is absent or disrupted. Another embodiment is a nucleic acid molecule comprising at least a functional fragment of a viomycin gene cluster wherein one or more of the vioA, vioB, vioC, vioD, vioE, vioF, vioG, vioH, vioI, vioJ, vioK, vioL, vioM, vioN, vioO, vioP, vioQ, vioR, vioS or vioT genes has been mutated such that the gene product of the mutated gene is not functional. Another embodiment is a nucleic acid molecule comprising at least a functional fragment of a viomycin gene cluster wherein the entire coding sequence or a portion thereof of one or more of the vioA, vioB, vioC, vioD, vioE, vioF, vioG, vioH, vioI, vioJ, vioK, vioL, vioM, vioN, vioO, vioP, vioQ, vioR, vioS or vioT genes is absent. Another embodiment is a nucleic acid molecule comprising at least a functional fragment of a viomycin biosynthetic gene cluster wherein the gene encoding VioB, VioC, VioD, VioK, VioL, VioM, VioN, VioO, VioP, VioQ or any combination thereof are absent or disrupted. The absent or disrupted gene combinations in the nucleic acid molecule can be, among others, those encoding: VioC and VioD; VioM, VioN, VioO and VioP; VioQ; VioL;

VioM, VioN, VioO, VioP and VioQ; VioM, VioN, VioO, VioP and VioL; VioM, VioN, VioO, VioP, VioQ and VioL; VioQ and VioL.

The isolated and purified nucleic acid molecule of the invention can comprise a sequence encoding the gene product of the vioO gene. The nucleic acid sequence can also encode each of the twenty gene product genes (vioA through vioN, vioP through vioT, and vph) in addition to encoding the gene product of the VioO gene.

The adenylation domain (A domain) in any one or more of the genes in the viomycin gene cluster encoding nonribosomal peptide synthetase (NRPS) that generate the cyclic pentapeptide core of viomycin (or a derivate or precursor thereof can be replaced by A domains from noncognate systems, resulting in a nucleic acid that encodes one or more gene products (altered from those of the native gene cluster) that activate and add alternative amino acids to the cyclic pentapeptide core of viomycin (or a derivative or precursor thereof). Thus, in one embodiment, the invention comprises nucleic acid molecules in which the VioO adenylation domain is replaced with an adenylation domain from a noncognate system. The VioO adenylation domain replacement can encode an A domain for activation and attachment of L-Leucine, L-Phenylalanine, L-Tyrosine or L-Histidine. Replacing the VioO A domain by the A domain of pltF or redM are other embodiments. Other adenylation domains that can be replaced are vioG (capreomycidine-specific A domain) are vioF (2,3-diaminopropionate-specific A domain.)

The invention comprises methods for preparing biologically active agents or pharmaceutically acceptable salts thereof. These methods comprise transforming a host cell with one or more nucleic acid molecules of this invention, culturing the transformed host cell in a culture medium containing assimilable sources of carbon, nitrogen and inorganic salts under aerobic fermentation conditions so as to yield an increase in a biologically active agent relative to the level of the biologically active agent produced by a corresponding untransformed host cell.

Each isolated and purified nucleic acid molecule of the invention which comprises at least a functional fragment of a viomycin biosynthetic gene cluster can be introduced into a host cell for the expression of one or more gene products. One or more of the coding sequences (those sequences encoding the gene products) of the viomycin biosynthetic gene cluster can be operably linked to and under the regulatory control of one or more heterologous regulatory sequences (i.e., regulatory sequences which are not those operably linked to the coding sequence in the viomycin biosynthetic gene cluster.) In an embodiment, the invention provides isolated and purified nucleic acid sequences which comprise one or more of such heterologous regulatory sequences operably linked to one or more of the coding sequences of a gene of the viomycin biosynthetic gene cluster. The nucleic acid molecules of the invention can, in addition to one or more sequences which encode a gene product (i.e., coding sequences), contain one or more regulatory sequences operationally linked to the coding sequences. The invention also includes isolated and purified nucleic acid sequences comprising one or more of the regulatory sequences of the viomycin biosynthetic gene cluster. The invention further includes isolated and purified nucleic acid sequences comprising one or more of the regulatory sequences of the viomycin biosynthetic gene cluster in combination with one or more heterologous coding sequences (coding sequences which are not operably linked to the regulatory sequences in the viomycin biosynthetic gene cluster) operably linked to the one or more regulatory sequences of the viomycin biosynthetic gene cluster.

An embodiment of the invention is a method for preparing a biologically active agent or pharmaceutically acceptable salt thereof comprising transforming a host cell with nucleic acid molecule encoding at least a functional fragment of a viomycin gene cluster, and culturing the transformed host cell in a culture medium containing assimilable sources of carbon, nitrogen and inorganic salts under aerobic fermentation conditions so as to yield an increase in a biologically active agent relative to the level of the biologically active agent produced by a corresponding untransformed host cell.

In another embodiment, a biologically active agent is prepared by transforming a host cell with a functional fragment of the viomycin gene cluster that encodes the gene products of vioM, vioN, vioO and vioP genes, and culturing the transformed host cell in a culture medium containing assimilable sources of carbon, nitrogen and inorganic salts under aerobic fermentation conditions so as to yield an increase in a biologically active agent relative to the level of the biologically active agent produced by a corresponding untransformed host cell.

Another method of the invention is preparing a biologically active agent by transfroming a host cell with a functional fragment of the viomycin gene cluster that encodes the gene products of vioC and vioD genes, and culturing the transformed host cell in a culture medium containing assimilable sources of carbon, nitrogen and inorganic salts under aerobic fermentation conditions so as to yield an increase in a biologically active agent relative to the level of the biologically active agent produced by a corresponding untransformed host cell.

An embodiment of the invention is a method for preparing a biologically active agent by transforming a host cell with the viomycin gene cluster wherein the gene encoding the gene products of vioB, vioC, vioD, vioK, vioL, vioM, vioN, vioO and vioP, or vioQ genes, or any combination thereof, are absent or disrupted, and culturing the transformed host cell in a culture medium containing assimilable sources of carbon, nitrogen, inorganic salts and supplemented with one or more alternative amino acids under aerobic fermentation conditions so as to yield an increase in a biologically active agent relative to the level of the biologically active agent produced by a corresponding untransformed host cell.

In another embodiment, a biologically active agent is prepared by transforming a host cell with a functional fragment of the viomycin gene cluster that encodes the gene product of a vioO gene whose A domain has been replaced with an A domain from a noncognate system and culturing the transformed host cell in a culture medium containing assimilable sources of carbon, nitrogen and inorganic salts under aerobic fermentation conditions so as to yield an increase in a biologically active agent relative to the level of the biologically active agent produced by a corresponding untransformed host cell.

The host cell can also be transformed with a functional fragment of the viomycin gene cluster that encodes the gene product of a vioO gene whose A domain has been replaced with an A domain from a noncognate system and one or more gene product of a vioA, vioB, vioC, vioD, vioE, vioF, vioG, vioH, vioI, vioJ, vioK, vioL, vioM, vioN, vioP, vioQ, vioR, vioS, vioT or vph gene, or any combination thereof. The transformed host cell is cultured in a culture medium containing assimilable sources of carbon, nitrogen and inorganic salts under aerobic fermentation conditions so as to yield an increase in a biologically active agent relative to the level of the biologically active agent produced by a corresponding untransformed host cell.

The host cell for these methods is any cell that can be transformed with the isolated and purified nucleic acid molecules of the invention. The host cell can be a VIO-producing organism or a non-VIO-producing organism. Preferably, the host cell is *E. coli, Saccharothrix mutabilis* subsp. *capreolus*, or *Streptomyces sp.* ATCC11861. Host cells most generally include any eukaryotic or prokaryotic cells.

The invention also provides functional isolated and purified gene products, polypeptides or proteins encoded by a viomycin biosynthetic gene cluster. In one embodiment the isolated and purified polypeptide, or functional fragment thereof, has an amino acid sequence selected from the group consisting of VioA (SEQ ID NO:2), VioB (SEQ ID NO:3), VioC (SEQ ID NO:4), VioD (SEQ ID NO:5), VioE (SEQ ID NO:6), VioF (SEQ ID NO:7), VioG (SEQ ID NO:8), VioH (SEQ ID NO:9), VioI (SEQ ID NO:10), VioJ (SEQ ID NO:11), VioK (SEQ ID NO:12), VioL (SEQ ID NO:13), VioM (SEQ ID NO:14), VioN (SEQ ID NO:15), VioO (SEQ ID NO:16), VioP (SEQ ID NO:17), VioQ (SEQ ID NO:19), VioR (SEQ ID NO:20), VioS (SEQ ID NO:21) and VioT (SEQ ID NO:22).

In another embodiment the isolated and purified polypeptide, or functional fragment thereof, has an amino acid sequence selected from the group consisting of VioA (SEQ ID NO:2), VioE (SEQ ID NO:6), VioF (SEQ ID NO:7), VioH (SEQ ID NO:9), VioI (SEQ ID NO:10), VioJ (SEQ ID NO:11), VioK (SEQ ID NO:12), VioL (SEQ ID NO:13), VioM (SEQ ID NO:14), VioN (SEQ ID NO:15), VioO (SEQ ID NO:16), VioP (SEQ ID NO:17), VioQ (SEQ ID NO:19), VioR (SEQ ID NO:20), VioS (SEQ ID NO:21) and VioT (SEQ ID NO:22).

Another embodiment of the present invention is an expression cassette comprising a nucleic acid molecule of the invention that is operably linked to a promoter functional in a host cell. In one embodiment the nucleic acid molecule in the expression cassette is at least a functional fragment of a viomycin biosynthetic gene cluster. The expression cassette is also pBAC-VIO-Conj.

The invention includes recombinant host cells comprising any one or more of the nucleic acid molecules of the invention. The host cell is preferably a bacterial cell. The invention is also biologically active agents or pharmaceutically acceptable salts thereof produced by recombinant host cells of the invention that are not produced by a corresponding nonrecombinant host cell. These biologically active agents are preferably an antibiotic, an antibiotic precursor, or a molecule involved in the chemical or biosynthetic production of an antibiotic. The biologically active agent can be a TUB family derivative. The biologically active agent can also not be a TUB family derivative.

A recombinant host cell of the invention is one in which viomycin production by the recombinant cell is increased relative to viomycin production in a corresponding nonrecombinant host cell. An additional embodiment is a recombinant host cell of the invention wherein viomycin production is less than the corresponding production in a corresponding nonrecombinant host cell.

A recombinant host cell of the invention is also a host cell that contains the nucleic acid molecule that encodes for the gene products of VioM, VioN, VioO and VioP genes. The host cell can be *Saccharothrix mutabilis* subsp. *capreolus*.

Another embodiment is a recombinant host cell wherein the nucleic acid molecule of the invention contained in the host cell encodes for the gene product of VioC and VioD genes. The host cell can be *E. Coli*.

The recombinant host cell of the invention is also a host cell that contains the nucleic acid molecule encoding the viomycin gene cluster wherein the gene encoding VioB, VioC, VioD, VioK, VioL, VioM, VioN, VioO, VioP, VioQ or any combination thereof are absent or disrupted.

Another embodiment is a recombinant host cell containing a gene encoding a VioO gene product whose A domain has been replaced with an adenylation domain from a noncognate cell. The recombinant host cell encoding this altered VioO gene product can also encode one or more of the other gene products: VioA - VioN, VioP -VioT, or any combination thereof.

DETAILED DESCRIPTION OF THE INVENTION

Definitions

Through cloning and sequencing of the viomycin gene cluster, nucleic acid molecules, as well as nucleic acid molecules in expression cassettes and recombinant host cells, useful in the production of antibiotics, antibiotic precursors and novel antibiotics and antibiotic derivatives are obtained. In addition, useful molecules encoded by the viomycin biosynthetic gene cluster are obtained.

As used herein, "antibiotic" is a substance produced by a microorganism which, either naturally or with chemical modification, will inhibit the growth of or kill another microorganism or eukaryotic cell. Viomycin and other members of the TUB family are of particular interest. As used herein, the "TUB family" includes tuberactinomycins (TUB), viomycin (VIO), tuberactinamines and capreomycins (CAPs) (see FIG. 1).

Figure 8:
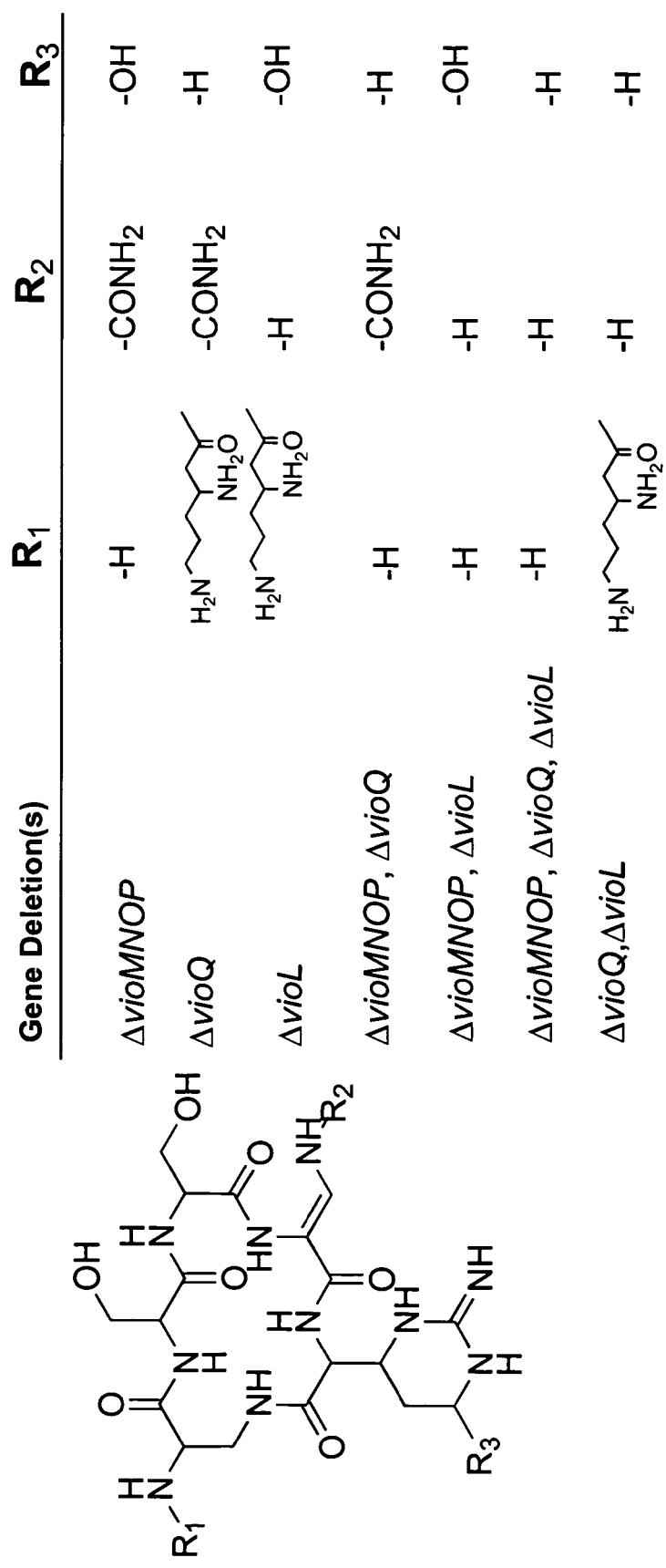
FIG. 8. Is a scheme providing examples of tuberactinomycin derivatives that can be generated by gene deletions in the viomycin biosynthetic gene cluster.

"Derivative" as used herein means that a particular compound is modified chemically or biochemically so that it comprises other chemical moieties, e.g. TUB family derivatives are generated by manipulating the viomycin gene cluster such that different moieties attach to the cyclic pentapeptide core. Derivative can also include compounds with variant cyclic pentapeptide cores. FIG. 8 illustrates some examples of derivatives.

As used herein "TUB family derivative" includes "viomycin derivative," "tuberactinamine derivative," "tuberactinomycin derivative" and "capreomycin derivative." Derivatives of particular interest are biologically active molecules, particularly having antibiotic activity, or useful starting molecules, precursors for the semisynthetic generation of antibiotics. Derivatives include molecules that have different moieties attached to the viomycin cyclic pentapeptide core. Derivatives also include compounds having one or more different amino acids in the cyclic pentapeptide cores.

An "antibiotic biosynthetic gene" is a nucleic acid, e.g. DNA, segment or sequence that encodes a step in the process of converting primary metabolites into antibiotics. Encodes refers to a polypeptide or protein amino acid sequnece being defined by a DNA sequence. A gene is a portion of DNA that is involved in producing a polypeptide chain or protein; it can include regions preceeding and following the coding DNA a well as introns between exons. A gene encodes a corresponding gene product.

An "antibiotic resistance-conferring gene" is a nucleic acid segment that encodes an enzymatic or other activity which alone or in combination with other gene products, confers resistance to an antibiotic.

"Antibiotic gene cluster" includes the entire set of antibiotic biosynthetic genes necessary for the process of converting primary metabolites into antibiotics and any antibiotic resistance conferring genes needed to protect the host organism from the detrimental effects of the antibiotic being produced, as well as regulatory, export and activation genes. "Antibiotic biosynthetic gene cluster" includes the entire set of biosynthetic genes necessary for the process of converting primary metabolites into antibiotics, including sequences encoding enzymes necessary for antibiotic synthesis, including sequences that encode enzymes for precursor formation, as well as regulatory, export, activation, but excludes sequences encoding resistance to viomycin As used herein, the "viomycin gene cluster" includes sequences encoding enzymes necessary for viomycin synthesis, including sequences that encode enzymes for precursor formation, assembly of the cyclic pentapeptide core, modifications to the cyclic pentapeptide, as well as regulatory, export, activation and resistance to viomycin. As used herein, the "viomycin biosynthetic gene cluster" includes sequences encoding enzymes necessary for viomycin synthesis, including sequences that encode enzymes for precursor formation, assembly of the cyclic pentapeptide core, modifications to the cyclic pentapeptide, as well as regulatory, export, activation, but excludes sequences encoding resistance to viomycin.

"Antibiotic-producing organisms" include any organism including, but not limited to, *Streptomyces sp*, which produces an antibiotic. This definition encompasses organisms that naturally produce viomycin. "VIO-producing organisms" include cells that naturally produce viomycin or cells that are genetically manipulated to produce viomycin.

"Non-VIO-producing organisms" include organisms that naturally in the absence of genetic manipulation do not produce significantly measurable quantities of viomycin. This can include cells that may produce useful compounds related to VIO, such as the capreomycin producer *Saccharothrix mutabilis* subsp. *capreolus*, or a normally VIO-producing cell such as *Streptomyces* sp. that is genetically manipulated to not produce VIO, or a strain such as a *Streptomyces* that contains the VIO cluster but does not produce the viomycin because the necessary gene products are not expressed.

A "host cell" is any cell into which the nucleic acid molecules of this invention can be introduced and expressed to produce gene products and/or biologically active agents, or the naturally occurring genes have been altered to produce altered gene products or biologically active agents. The host cell may naturally contain one or more of the viomycin genes of this invention. In this case the introduction of the isolated and purified nucleic acid molecules of this invention into the host causes a measurable change in the gene products and/or biologically active agents compared to the wild-type host cell. A "recombinant" host cell of the invention has a genome that has been artificially manipulated in vitro to add, delete, mutate, excise, one or more genes or parts thereof. A "nonrecombinant host cell" is a wild-type cell whose genome is unaltered. A recombinant host cell of the invention is particularly useful in generating one or more biologically active agents.

Using one or more of the nucleotide sequences of the invention, viomycin production in a wide range of host cells can be manipulated. For example, viomycin production can be either increased or prevented in cells. Alternatively, by inactivating particular genes in the viomycin gene cluster, a host cell can also be manipulated to produce an antibiotic precursor, a particular member of the TUB family or novel derivatives thereof. Host cells that have been modified genetically (recombinant host cells), include host cells comprising an expression cassette of the invention, or host cells in which the genome has been genetically manipulated, e.g., by deletion of a portion of, replacement of a portion of, or by disruption of, the host chromosome, so as to reduce, eliminate or modify the expression of a particular viomycin biosynthetic gene of the invention.

One embodiment of the invention is a recombinant host cell, e.g. a bacterial cell and particularly a *Streptomyces* cell, in which a portion of a nucleic acid sequence comprising the viomycin gene cluster, i.e., the endogenous or native genomic sequence, is absent, disrupted or replaced, for example, by an insertion with heterologous sequences or substituted with a variant nucleic acid sequence of the invention, preferably so as to result in altered viomycin synthesis, such as an increase in viomycin production, and/or production of a novel compound. Absent and disrupted are used broadly herein to encompass any technique that results in decreased or absent gene product or gene activity. It can include gene mutation at one or more sites within a gene, and/or excising one or more genes or parts thereof. FIG. 8 provides examples of various disruptions to genes within the VIO cluster to produce non-VIO compounds in host cells that normally produce VIO. A given nucleic acid sequence may contain one or more of such disruptions or replacements in a gene or genes of the viomycin cluster.

Host cells useful to prepare the recombinant host cells of the invention include cells which do not express or do not comprise nucleic acid corresponding to the nucleic acid molecules of the invention, e.g., viomycin biosynthetic genes, including the CAP-producing strain *Saccharothrix mutabilis* subsp. *capreolus* (ATCC23892), *Streptomyces lividans, E. coli*, as well as cells that naturally produce viomycin including *Streptomyces* sp. (ATCC11861), *Streptomyces californicus*. (ATCC3312), and *Streptomyces olivoreticulis* subsp. *olivoreticuli* (ATCC 23943) (also called *Streptomyces abikoensis*).

For example, the genes that encode VioM, VioN, VioO and VioP can be moved into, and expressed in, *Saccharothrix mutabilis* subsp. *capreolus* to add a β-lysine moiety onto residue 1 of the CAP antibiotics to produce capreomycin derivatives.

The term "biologically active agent" is used broadly herein to encompass any functional gene product or expression product generated directly or indirectly from the nucleic acid molecules of this invention. It can be among others an end-product antibiotic, an antibiotic precursor or an enzyme useful in the production of antibiotics. An antibiotic precursor is a substrate or intermediate involved in the biosynthesis of downstream end-product antibiotics.

The biologically active agent can be generated as cationic or anionic species. The invention encompasses pharmaceutically acceptable salts of such cationic and anionic species.

Suitable pharmaceutically acceptable salts include salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

"Genetic manipulation" or "genetic engineering" are used very broadly to encompass any means of altering the expression of one or more genes in the gene cluster so as to produce a measurable, phenotypic change. The term includes augmenting a non-VIO-producing host genome with one or more of the VIO genes or a VIO-producing host genome to overexpress one or more genes of the VIO cluster. The VIO cluster can be introduced into a host cell in whole or in part. Genes within the cluster can be inactivated, specifically by any kind of mutation, including in-frame deletions, insertion, or random mutagenesis. Genetic material can be introduced into the host cell by any known means in the art as described hereinbelow.

As used herein, the terms "isolated and/or purified" refer to in vitro isolation of a RNA, DNA or polypeptide molecule from its natural cellular environment, and from association with other components of the cell, such as nucleic acid or polypeptide, so that it can be sequenced, replicated and/or expressed.

An "isolated and purified nucleic acid molecule" is a nucleic acid the structure of which is not identical to that of any naturally occurring nucleic acid. This term covers, for example, DNA which has part of the sequence of a naturally occurring genomic DNA, but does not have the flanking portions of DNA found in the naturally occurring genome. The term also includes, for example, a nucleic acid incorporated in a vector or into the genome of a cell such that the resulting molecule is not identical to any naturally occurring vector or genomic DNA.

Some protein and nucleic acid sequence variation is tolerated without loss of function. In fact, some nucleic acid and protein sequence variation is expected and understood in the art, without substantially affecting protein function.

A variant nucleic acid sequence of the invention has at least about 80%, more preferably at least about 90%, and even more preferably at least about 95%, but less than 100%, contiguous nucleic acid sequence identity to a nucleic acid sequence comprising SEQ ID NO:1, the individual genes of SEQ ID NO:1 (see Table 1), or a fragment thereof. However, these nucleic acid sequences still encode a functional gene product. The amino acid and/or nucleic acid similarity (or homology) of two sequences can be determined manually or using computer algorithms well known to the art.

The present invention further includes isolated and purified DNA sequences which hybridize under standard or stringent conditions to the nucleic acid molecules of the invention. Hybridization procedures are useful for identifying polynucleotides with sufficient homology to the subject sequences to be useful as taught herein. The particular hybridization techniques are not essential to the subject invention. As improvements are made in hybridization techniques, they can be readily applied by one of ordinary skill in the art.

Preferably, the isolated nucleic acid molecule comprising the gene cluster includes a nucleic acid sequence comprising the sequence given in SEQ ID NO:1, a variant or a fragment thereof, e.g., a nucleic acid molecule that hybridizes under moderate, or more preferably stringent, hybridization conditions to the sequence given in SEQ ID NO:1 or a fragment thereof. Isolated nucleic acid molecules which hybridize under moderate or more preferably stringent conditions to the sequence of SEQ ID NO:1 or a functional fragment thereof can include nucleic acid of a *Streptomyces* strain or particularly a VIO-producing *Streptomyces* strain. In addition, the particular order of the genes contained in the Vio gene cluster can vary.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example in Keller, G. H., M. M. Manak (1987) *DNA Probes*, Stockton Press, New York, N.Y., pp. 169-170, hereby incorporated by reference. For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5 times Denhardt's solution, sonicated salmon sperm DNA (50 µg/ml), 0.1% sodium dodecylsulfate (SDS), and 10% dextran sulfate at 4° C., with washes at 42° C. in 0.2×SSC and 0.1% SDS.

An example of high stringency conditions is hybridizing at 68° C. in 5× SSC/5× Denhardt's solution/0.1% SDS, and washing in 0.2× SSC/0.1% SDS at room temperature. An example of conditions of moderate stringency is hybridizing at 68° C. in 5× SSC/5× Denhardt's solution/0.1% SDS and washing at 42° C. in 3× SSC. The parameters of temperature and salt concentration can be varied to achieve the desired level of sequence identity between probe and target nucleic acid. See, e.g., Sambrook et al. (1989) supra or Ausubel et al. (1995) *Current Protocols in Molecular Biology*, John Wiley & Sons, NY, N.Y., for further guidance on hybridization conditions.

In general, salt and/or temperature can be altered to change stringency. With a labeled DNA fragment >70 or so bases in length, the following conditions can be used: Low, 1 or 2× SSPE, room temperature; Low, 1 or 2× SSPE, 42° C.; Moderate, 0.2× or 1× SSPE, 65° C.; and High, 0.1× SSPE, 65° C.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'. This invention encompasses complementary sequences to any of the nucleotide sequences claimed in this invention.

A "fragment of a nucleic acid" is a partial sequence of the nucleic acid molecule such that the resultant polypeptide encoded by the fragment remains functional as determined by, for instance, a measurable amount of enzymatic activity. A fragment can also be useful as a probe or a primer for diagnosis, sequencing or cloning of the viomycin cluster. A "functional fragment" of a nucleic acid molecule encodes and can express a functional gene product. A functional gene product from such a fragment retains a measurable level of activity of the gene product encoded by the full nucleic acid from which the fragment is derived. For example, a functional fragment of a VioA gene encodes a gene product (protein) which retains any measurable function and activity of the VioA gene product (protein). Functional gene products of this invention include one or more of the gene products VioA through VioT, or functional variants or fragments thereof. These functional gene products include functional enzymes, functional transporters, functional transcriptional regulators and polypeptides and proteins that function in antibiotic resistance. Thus, a vio gene encodes a Vio gene product. A fragment of nucleic acid of a vio gene encodes a fragment of a Vio gene product. A functional fragment of nucleic acid of a vio gene encodes a functional Vio gene product.

The term "sequence homology" or "sequence identity" means the proportion of base matches between two nucleic acid sequences or the proportion of amino acid matches between two amino acid sequences. When sequence homology is expressed as a percentage, e.g., 50%, the percentage denotes the fraction of matches over the length of sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

"Similarity," when comparing two amino acid sequences, encompasses amino acids that are "identical" and amino acids whose side groups have similar properties (eg. basic, polar, etc). "Identical" or "identity" only encompasses amino acids that are identical.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 6 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 this volume, pp. 1-10. The two sequences or parts thereof are more preferably homologous if their amino acids are greater than or equal to 50% identical when optimally aligned using the ALIGN program.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence can be a subset of a larger sequence, for example, as a segment of a full-length cDNA or gene sequence given in a sequence listing, or can comprise a complete cDNA or gene sequence. Generally, a reference sequence is at least 20 nucleotides in length, frequently at least 25 nucleotides in length, and often at least 50 nucleotides in length. Since two polynucleotides can each (1) comprise a sequence (i.e., a portion of the complete polynucleotide sequence) that is similar between the two polynucleotides, and (2) can further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window can comprise additions or deletions (i.e., gaps) of 20 percent or less as compared to the reference sequence (which does not comprise additions or deletions) for optimal alignment of the two sequences. Optimal alignment of sequences for aligning a comparison window can be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc; Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C., G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide when optimally aligned, such as by the programs GAP or BESTFIT using default gap weights, comprises a sequence that has at least 80 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides. The percentage of sequence identity is calculated by comparing the reference sequence to the polynucleotide sequence which can include deletions or additions which total 20 percent or less of the reference sequence over the window of comparison.

Nucleotide Sequence Variation

The present invention contemplates nucleic acid sequences which hybridize under low, moderate or high stringency hybridization conditions to the exemplified nucleic acid sequences set forth herein. Thus, nucleic acid sequences encoding variant polypeptides, i.e., those having at least one amino acid substitution, insertion, addition or deletion, or nucleic acid sequences having conservative (e.g., silent) nucleotide substitutions, are within the scope of the invention. Preferably, variant polypeptides encoded by the nucleic acid sequences of the invention are biologically active. The present invention also contemplates naturally occurring allelic variations and mutations of the nucleic acid sequences described herein.

Duplex formation and stability depend on substantial complementarity between the two strands of a hybrid, and, as noted above, a certain degree of mismatch can be tolerated. Therefore, the sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan. Other methods may become known in the future.

These variants can be used in the same manner as the exemplified sequences so long as the variants have substantial sequence homology with the original sequence. As used herein, substantial sequence homology refers to homology sufficient to enable the variant polynucleotide to function in the same capacity as the polynucleotide from which the variant was derived. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage.

As is well known in the art, because of the degeneracy of the genetic code, there are numerous other DNA and RNA molecules that can code for the same polypeptides as those encoded by the exemplified biosynthetic genes and fragments thereof. DNA and RNA molecules that have different genetic codes, but encode identical polypeptides, are called "degenerate variants." The present invention, therefore, contemplates those other DNA and RNA molecules which, on expression, encode the polypeptides of, for example, portions of SEQ. ID NOs:2-22. Having identified the amino acid residue sequence encoded by a viomycin biosynthetic gene, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid, are within the scope of this invention.

The 20 common amino acids and their representative abbreviations, symbols and codons are well known in the art (see, for example, Molecular Biology of the Cell, Second Edition, B. Alberts et al., Garland Publishing Inc., New York and London, 1989). As is also well known in the art, codons constitute triplet sequences of nucleotides in mRNA molecules and as such, are characterized by the base uracil (U) in place of base thymidine (T) which is present in DNA molecules. A simple change in a codon for the same amino acid residue within a polynucleotide will not change the structure of the encoded polypeptide. By way of example, it can be seen from SEQ. ID NO:1 that a GAA codon for glutamic acid exists at nucleotide positions 418-420. However, glutamic acid can be encoded by a GAG codon. Substitution of the GAG codon with a GM codon, or vice versa, does not alter the fact that glutamic acid is placed at that location; nor does that substitution substantially alter the DNA sequence of SEQ ID NO:1. Such a substitution results in production of the same polypeptide. In a similar manner, substitutions of the recited codons with other equivalent codons can be made in a like manner without departing from the scope of the present invention.

A nucleic acid molecule, segment or sequence of the present invention can also be an RNA molecule, segment or sequence. An RNA molecule contemplated by the present invention corresponds to, is complementary to or hybridizes under low, moderate or high stringency conditions to, any of the DNA sequences set forth herein. Exemplary and preferred RNA molecules are mRNA molecules that comprise at least one viomycin biosynthetic gene of this invention.

Mutations can be made to the native nucleic acid sequences of the invention and such mutants used in place of the native sequence, so long as the mutants are able to function with other sequences to collectively catalyze the synthesis of an identifiable TUB. Such mutations can be made to the native sequences using conventional techniques such as by preparing synthetic oligonucleotides including the mutations and inserting the mutated sequence into the gene using restriction endonuclease digestion. (See, e.g., Kunkel, T. A. Proc, Natl. Acad. Sci. USA (1985) 82:448; Geisselsoder et al. BioTechniques (1987) 5:786). Alternatively, the mutations can be effected using a mismatched primer (generally 10-30 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al., Proc. Natl. Acad. Sci. USA (1982) 79:6409. PCR mutagenesis will also find use for effecting the desired mutations. Alternatively, in frame deletions can be used (Kieser et al., 2000ab).

Random mutagenesis of the nucleotide sequence can be accomplished by several different techniques known in the art, such as by altering sequences within restriction endonuclease sites, inserting an oligonucleotide linker randomly into a plasmid, by irradiation with X-rays or ultravioLet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Protein Sequence Variation

Variation in the protein sequence of SEQ ID NOs:2-22 is expected. Proteins can also retain function even after deletion of one or both ends of the protein. Tolerance is also permitted in the precise start and stop locations of the genes encoding functionally equivalent polypeptides. Some adjacent genes can overlap, while others do not. In addition, one or more conservative amino acid substitutions will not substantially affect protein function. Non-conservative amino acid substitutions in regions of the protein that are not functional will not substantially affect protein function.

A preferred functional variant polypeptide includes a variant polypeptide or functional fragment thereof having at least about 1%, more preferably at least about 10%, and even more preferably at least about 50% of the activity of the polypeptide having the amino acid sequence comprising one of the encoded polypeptides of SEQ ID NOs:2-22. For example, the activity of a polypeptide of SEQ ID NO:17 (vioP) can be compared to a variant polypeptide of SEQ ID NO:17 having at least one amino acid substitution, insertion, or deletion relative to SEQ ID NO:17. Variant polypeptides are "substantially functionally equivalent" to the polypeptides in this invention (SEQ ID NOs:2-22), if the variant has at least about 1% the biological activity of the corresponding non-variant polypeptide of this invention. More preferably, the variant polypeptide is "functionally equivalent" and has at least about 50% the biological activity of the corresponding non-variant polypeptide of this invention, more preferably 80% and greater and all subcombinations between.

Similar to nucleotide sequences, the homology between two polypeptide sequences can be determined. Two proteins are substantially identical if they share 80% sequence identity, more preferably 90%, and more preferably at least about 95% or 99% sequence identity. Substantial identity also encompasses two sequences that have conservative amino acid substitutions, as described below. This invention comprises amino acid sequences that are functionally and substantially functionally equivalent to the amino acid sequences of this invention (SEQ ID NOs:2-22).

One or more of the residues of the polypeptides of the invention (SEQ ID NOs:2-22) can be altered, so long as the polypeptide variant is biologically active. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major affect on the properties of the resulting variant polypeptide. Whether an amino acid change results in a functional polypeptide can readily be determined by assaying the specific activity of the polypeptide variant.

Amino acid substitutions falling within the scope of the invention, are, in general, accomplished by selecting substitutions that do not differ significantly in their affect on maintaining (a) the structure of the peptide backbone in the area of the substitution, (b) the charge or hydrophobicity of the molecule at the target site, or (c) the bulk of the side chain.

The invention also encompasses polypeptide variants with non-conservative substitutions wherein the variant is functionally equivalent or substantially functionally equivalent to the native protein. Non-conservative substitutions entail exchanging a member of one of the classes described above for another.

Acid addition salts of the polypeptide or variant polypeptide or of amino residues of the polypeptide or variant polypeptide can be prepared by contacting the polypeptide or amine with one or more equivalents of the desired inorganic or organic acid, such as, for example, hydrochloric acid. Esters of carboxyl groups of the polypeptides can also be prepared by any of the usual methods known in the art.

In accordance with the present invention, there is provided a purified and isolated nucleic acid molecule which encodes the entire pathway for the biosynthesis of viomycin. Desirably, the nucleic acid molecule is a DNA isolated from Streptomyces sp. However, the cluster sequence can be isolated from other organisms. Alternatively the nucleic acids can be in whole or in part chemically synthesized by methods known in the art. Further nucleic acids isolated from natural sources can be ligated together using chemical means known in the art. As outlined hereinbelow (see Example 1), viomycin clusters from other organisms are obtained by isolating the organism's genomic DNA, partially digesting the DNA and packaging it into lambda phage to infect E. coli to generate a cosmid library. This library is screened for the presence of the viomycin resistance gene, vph, using, for example, Vph/FEco and VphREco primers. To ensure the entire cluster is located, a second screen using a primer for a different gene (e.g. VioG) in the cluster is performed. This second screen locates cosmids that contain the different gene but do not contain vph. Sequencing the plasmids identified by each of the screens permits a viomycin cluster to be identified. In such a manner viomycin clusters can be obtained from any organism, including organisms that contain silent viomycin biosynthetic genes and do not normally produce viomycin.

Further encompassed are nucleotide sequences for probes and primers to various portions of the gene cluster. Given a particular sequence, the generation of primers to that sequence is well known in the art. For example, because Streptomyces contain approximately 75% GC bases, cloning primers are generally 30 base pairs in length, with a 6 base pair restriction enzyme recognition site and 2 to 3 AT bases added on the end. Thus, for cloning primers, only 21 to 24 bases will be 100% identical to the sequence of interest. Sequencing and diagnostic primers are typically 20 to 28 base pairs, more preferably 24 base pairs in length, and generally match the sequence of interest between approximately 90% to 100%, most preferably approximately 100%. Primers are typically approximately 20 to 34 base pairs in length, more preferably 24 to 30 base pairs in length, with annealing temperatures in the 65 to 70° C. range. Gene probes are preferably approximately 1 kb in length comprising the gene of interest to be probed.

Vio biosynthetic clusters obtained from other strains of Streptomyces are not expected to have 100% identity with the cluster obtained from the ATCC11861 strain. For instance, functionally equivalent genes may not align in the genome in the same way. This is demonstrated in the glycopeptide antibiotics, where enzymes with equivalent functions have approximately 70% identity and 80% similarity between the various species. Pootoolal et al. (2002); van Wageningen et al. (1998); Pelzer et al., Antimicrob. Agents Chemother. 43(7), 1565-1573 (1999); Sosio et al., Chemistry & Biology 10(6), 541-9 (2003); Chiu et al., Proc. Natl. Acad. Sci 98(15), 8548-53 (2001). In addition, cph, the capreomycin resistance gene in Saccharothrix mutabilis subsp. capreolus, is functionally equivalent to vph, the viomycin resistance gene in Streptomyces sp., but these proteins only have 53% identity and 66% similarity. Another example is for the closest homologs to VioC and VioD, SttL and SttN from Streptomyces rochei, which have approximately 40% identity and 55% similarity to VioC and VioD. Thus, variation in the nucleotide sequence for Vio clusters obtained from other species is expected.

The stop/start points for each of the genes within the VIO cluster (SEQ ID NO:1) is given in Table 1. There is some tolerance in the exact start point of a given orf within the viomycin cluster. Many of the Streptomyces secondary metabolite gene clusters are proposed to be translationally coupled. The particular method by which the start location is determined is as follows. First, all ATG and GTG codons are assigned as possible start codons. Starting from the first ATG or GTG, the open reading frame is blastp, PSI-Blast, and RPS-Blast searched against the NCBI databank of proteins. Each of the homologs is analyzed for how closely the start codon aligns with the putative start of the Viomycin homolog. There may be conflicting results. For example, the start codons of VioS and VioR were revised and moved upstream based on the PSI-BLAST results finding many homologs with earlier potential start codons (VioR changed from 31397 to 31370; VioS changed from 31896 to 31752). However, there is still the possibility that the downstream codon is correct. Those of skill in the art understand and can take into account such uncertainty when practicing the methods of this invention. Without wishing to be bound to any particular theory, the predicted function of each gene contained within the isolated Vio cluster is given in Table 1.

TABLE 1

Summary of Genes and Predicted Encoded Functions:

| Gene | SEQ ID NO: | Start-Stop | Predicted Encoded Function |
|---|---|---|---|
| vioA | 2 | 415-6786 | NRPS (A-PCP-C-A-PCP-C)[a] |
| vioB | 3 | 6981-8021 | 2,3-diaminopropionate synthase |
| vioC | 4 | 8018-9094 | L-Arg hydroxylase |
| vioD | 5 | 9091-10260 | Capreomycidine synthase |
| vioE | 6 | 10257-11600 | Permease |
| vioF | 7 | 11597-14818 | NRPS (A-PCP-C) |
| vioG | 8 | 14908-18174 | NRPS (A-PCP-C/-?) |
| vioH | 9 | 18171-18959 | Type II thioesterase |
| vioI | 10 | 18956-20608 | NRPS (PCP-C) |
| vioJ | 11 | 20605-21777 | 2,3-diaminopropionyl α,β,-desaturase |
| vioK | 12 | 21827-22909 | Ornithine cyclodeaminase |
| vioL | 13 | 22906-23832 | Carbamoyltransferase |
| vioM | 14 | 23829-25202 | NRPS (C) - β-lysine transferase |
| vioN | 15 | 25199-25390 | MbtH homolog |
| vioO | 16 | 25396-27228 | NRPS (A-PCP) - β-lysine activation |
| vioP | 17 | 27303-28640 | Lysine 2,3-aminomutase |
| vph | 18 | 29557-28676 | Viomycin phosphotransferase |
| vioQ | 19 | 29590-30621 | Capreomycidine hydroxylase |
| vioR | 20 | 31370-30660 | Transcriptional regulator |
| vioS | 21 | 31752-33110 | Viomycin-phosphate phosphatase |
| vioT | 22 | 36299-33717 | Transcriptional Regulator |

[a]Abbreviations for NRPS domains: A, adenylation; PCP, peptidylcarrier protein; C, condensation; C/, truncated condensation; ?, domain of unknown function.

The compounds produced by the recombinant host cells of the invention are preferably biologically active agents such as end-product antibiotics, antibiotics or compounds useful in synthesis of other antibiotics, enzymes involved in antibiotic synthesis, inhibitors or alterers of catalytic RNA function, antiviral or crop protection agents. Alternatively, they can be useful starting points in further chemical synthesis procedures. Methods employing these compounds, e.g. to treat humans for MDR-TB, are also encompassed.

The invention described herein is useful for the production of TUB family antibiotics including, viomycin, analogs or derivatives thereof, or novel compounds. See, e.g. Thomas et al. 2003; Ju et al. 2004. Commercial chemical syntheses of viomycin is difficult. The gene cluster described herein contains all the genes required for the production of the TUB family of antibiotics. Thus, the isolated and purified nucleic acids of this invention are useful for the selective production of specific TUB antibiotics, the overproduction or underproduction of particular compounds, e.g., overproduction of certain TUB antibiotics, and the production of novel compounds, e.g., viomycin-derived compounds as well as the production of novel non-viomycin related compounds. For example, combinational biosynthetic-based modification of viomycin antibiotics can be accomplished by selective activation or disruption of specific genes within the cluster, or incorporation of the genes into biased biosynthetic libraries which are assayed for a wide range of biological activities, to derive greater chemical diversity in the viomycin. A further example includes the introduction of a viomycin biosynthetic gene(s) into a particular host cell so as to result in the production of a novel non-viomycin related compound due to the activity of the viomycin biosynthetic gene(s) on other metabolites, intermediates or components of the host cells. The in vitro expression of polypeptides from this gene cluster also provides an enzymatic route for the production of known TUB compounds that are produced in low quantities by untransformed cells, or conversion of currently available TUBs to other known or novel TUBs through semisynthetic procedures.

A novel TUB can be generated by manipulation of VioO (see FIG. 5), a protein consisting of two domains, for example. The N-terminal domain (consisting of amino acids 1-527) contains the adenylation (A) domain of VioO. This domain binds a specific amino acid (β-Lysine), activates β-Lysine to a β-Lysyl-AMP intermediate, and subsequently tethers the β-Lysyl moiety to the 4'-phosphopantetheinyl prosthetic group of the C-terminal peptidylcarrier protein (PCP) domain (amino acids 528-610). The A domain of VioO can be removed and replaced with an A domain from a noncognate system that activates alternative amino acids because of the didomain nature of the protein. As used herein "noncognate system" means a non-VioO protein that has a domain functionally equivalent to the A domain of VioO but that activates a different amino acid than that activated by VioO. An "alternative amino acid" is any amino acid that is not the one originally activated by the original A domain. Once constructed, these protein "chimeras" can function to add the alternative amino acid to the α-carbon of residue 1 of the cyclic pentapeptide core of viomycin (see FIG. 9).

For example, the plasmid pVioO-PCP2 is constructed to contain the portion of vioO encoding amino acids 528-610 (DNA sequence 26976-27228). To this sequence, an in-frame HindIII restriction site is added to the 5' end to allow for in-frame fusions of the PCP-encoding region of vioO with DNA encoding noncognate A domains. Thus, chimeric proteins can be produced that activate other amino acids besides β-Lysine for covalent attachment to the fused PCP domain of VioO. VioM can catalytically attach this alternative amino acid to residue 1 of the cyclic pentapeptide core of viomycin, generating a new TUB derivative.

Figure 9:
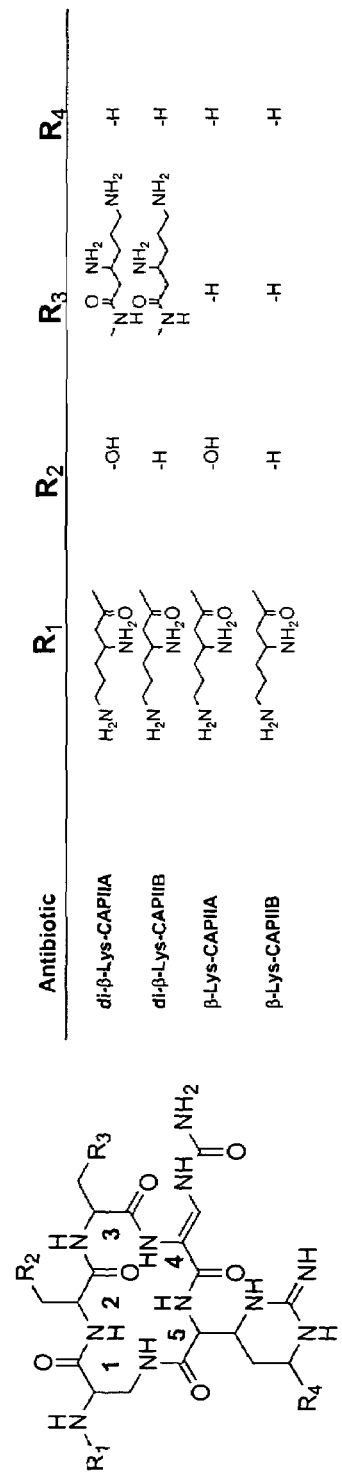
FIG. 9. (A) Exemplary chemical structures of capreomycin derivatives when VioO and VioM are incubated with the purified capreomycin antibiotics or, alternatively, when these two enzymes are produced in *Saccharothrix mutabilis* subsp. *capreolus*. (B) Exemplary chemical structures of tuberactinomycin derivatives generated when the chimeric enzyme containing the PlfF or RedM A domain fused to the VioO PCP domain reacts with VioM and the accepting substrates tuberactinamine A (TUA), capreomycin IA (CAPIA), capreomycin IB (CAPIB), capreomycin IIA (CAPIIA), and capreomycin IIB (CAPIIB).
Figure 9:
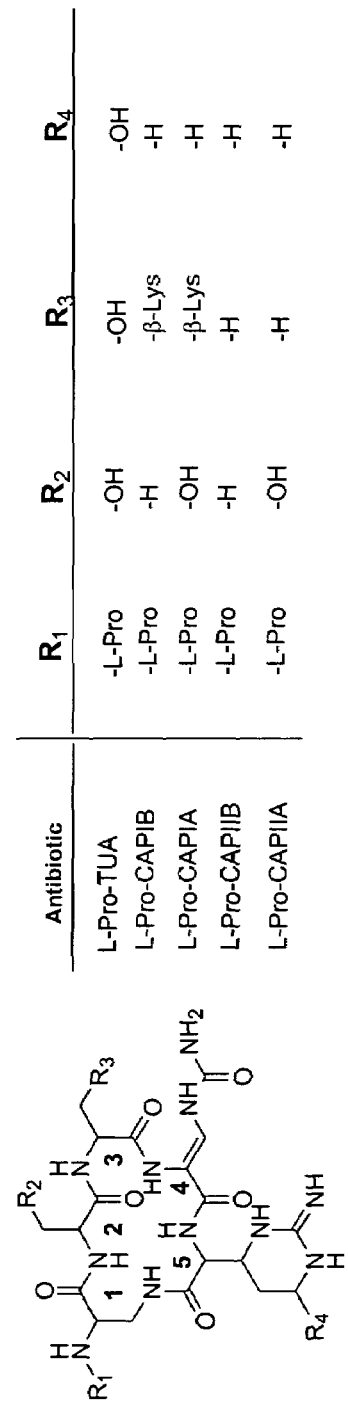

As examples, the pltF and redM genes from the pyoluteorin (Nowak-Thompson et al., 1999) and prodiginine (Cerdeno et al., 2001; Thomas et al., 2002) pathways, have been fused to the PCP portion of vioO, generating plasmids pPltF/VioOPCP2 and pRedM/VioOPCP2, respectively. PltF and redM each recognize and activate L-Proline (Thomas et al., 2002) and the resulting fusion proteins can catalyze the formation of L-Proline tethered to the PCP domain of the fusion protein. The tethered L-Prolyl moiety is subsequently transferred to the cyclic pentapeptide core of viomycin by VioM to form L-Prolyl-tuberactinamine A, a TUB derivative that has not been isolated or synthesized. FIG. 9 shows exemplary chemical structures of the types of antibiotics that can be generated when VioO is altered to have the PltF A domain replace the VioO A domain. The exemplary chemical structures of FIG. 9 can be generated by incubating the chimeric enzyme with the purified CAPs and tuberactinamine A, or when the chimeric enzyme along with VioM is produced in *Saccharothrix mutabilis* subsp *capreolus*.

As an extension of this, any A domain is a candidate for fusion to the PCP domain of VioO. For example, the first A domain of CepA activates L-Leucine (van Wageningen et al., 1998; Trauger et al., 2000) and can be introduced onto the PCP domain of VioO to generate L-Leucyl-tuberactinamine A. Other examples include the A domain from GrsA (Stachelhaus et al., 1995) or NovH (Steffensky et al., 2000; Chen and Walsh, 2001) that recognize and activate L-Phenylalanine or L-Tyrosine, respectively. The A domain of NikP1 (Bormann et al., 1996; Chen et al., 2002) can introduce L-Histidine to tuberactinamine A. The A domains used are not limited to bacterial A domains. For example, the gene encoding the A domain of Lys2 from *Saccharomyces cervi-* siae (Ehmann et al., 1999) can be fused to the PCP domain of VioO, or another such Vio protein, to alter the amino acid added. Such fusion with the PCP domain of VioO results in the formation of alpha-aminoadipate-tuberactinamine A.

In addition to generating tuberactinamine A derivatives with alternative amino acids replacing the β-Lysine moiety, these same chimeric genes can be introduced into *Saccharothrix mutabilis* subsp. *capreolus* to generate new derivatives of the CAP antibiotics.

Genetic engineering of the viomycin cluster in various host cells is particularly useful in directed biosynthesis experiments to generate particular antibiotics, including TUB family antibiotics and TUB family derivatives. Directed biosynthesis is well known to those skilled in the art. See e.g. Hojati et al. (2002). Directed biosynthesis is the process of feeding an alternative precursor(s) to a strain for incorporation into the molecule of interest by displacing the natural precursor.

Using targeted gene disruption, the ability of *Streptomyces* sp. ATCC11861 to generate the three nonproteinogenic amino acid precursors (2,3-diaminopropionate, capreomycidine, and beta-lysine) can be abolished. Alternative amino acid analogs can then be fed to the mutant strain(s) for incorporation into the natural product.

Disruption of vioP (ΔvioP), the lysine 2,3-aminomutase, will eliminate beta-lysine production by *Streptomyces* sp. ATCC11861. To this strain, alternative beta amino acids (e.g. beta-alanine, beta-histidine, beta-homolysine, 3-aminobutyric acid, and other structural analogs) can be fed and the product analyzed for incorporation into the viomycin structure. In these cases, the beta-lysine moiety will be replaced by the alternative amino acid. The culture medium for such directed biosynthesis can be a viomycin production medium (Tam and Jordan, 1972) wherein the culture is grown under conditions established for viomycin production (Thomas et al., 2002) that has been supplemented with the alternative beta amino acid of interest. The supplement can be added either at the start of culture growth or when viomycin production typically begins (after approximately 5 days of growth) or any time between start of growth and start of viomycin production. Under optimized growth conditions, the *Streptomyces* sp. strain ATCC11861 ΔvioP culture with added beta-histidine, for example, produces beta-histidine-tuberactinamine A. Using the same protocol beta histidine can be replaced by a variety of beta amino acids to increase the diversity of antibiotics generated.

Disruption of vioB or vioK will abolish the production of 2,3-diaminopropionate. To these mutant strains, alternative diamino acids can be fed (e.g. 2,4-diaminobutyric acid, 2,3-diaminobutanoic acid, ornithine, and other structural analogs) and the product analyzed for incorporation into the viomycin peptide backbone. The deleted VioB strain of *Steptomyces* sp ATCC11861 grown under conditions for viomycin production, supplemented with 2,4-diaminobutyrate (DAB) resulted in the production of a new metabolite, possibly a novel tuberactinomycin antibiotic.

Disruption of vioC or vioD abolishes production of capreomycidine. To these mutant strains alternative aromatic amino acids can be fed (phenylglycine, 4-hydroxyphenylglycine, 4-fluorophenylglycine, 4-bromophenylglycine, 3,5-dihydroxyphenylglycine, and other structural analogs) and the product analyzed for incorporation into the viomycin peptide backbone. With VioC and VioD inactivated, competition between endogenous (2S,3R)-capreomycidine and the alternative precursor is eliminated thereby increasing the probability of incorporation of the alternative precursor into the molecule of interest.

These gene disruptions can be combined in concert with directed biosynthesis on multiple positions of the viomycin hexapeptide to generate novel antibiotics, TUB family antibiotics, derivatives thereof and precursor molecules.

The purified and isolated viomycin biosynthetic genes are useful to elucidate the molecular basis for the biosynthesis of viomycin, as well as to engineer the biosynthesis of novel natural products. For instance, host cells can be genetically manipulated to produce one or more specific members of the TUB family by using gene disruption techniques to disrupt particular genes within the viomycin biosynthetic cluster. Gene disruption techniques are well known in the art, see for example, Kieser et al., 2000ab, for one technique, in-frame deletions using a delivery vector. In addition, genetic engineering or overexpression of the transport, resistance and regulatory proteins can lead to higher titers of viomycin compounds and derivatives thereof from production cultures. The invention encompasses the isolation of any of these compounds from the production culture as a starting compound to chemically generate new antibiotics.

The polypeptides SEQ. ID NOs:2-17, 19-22 encoded by the viomycin gene cluster are useful as enzymes in producing novel derivatives of the TUB family as well as specific members of the TUB family. For instance, VioC (SEQ. ID NO:4) and VioD (SEQ ID NO:5) can be moved into a host cell, e.g. *E. coli*. The VioC and VioD can then be isolated and purified and used to produce (2S,3R)-capreomycidine in large scale amounts (Ju et al., 2004).

In addition, the antibiotics derived from the present invention are useful as starting material in semisynthetic processes to generate libraries of novel antibiotics. In a semisynthetic process host cells are transformed to produce a specific TUB family antibiotic. These specific antibiotics can then be chemically modified by methods well known in the art and screened to determine their efficacy against bacterial diseases, including drug resistant strains of TB.

The present isolated, biologically active purified polypeptides, variants or fragments thereof, can be further purified by well known techniques in the art, including fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography. These isolated polypeptides are useful as starting compounds or enzymes to generate particular antibiotics of the TUB family, and novel derivatives thereof.

Chimeric Expression Cassettes, Vectors and Host Cells of the Invention

As used herein, "chimeric" means that a vector comprises DNA from at least two different species, or comprises DNA from the same species, which is linked or associated in a manner which does not occur in the "native" or wild type of the species. The recombinant DNA sequence or segment, used for transformation herein, can be circular or linear, double-stranded or single-stranded. Generally, the DNA sequence or segment is in the form of chimeric DNA, such as plasmid DNA, that can also contain coding regions flanked by control sequences which promote the expression of the DNA present in the resultant transformed (recombinant) host cell. Aside from DNA sequences that serve as transcription units for the nucleic acid molecules of the invention or portions thereof, a portion of the DNA can be untranscribed, serving a regulatory or a structural function. For example, the preselected DNA can itself comprise a promoter that is active in a particular host cell.

Other elements functional in the host cells, such as introns, enhancers, polyadenylation sequences and the like, can also be a part of the DNA. Such elements may or may not be necessary for the function of the DNA, but may provide improved expression of the DNA by affecting transcription, stability of the mRNA, or the like. Such elements can be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers. Other regulatory sequences may also be desirable which allow for regulation of expression of the genes relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements can also be present in the vector, for example, enhancer sequences.

"Operably linked" means that the nucleic acids are placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The DNA to be introduced into the cells further will generally contain either a selectable marker gene or a reporter gene or both to facilitate identification and selection of transformed cells from the population of cells sought to be transformed. Alternatively, the selectable marker can be carried on a separate piece of DNA and used in a co-transformation procedure. Both selectable markers and reporter genes can be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Expression of the reporter gene is assayed at a suitable time after the DNA has been introduced into the recipient cells.

Prokaryotic expression systems are preferred, and in particular, systems compatible with Streptomyces sp. are of particular interest. Control elements for use in such systems include promoters, optionally containing operator sequences, and ribosome binding sites. Particularly useful promoters include control sequences derived from the gene clusters of the invention. Preferred promoters are Streptomyces promoters, including but not limited to the ermE, pika, and tipA promoters. Additional examples include promoter sequences derived from biosynthetic enzymes such as tryptophan (trp), the β-lactamase promoter system, bacteriophage lambda PL, and T5. In addition, synthetic promoters, such as the tac promoter (U.S. Pat. No. 4,551,433), which do not occur in nature, also function in bacterial host cells.

The various nucleic acid molecules of interest can be cloned into one or more recombinant vectors as individual cassettes, with separate control elements, or under the control of, e.g., a single promoter. The nucleic acid molecules can include flanking restriction sites to allow for the easy deletion and insertion of other sequences. The design of such unique restriction sites is known to those of skill in the art and can be accomplished using the techniques, such as site-directed mutagenesis and PCR.

For sequences generated by random mutagenesis, the choice of vector depends on the pool of mutant sequences, i.e., donor or recipient, with which they are to be employed. Furthermore, the choice of vector determines the host cell to be employed in subsequent steps of the claimed method. Any transducible cloning vector can be used as a cloning vector for the donor pool of mutants. It is preferred, however, that phagemids, cosmids, or similar cloning vectors be used for cloning the donor pool of mutant encoding nucleotide sequences into the host cell. Phagemids and cosmids, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted can be identical or can be constructed to harbor and express different genetic markers (see, e.g., Sambrook et al., supra). Vectors containing marker genes are useful to determine whether or not transfection is successful.

Thus, for example, the cloning vector employed can be an E. coli/Streptomyces shuttle vector (see, for example, U.S. Pat. Nos. 4,416,994, 4,343,906, 4,477,571, 4,362,816, and 4,340,674), a cosmid, a plasmid, a bacterial artificial chromosome (BAC) (see, e.g., Zhang and Wing, Plant Mol. Biol., 35, 115 (1997); Schalkwyk et al., Curr, Op. Biotech., 6, 37 (1995); and Monaco and Lavin, Trends in Biotech., 12, 280 (1994)), or a phagemid. The host cell can be a bacterial cell such as E. coli, Penicillium patulum, Saccharothrix mutabilis subsp. capreolus and Streptomyces spp. such as S. lividans, S. venezuelae, or S. Iavendulae, or a eukaryotic cell such as fungi, yeast or a plant cell, e.g., monocot and dicot cells, preferably cells that are regenerable.

One example of such a vector is the pBAC-VIO-Conj vector. The DraI to HindIII fragment of pVIO-P8C8RH (containing the viomycin biosynthetic cluster from vioA to the internal HindlII site of vioG) can be inserted between the HindlII and SfoI sites of pBeloBAC11 (Shizuya, H. et al. 1992 PNAS 89:8794-8797), generating plasmid pBelo-BAC11-vioA-G. Such an insert includes not only vioA-vioG but also ~20 kb of Streptomyces sp. ATCC11861 upstream of vioA.

The HindIII to HindIII fragment of pVIO-P2C3RG (containing the viomycin biosynthetic pathway from vioT to the internal HindIII fragment of vioG) is then inserted into the HindIII site of pBeloBAC11-vioA-G. Orientation can be determined by PCR amplification. The plasmid generated is pBAC-VIO. This clone also contains a small portion of SuperCos-1 (from Stratagene—Evans et al. 1989. Gene 79:9-20) in addition to ~20 kb of *Streptomyces* sp. ATCC11861 sequence upstream of vioT.

The pBAC-VIO vector is digested with XbaI (site lies between the repE and ori sites of pBAC-VIO) and blunt ended using Klenow. The DraI fragment from pOJ436 (Bierman et al. 1992 Gene 116:43-49) that contains the RK2 oriT, aac(3)IV apramycin resistance gene, attP ΦC31 integration site, and int ΦC31 integrase is inserted into this site. This results in the vector pBAC-VIO-conj.

This plasmid contains the entire viomycin biosynthetic gene cluster along with the ability to conjugate between *Escherichia coli* and *Streptomyces* species. Additionally the ΦC31 integration site and integrase enable the vector to integrate into the chromosome of various *Streptomyces* species including *Streptomyces lividans* and *Streptomyces coelicolor*.

The viomycin biosynthetic gene cluster-containing plasmid pBAC-VIO-Conj can be mobilized into a heterologous host (i.e. *Streptomyces coelicolor* M145, *Streptomyces coelicolor* CH999, *Streptomyces lividans* 1326) using standard conjugation procedures (Kieser, T., et al., 2000b). Exconjugants are selected for using apramycin. These strains contain the pBAC-VIO-Conj vector integrated into the attB site of the chromosome.

These strains can be grown in viomycin production medium (Tam and Jordan, 1972) or alternative media (i.e. Yeast extract malt extract medium) for heterologous expression of the viomycin biosynthetic pathway. Increased production of viomycin in the heterologous host may involve supplementing or changing the concentration of the medium with various amino acids at various times during culture, manipulating the salts contained in the medium or altering the media's pH. For example, supplementing the medium with precursors (i.e. L-serine, (2S)-arginine, L-lysine), increasing the expression of the transcriptional regulator VioR (i.e. vioR expression by the snpA promoter in pANT851 (Dickens M L, Strohl W R (1996) J. Bacteriol. 178:3389-3395; Dickens M L, Ye J, Strohl W R (1996) J. Bacteriol. 178:3384-3388; Dickens M L, Priestley N D, Strohl W R (1997) J. Bacteriol. 179:2642-2650)), or increasing the expression of the vph resistance gene (i.e. addition of plasmid pIJ364 which contains the vph resistance gene (Kieser T, Hopwood D A, Wright H M, Thompson C J (1982) Mol. Gen. Genet. 185:223-238) can result in increased viomycin production. Increased viomycin production may involve one or more of these processes. In addition, the flanking regions of the BAC that contain the 20 kb upstream of VioT and 20 kb upstream of VioA can be reduced or deleted so as to maximize viomycin production.

The general methods for constructing recombinant DNA which can transform target cells are well known to those skilled in the art, and the same compositions and methods of construction can be utilized to produce the DNA useful herein. For example, J. Sambrook et al., Molecular Cloning: A Laboratory Manual, Cold Spring Harbor Laboratory Press (2d ed., 1989), provides suitable methods of construction.

The recombinant DNA can be readily introduced into the host cells by any procedure useful for the introduction into a particular cell, e.g., calcium phosphate precipitation, protoplast fusion, conjugation, lipofection, electroporation, gene gun and the like.

As used herein, the term "cell line" or "host cell" is intended to refer to well-characterized homogenous, biologically pure populations of cells. These cells can be eukaryotic cells that are neoplastic or which have been "immortalized" in vitro by methods known in the art, as well as primary cells, or prokaryotic cells. In particular, the cell line or host cell can be of mammalian, plant, insect, yeast, fungal or bacterial origin.

"Transfected" or "transformed" is used herein to include any host cell or cell line, the genome of which has been altered or augmented by the presence of at least one DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The transfected DNA can be maintained as an extrachromosomal element or as an element which is stably integrated into the host chromosome of the host cell. Host cells with transfected DNA maintained as an extrachromosomal element or as an element stable integrated into the host chromosome are referred to as a "recombinant host cell."

Moreover, recombinant polypeptides having a particular activity can be prepared via "gene-shuffling". See, for example, Crameri et al., Nature, 391, 288 (1998); Patten et al., Curr. Op. Biotech., 8, 724 (1997), U.S. Pat. Nos. 5,837,458, 5,834,252, 5,830,727, 5,811,238, 5,605,793).

For phagemids, upon infection of the host cell which contains a phagemid, single-stranded phagemid DNA is produced, packaged and extruded from the cell in the form of a transducing phage in a manner similar to other phage vectors. Thus, clonal amplification of mutant encoding nucleotide sequences carried by phagemids is accomplished by propagating the phagemids in a suitable host cell.

Following clonal amplification, the cloned donor pool of mutants is infected with a helper phage to obtain a mixture of phage particles containing either the helper phage genome or phagemids mutant alleles of the wild-type encoding nucleotide sequence.

Infection, or transfection, of host cells with helper phage is generally accomplished by methods well known in the art (see., e.g., Sambrook et al., supra; and Russell et al. (1986) Gene 45:333-338).

The helper phage can be any phage which can be used in combination with the cloning phage to produce an infective transducing phage. For example, if the cloning vector is a cosmid, the helper phage will necessarily be a lambda phage. Preferably, the cloning vector is a phagemid and the helper phage is a filamentous phage, and preferably phage M13.

If desired after infecting the phagemid with helper phage and obtaining a mixture of phage particles, the transducing phage can be separated from helper phage based on size difference (Barnes et al. (1983) Methods Enzymol. 101:98-122), or other similarly effective techniques.

The entire spectrum of cloned donor mutations can now be transduced into clonally amplified recipient cells into which have been transduced or transformed a pool of mutant encoding nucleotide sequences. Recipient cells which can be employed in the method disclosed and claimed herein can be, for example, *E. coli*, or other bacterial expression systems which are not recombination deficient. A recombination deficient cell is a cell in which recombinatorial events are greatly reduced, such as rec.sup.-mutants of *E. coli* (see, Clark et al. (1965) Proc. Natl. Acad. Sci. USA 53:451-459).

These transductants can now be selected for the desired expressed protein property or characteristic and, if necessary or desirable, amplified. Optionally, if the phagemids into which each pool of mutants is cloned are constructed to express different genetic markers, as described above, transductants can be selected by way of their expression of both donor and recipient plasmid markers.

The recombinants generated by the above-described methods can then be subjected to selection or screening by any appropriate method, for example, enzymatic or other biological activity.

The above cycle of amplification, infection, transduction, and recombination can be repeated any number of times using additional donor pools cloned on phagemids. As above, the phagemids into which each pool of mutants is cloned can be constructed to express a different marker gene. Each cycle could increase the number of distinct mutants by up to a factor of $10^6$. Thus, if the probability of occurrence of an inter-allelic recombination event in any individual cell is f (a parameter that is actually a function of the distance between the recombining mutations), the transduced culture from two pools of $10^6$ allelic mutants will express up to $10^{12}$ distinct mutants in a population of $10^{12}$/f cells.

EXAMPLE 1

Sequence and Characterization of the Viomycin Biosynthetic Gene Cluster Materials and Methods Bacterial strains and growth media. *Streptomyces* sp. ATCC11861 (which is equivalently named *Streptomyces vinaceus*) was obtained from the American Type Culture Collection and grown on ISP Medium 2 (Difco 0770). The strain was grown in BactoTm Tryptic Soy Broth (TSB) when obtaining mycelia for chromosomal DNA isolation. For the production and purification of viomycin, TSB-grown mycelia were used to inoculate 100 ml of viomycin production medium (Quadri, L. E., et al., 1998). For conjugations, mannitol soya flour agar was used (Kieser, T., et al., 2000).

*Escherichia coli* strains were grown in LB medium or on LB agar supplemented with the appropriate antibiotic as indicated. When grown in microtiter plates, cosmid-containing strains were grown in freezing medium (Whitman, W. B., et al., 1998) supplemented with kanamycin (Kan) (50 µg/ml). The *E. coli* strains used were DH5a, XL-1 Blue MR (Stratagene), HB101/pRK2013 (Figureski, D. H., and D. R. Helinski, 1979) (from M. Rondon, UW-Madison) and ET12567 (MacNeil, D. J., et al., 1992) (from C. Khosla, Stanford Univ.).

Genomic DNA isolation and cosmid library construction. 3.0 g (wet weight) of *Streptomyces* sp. ATCC11861 mycelia were used for genomic DNA isolation following a previously described protocol (Pootoolal, J., et al., 2002). Genomic DNA was partially digested with Sau3AI to give 30-50 kb fragments that were subsequently ligated into the BamHl site of SuperCos1 (Stratagene), prepared following the manufacturer's instructions. The DNA was then packaged into lambda phage using the Gigapack III XL Packaging Extract Kit (Stratagene) and used to infect *E. coli* XL-1 Blue MR, following the manufacturer's instructions. 1248 cosmid-containing clones were isolated and were frozen at −80° C. individually in microtiter dish wells as well as in pools of 8 clones consisting of 25 µl from each member of a microtiter dish column. Thus, 1248 individual cosmids were also represented in 156 cosmid pools.

Screening the cosmid library. The cosmid library was first screened by PCR amplification for those cosmids that contained vph, the viomycin resistance gene (Bibb, M. J., 1985). Primers used were the following: Vph/FEco (5' AGMGTG-GAGAATTCGCCCACCATGAG 3') and Vph/REco (5' CCTTCAGAATTCCTGTCACGCTGCCCG 3'). Boiled cells of each cosmid pool were used as a source of template DNA for PCR amplification. Individual members of each vph-positive cosmid pool were subsequently screened by PCR amplification to identify the specific cosmid containing vph. Cosmid pVIO-P2C3RG was identified in this manner.

From the pVIO-P2C3RG sequence, two primers based on the putative viomycin biosynthetic gene vioG were designed (vio-P2-5p (5' GGGGAGACGTACTTCTTCCA 3') and vio-P2-3p (5' GGCGAGTTCACGGGAGATA 3')). These primers were used to screen the library a second time, by PCR amplification, to identify cosmids containing vioG. The vioG-positive cosmids were then screened by PCR amplification for the absence of vph. A vioG-positive but vph-negative cosmid pVIO-P8C8RH was thus isolated.

Sequencing and annotating the viomycin biosynthetic gene cluster. 2-3 kb fragments from cosmids pVIO-P2C3RG and pVIO-P8C8RH were subcloned into PSMART™LCKan by Lucigen Corp. (Middleton, Wis.). Subclones were submitted to the Genome Center Sequencing Facility at UW-Madison where they were sequenced (seven-fold coverage, two-fold minimum). Contigs were assembled using SeqMan (Lasergene, Madison, Wis.). Annotation of ORFs and putative gene functions were assigned using a combination of MapDraw (Lasergene, Madison, Wis.), blastp, PSI-BLAST, and RPS-BLAST (NCBI) (Altschul, S. F., et al., 1997) (using default parameters). The completed viomycin biosynthetic gene cluster has been deposited in GenBank (accession no. AY263398, as of Aug. 25, 2003) and is given in SEQ ID NO:1. The gene product for each of the genes contained in this cluster is also available (see AAP924291 through AAP92511) and is given in SEQ ID NOs:2-22. In case of a discrepancy between the sequence listing and the GenBank listing, the GenBank listing controls.

Insertional inactivation of vioA. An internal fragment of vioA was introduced into the suicide vector pOJ260 (Bierman, M., et al., 1992) using PCR-based cloning. The primers for vioA PCR amplification were the following: VioA/Pst 5' TCACGCCGGTCGAGCAGGA 3' and VioA/Eco 5' ACGC-CGTACTCGCGCAGG 3'. The PCR-amplified product was digested with Pstl and EcoRI and cloned into the corresponding restriction sites of pOJ260, yielding pOJ260-vioA. This plasmid was transformed into ET12567, and the resulting strain was used for conjugation of pOJ260-vioA into *Streptomyces* sp. ATCC11861 using a triparental mating protocol (Kieser, T., et al., 2000). The triparental mating involved ET12567/pOJ260-vioA, HB101/pRK2013, and *Streptomyces* sp. ATCC11861s.

To confirm pOJ260-vioA insertion into the chromosomal copy of vioA, chromosomal DNA was purified from the mutant strains and analyzed by PCR amplification and subsequent restriction enzyme analysis of the amplified products. Primers used for this analysis were VioA/Pst and VioA/Eco, which are outside the region cloned into pOJ260, and the FOR (5' CGCCAGGGTTTTCCCAGTCACGAC 3') and REV (5' TCACACAGGAAACAGCTATGA 3') primers that anneal to regions just outside the multiple cloning site of pOJ260. During this analysis it was determined that the 5' end of vioA in one mutant strain (MGT1001) had undergone a deletion of approximately 400 bp between a BglII and an NcoI restriction site within vioA (data not shown). This was not characterized further because vioA was inactivated regardless of the nature of this deletion. The two other isolated vioA mutants (MGT1002 and MGT1003) did not contain this deletion (data not shown).

Production and isolation of viomycin. 100 ml cultures of the wild-type or mutant strains of *Streptomyces* sp. ATCC11861 were grown in viomycin production medium at 28° C. for five days. Mycelia were removed by centrifugation, and the resulting supernatant was used for viomycin purification following the previously published protocol (Tam, A. H. -K., and D. C. Jordan, 1972).

High-Performance Liquid Chromatography (HPLC) of purified viomycin. Purified viomycin samples were analyzed by HPLC (Beckman System Gold) using a Macrosphere SCX 300A 7U column (Alltech) at a flow rate of 1 ml/min. The following buffers were used: A –20 mM Tris-HCl pH 6.4; B –20 mM Tris-HCl, 1M sodium acetate pH 6.4. The separation profile was 5 min isocratic development at 100%A/0%B, 15 min linear gradient from 100%A/0%B to 0%A/100%B, 5 min isocratic development at 0%A/100%B. Elution of viomycin was monitored at the characteristic absorbance of 268 nm. Purified viomycin had the same UV/vis spectrum and HPLC retention time as authentic viomycin, and also co-eluted from the HPLC with authentic antibiotic regardless of elution profile.

Results

Cloning and sequencing of the viomycin biosynthetic gene cluster. We constructed a cosmid library of the *Streptomyces* sp. ATCC11861 genome, and used PCR amplification to screen the library for cosmids containing vph, the known viomycin resistance gene (Bibb, M. J., et al., 1985). The resistance gene was targeted because the resistance gene for a particular antibiotic is typically encoded in the same region of the chromosome as the biosynthetic gene cluster for that antibiotic (Martin, M. F., and P. Liras, 1989). Sequencing out of the resistance gene from one of the vph-positive cosmids, pVIO-P2C3RG, identified an ORF that encoded a putative lysine 2,3-aminomutase. Since viomycin contains a β-lysine moiety, and lysine 2,3-aminomutases catalyze the formation of β-lysine, we hypothesized that pVIO-P2C3RG contained a portion of the viomycin biosynthetic gene cluster.

Preliminary analysis of the DNA sequence from pVIO-P2C3RG suggested only a portion of the viomycin biosynthetic gene cluster was contained on the cosmid. We then screened the library a second time using PCR primers based on a putative viomycin biosynthetic gene, vioG, that was present on pVIO-P2C3RG. The vioG-positive cosmids were then screened for the absence of vph, identifying cosmids containing DNA that overlapped but was not redundant with the insert in pVIO-P2C3RG. From this analysis pVIO-P8C8RH was isolated, and both cosmids were completely sequenced.

Figure 2:
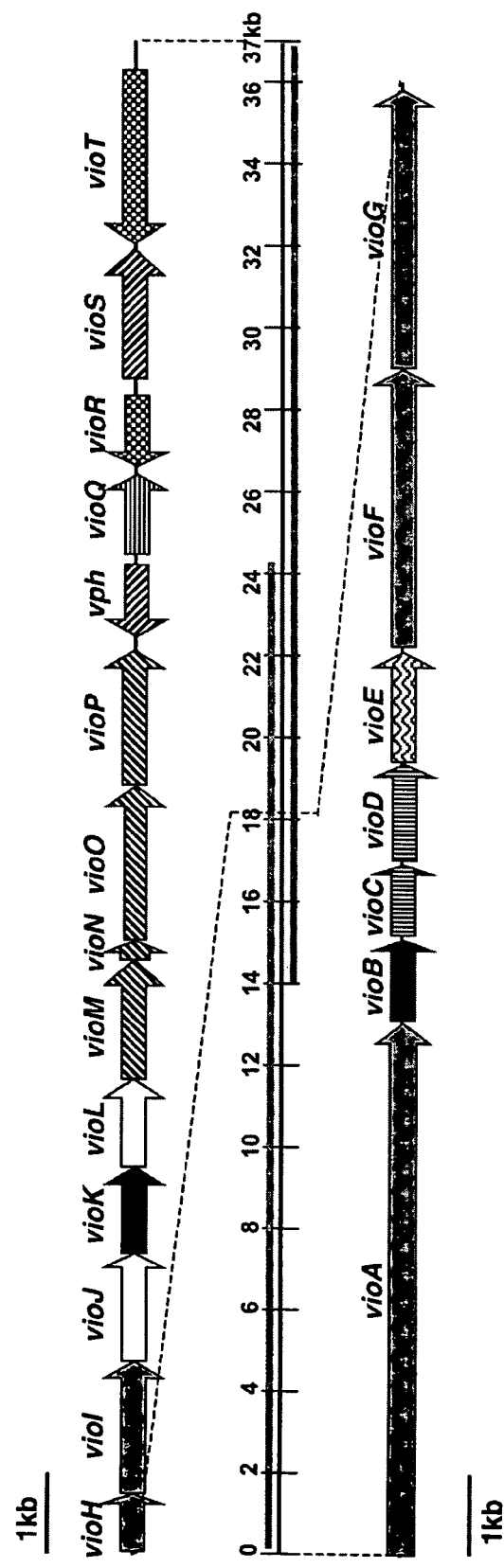
FIG. 2. Is a schematic representation of the viomycin biosynthetic gene cluster. The center line denotes 37 kb encoding all ORFs involved in viomycin biosynthesis with the bars above and below the center line representing DNA present on cosmids pVIO-P8C8RH and pVIO-P2C3RG, respectively. Arrows above and below the center line identify the direction of transcription of ORFs. Coding of ORF biosynthetic function is as follows: NRPS, gray; L-2,3-diaminopropionate, black; L-2,3-diaminopropionate→β-ureidodehydroalanine, white; (2S,3R)-capreomycidine, vertical bars; (2S,3R)-capreomycidine hydroxylation, horizontal bars; β-lysine, right-slant bars; resistance and activation, left-slant bars; regulation, cross-hatched bars; export, waves.

Analysis of the viomycin biosynthetic gene cluster. The viomycin biosynthetic gene cluster includes approximately 36.3 kb of contiguous DNA encoding 20 ORFs involved in the biosynthesis, export, regulation, and activation of the antibiotic, in addition to the previously isolated resistance gene vph (FIG. 2 and Table 1). An additional ~20 kb on either side of the predicted gene cluster were sequenced and analysis of this DNA did not identify any genes predicted to be involved in viomycin production. Thus, vioA, vioT, and the genes between them, constitute the viomycin biosynthetic gene cluster.

Figure 3:
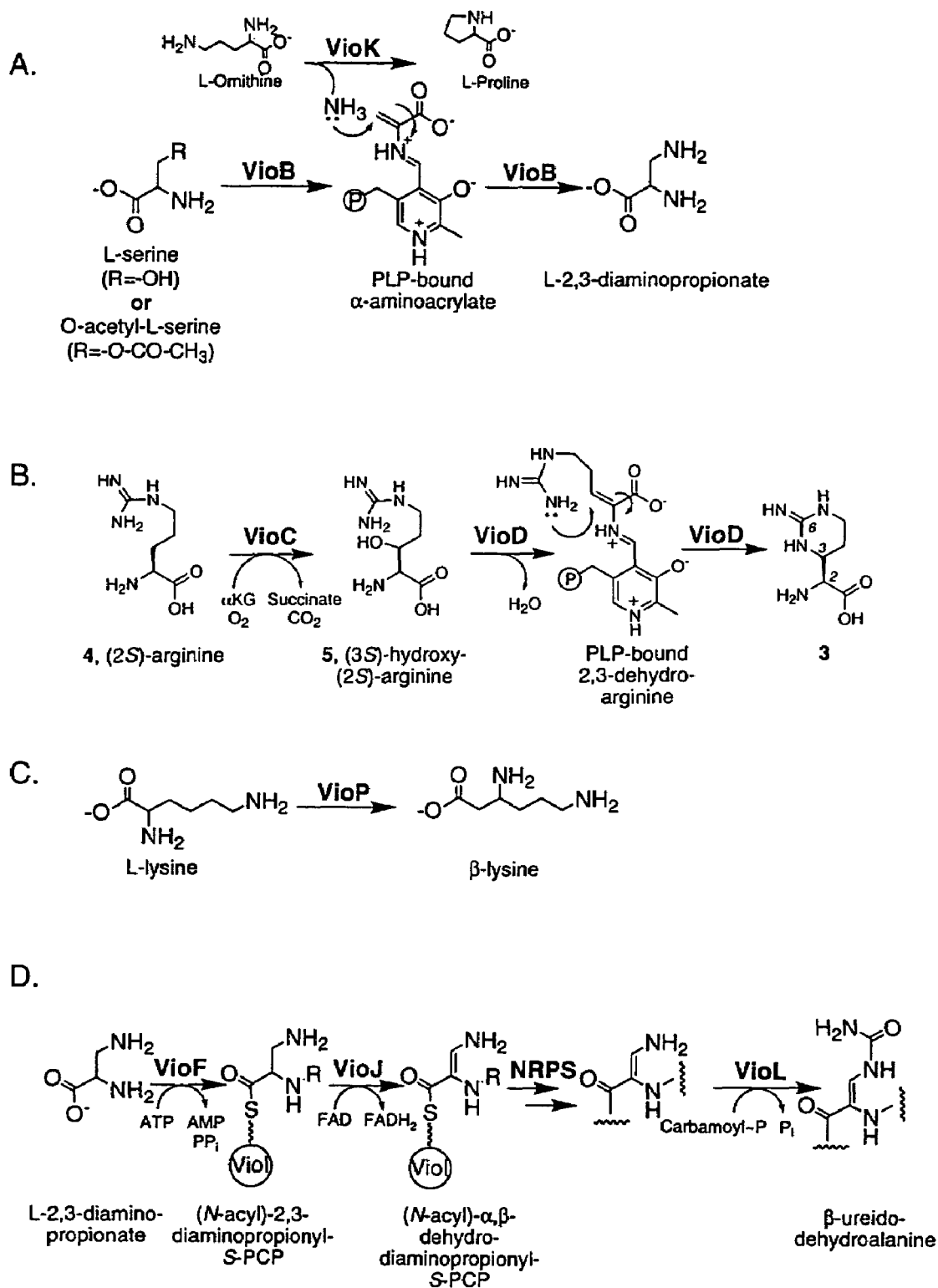
FIG. 3. Is a scheme illustrating the biosynthetic pathways for the four nonproteinogenic amino acids in VIO (reactions A-D). Abbreviations are as in the text. In reaction B, the end product labelled 3 is (2S,3R)-capreomycidine. In reaction D: R=(-H, or -tripeptide) and the last step in β-ureidodehydroalanine biosynthesis occurs after cyclic pentapeptide synthesis.

Biosynthesis of the nonproteinogenic amino acids. Viomycin is a six amino acid peptide consisting of two L-serine residues and one residue of each of the following nonproteinogenic amino acids: L-2,3-diaminopropionate, β-ureidodehydroalanine, β-lysine, and L-tuberactidine. Based on the common observation that secondary metabolite biosynthetic gene clusters typically encode all the enzymes needed for the production of any precursors specific for that particular metabolite (Chater, K. F., and C. J. Bruton, 1985; Du, L., et al., 2000; van Wageningen, A. M. A., et al., 1998), the viomycin gene cluster should encode the enzymes needed to generate L-2,3-diaminopropionate, (2S,3R)-capreomycidine, and β-lysine. The conversion of L-2,3-diaminopropionate to β-ureidodehydroalanine and (2S,3R)-capreomycidine to L-tuberactidine occurs after precursor incorporation into the growing peptide chain as will be discussed below.

i. Biosynthesis of L-2,3-diaminopropionate. Precursor labeling studies on viomycin (Carter, J. H., et al., 1974) and the capreomycins (Wang, M., and S. J. Gould, 1993) have determined that L-serine is the precursor for L-2,3-diaminopropionate. Bioinformatic analysis of the viomycin biosynthetic gene cluster suggests that the conversion of L-serine to L-2,3-diaminopropionate is catalyzed by the concerted actions of VioB and VioK (FIG. 3A).

VioB is a homolog of cysteine synthases and serine dehydratases (38% identity, 52% similarity to Reut3764 from *Ralstonia metallidurans*; 35% identity, 52% similarity to SAVOL 16 from *Staphylococcus aureus* Mu50), enzymes that catalyze the pyridoxal phosphate (PLP)-dependent replacement or elimination, respectively, of the β-substituent of their substrate (Alexander, F. W., et al., 1994). During catalysis, both of these enzymes form a PLP bound a-aminoacrylate intermediate. VioB uses a similar mechanism to form a Schiff base linkage between PLP and an α-aminoacrylate intermediate (FIG. 3A). VioB then catalyzes a β-replacement reaction analogous to that seen for cysteine synthases. However, while cysteine synthases use sulfur from sulfide as the nucleophile, VioB uses the nitrogen of ammonia as the nucleophile (FIG. 3A). The source of this nucleophile for viomycin biosynthesis is the ammonia liberated from L-ornithine by VioK (FIG. 3A). VioK is a homolog of ornithine cyclodeaminases (31% identity, 47% similarity to Reut3765 from *Ralstonia metallidurans*; 28% identity, 47% similarity to SAVOL 17 from *Staphylococcus aureus* Mu50), enzymes that convert L-ornithine to L-proline with the release of ammonia (Costilow, R. N., and L. Laycock, 1971; Muth, W. L., and R. N. Costilow, 1974ab). Thus, VioK functions as an amidotransferase during viomycin biosynthesis since ammonia is the relevant product of the reaction, not L-Pro.

Figure 7:
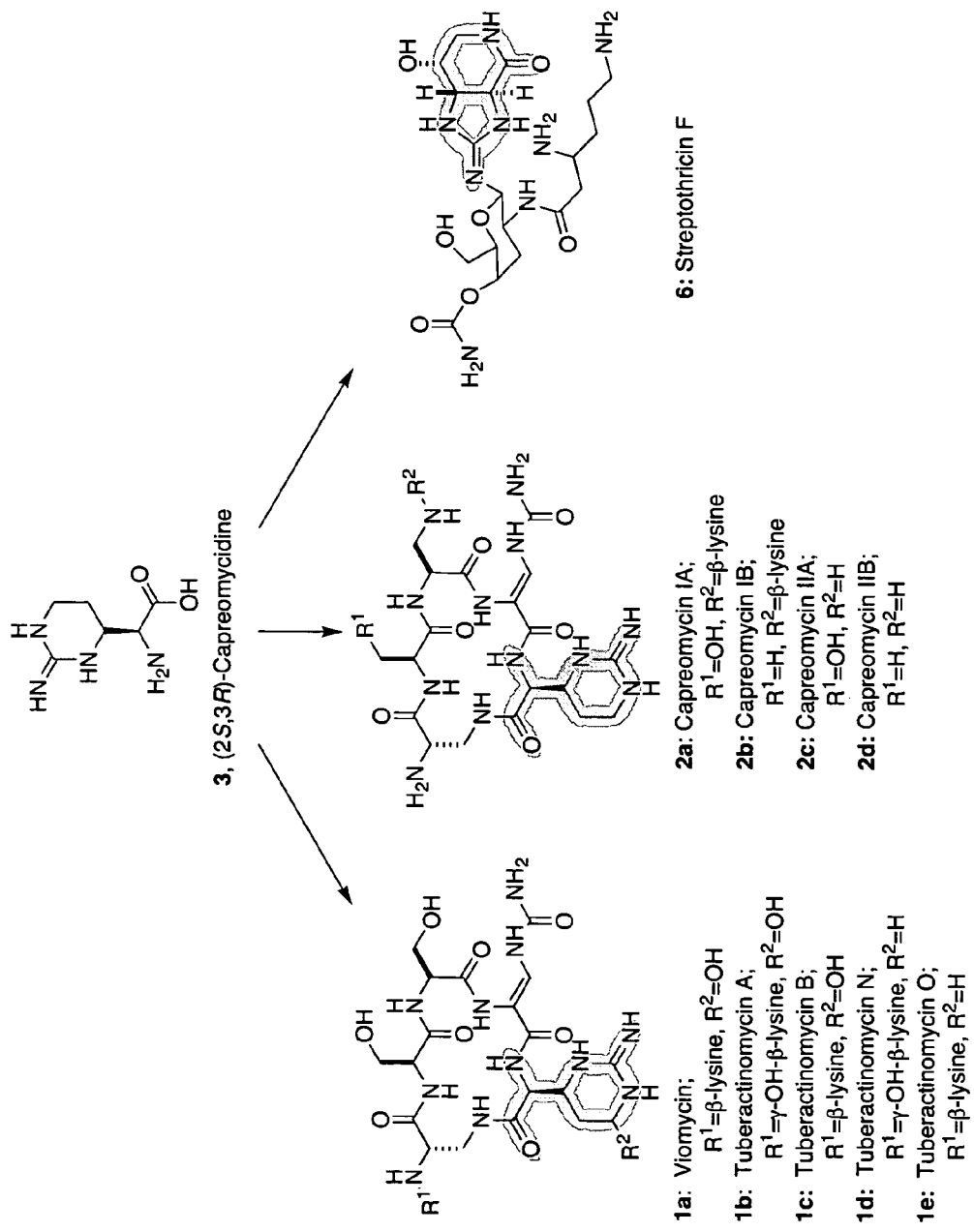
FIG. 7. Is a scheme illustrating the relationship among the chemical structures of exemplary antibiotics that incorporate (2S, 3R)-capreomycidine. Highlighted in gray are the portions of the antibiotics derived from (2S, 3R)-capreomycidine. For compounds 1a-e and 2a-d, the shaded amino acids are residue 5 of the pentapeptide cores of the antibiotics. The shaded portion of 6 identifies the streptolidine lactam moiety.

The role of VioB was verified by construction of an in frame deletion of VioB (ΔVioB). The ΔVioB strain no longer produces viomycin. When DAP was added to the growth medium, viomycin production was restored, confirming our prediction that vioB is involved specifically in DAP biosynthesis.

ii. Biosynthesis of (2S,3R)-capreomycidine. Precursor labeling studies have determined that L-tuberactidine of viomycin (Carter, J. H., et al., 1974) and (2S,3R)-capreomycidine of the capreomycins (Gould, S. J., and D. A. Minott, 1992) are derived from (2S)-arginine. As discussed below, (2S,3R)-capreomycidine is incorporated into the growing peptide chain and is subsequently converted to L-tuberactidine after peptide synthesis is completed (FIG. 7). VioC and VioD convert (2S)-arginine to (2S,3R)-capreomycidine (FIG. 3B) (Ju et al., 2004).

VioC is a homolog of clavaminic acid synthases (45% identity, 60% similarity to SttL from *Streptomyces rochei*), which are non-heme iron dioxygenases involved in clavulanic acid biosynthesis (Townsend, C. A., 2002). The first reaction catalyzed by one of the clavaminic acid synthases, CS2, is the hydroxylation of the β-carbon of the arginine moiety of 5-guanidino-2-(2-oxo-azetidin-1-yl)-pentanoic acid (Salowe, S. P., et al., 1990). VioC catalyzes a similar reaction to generate β-hydroxyarginine (FIG. 3B). This product is then a substrate for VioD, a homolog of PLP-dependent aromatic amino acid aminotransferases (40% identity, 51% similarity to SttN from *Streptomyces rochei*). VioD catalyzes a β-elimination reaction to generate a PLP-linked α,β-dehydroarginine that would allow for intramolecular addition of the δ-guanido moiety to the carbon, thus generating (2S,3R)-capreomycidine.

Gould and Minott predicted the presence of the α,β-dehydroarginine intermediate in the pathway based on their results from feeding experiments with [2,3,3,5,5-²H₅]-arginine during capreomycin biosynthesis (Gould, S. J., and D. A. Minott, 1992). Their prediction was based on the loss of the deuterium from C2 and the loss of one deuterium from C3, which would be consistent with such an intermediate. They also predicted that the (2S)-arginine-to-(2S,3R)-capreomycidine conversion would occur after peptide synthesis so that the α,β-dehydroarginine intermediate could be stabilized by an amide bond. Our studies indicate (2S,3R)-capreomycidine is produced before peptide synthesis (FIG. 3B), with the PLP cofactor stabilizing the α,β-dehydroarginine intermediate.

The two putative enzymes showing the highest amino acid identity with VioC and VioD are SttL (45% identity, 60% similarity) and SttN, respectively (40% identity, 52% similarity). The genes encoding SttL and SttN are within the proposed biosynthetic gene cluster for the broad-spectrum antibiotic streptothricin (Fernandez-Moreno, M. A., et al., 1997), and (2S,3R)-capreomycidine is predicted to be an intermediate in the biosynthesis of this antibiotic (Gould, S. J., and K. J. Martinkus, 1981a,b; Jackson, M. D., et al., 2002; Martinkus, K. J., et al., 1983). Thus, the (2S,3R)-capreomycidine intermediate in streptothricin biosynthesis is generated by an analogous mechanism to that proposed for viomycin. The function of VioC and VioD was verified by heterologously overexpressing these enzymes in *E. coli* as outlined below in Example 3.

iii. Biosynthesis of β-lysine. Viomycin and streptothricin also contain β-lysine moieties (FIG. 7). Both biosynthetic clusters encode homologs to lysine-2,3-aminomutases (VioP in viomycin; SttO in streptothricin) (32% identity, 47% similarity to SttO from *Costridium subterminale*). Frey and colleagues have extensively studied lysine-2,3-aminomutases and have shown these enzymes catalyze the migration of the a-amino group of L-lysine to the β-carbon (Frey, P. A., 1993). We predict both VioP and SttO catalyze the same reaction to generate a source of β-lysine for viomycin and streptothricin, respectively (FIG. 3C).

Assembly of the cyclic pentapeptide core. Although viomycin is a peptide consisting of six amino acids, the cyclic pentapeptide core of the antibiotic is biosynthesized first, followed by acylation of residue 1 with β-lysine. This pathway is based on TUBs being isolated with or without a β-lysine moiety (FIG. 1), suggesting β-lysine addition is separate from cyclic pentapeptide synthesis. We predict that a five-module NRPS synthesizes and cyclizes the pentapeptide core of viomycin.

Figure 4:
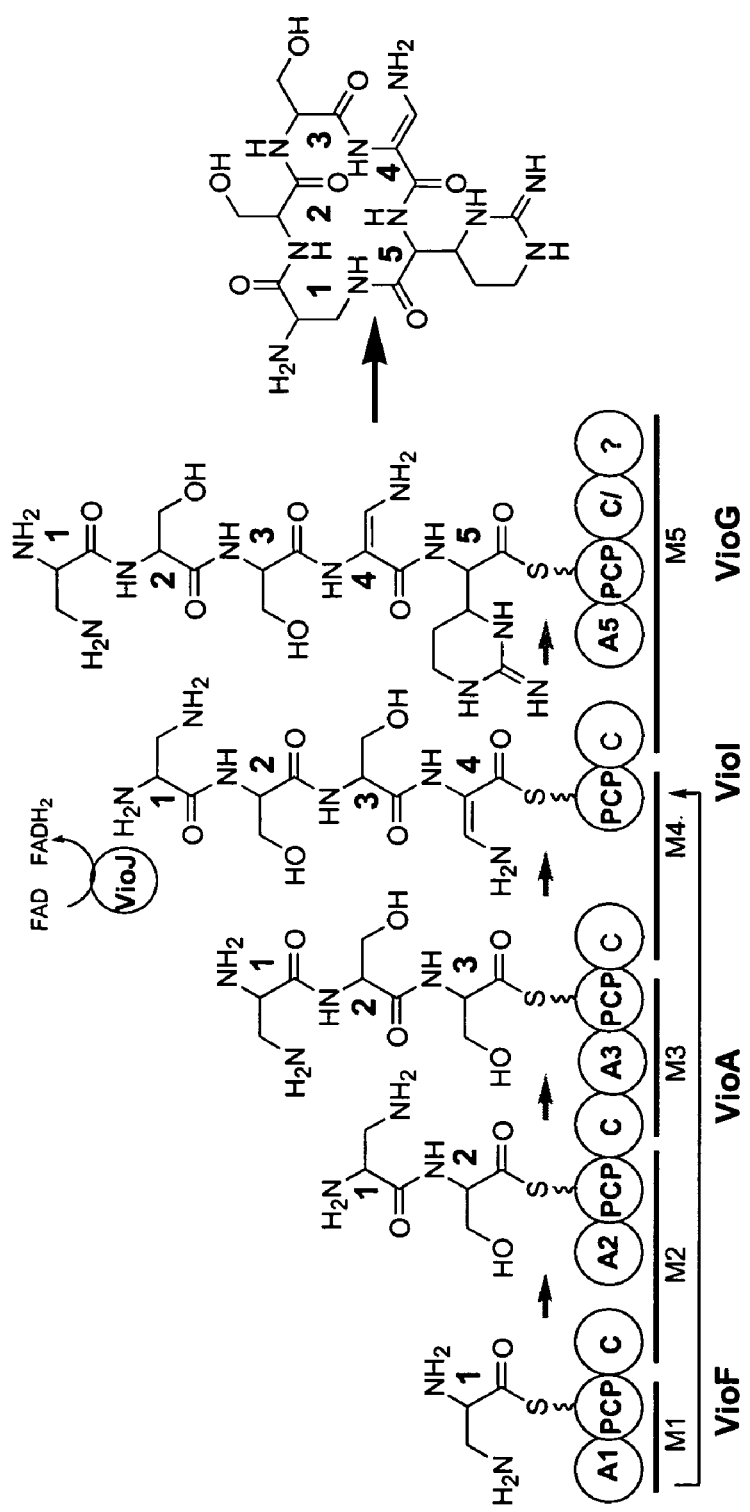
FIG. 4. Schematic representations of the viomycin NRPS. The domains of each subunit are shown as circles. The bars below the NRPS subunits denote specific modules, which are annotated M1 through M5. The arrow between VioF and VioI represents the in trans aminoacylation of VioI by the A1 domain of VioF. The gray arrows indicate the direction of peptide synthesis. The abbreviations for NRPS domains are the same as those used in Table I.

During NRPS-catalyzed peptide synthesis, the domains, modules, and subunits of these enzymes are typically aligned in a sequence that is co-linear with the resulting peptide. Additionally, the organization of the NRPS subunits usually follows the order in which the corresponding genes are found on the genome (Cane, D. E., and C. T. Walsh, 1999). Neither of these rules appear to be followed by the viomycin NRPS. First, there are five modules for cyclic pentapeptide biosynthesis, but one of these modules lacks an adenylation (A) domain (FIG. 4). Therefore, one of the other A domains must function twice (FIG. 4). Secondly, it is not anticipated that the NRPS subunits function in the order their corresponding genes are arrayed on the chromosome (FIG. 2, and 4).

To determine the order in which the NRPS subunits function, we analyzed A domain specificity codes (Challis, G. L., et al., 2000; Stachelhaus, T., et al., 1999), conserved domain sequences (Konz, D., and M. A. Marahiel, 1999), and domain organizations. As shown in FIG. 4, VioF activates and tethers L-2,3-diaminopropionate (residue 1) to its peptidyl carrier protein (PCP) domain. Thus, the first two domains (A-PCP) of VioF form the initiating module of the NRPS. The condensation (C) domain of VioF then catalyzes peptide bond formation between residue 1 bound to VioF, and the L-serine (residue 2) bound to the first PCP domain of VioA. Thus module 2 of the NRPS spans both VioF and VioA. The first C domain of VioA catalyzes peptide bond formation between the dipeptide (residues 1-2) bound to the first VioA PCP domain and L-serine (residue 3) bound to the second PCP domain of VioA. Consistent with this, both A domains of VioA have specificity codes for L-serine recognition (DVYHFSLVDK and DVRHMSMVMK) (Challis, G. L., et al., 2000; Stachelhaus, T., et al., 1999). The second C domain of VioA then catalyzes peptide bond formation between the tripeptide (residues 1-2-3) on VioA and L-2,3,-diaminopropionate (residue 4) bound to the PCP domain of VioI.

There are two unusual aspects of the viomycin NRPS to highlight at this point in cyclic pentapeptide synthesis. First, VioI lacks the necessary A domain to aminoacylate itself with L-2,3-diaminopropionate. Thus, the A domain of VioF aminoacylates VioI in trans (FIG. 4). Second, VioJ catalyzes the next step in peptide synthesis by desaturating the α,β-bond of residue 4 to generate a tetrapeptide that includes the desaturated 2,3-diaminopropionate (FIG. 4). This is based on VioJ being a homolog of acyl-CoA dehydrogenases (38% identity, 54% similarity from *Pseudomonas fluorescens* pfO-1-Pflu 1686) (Thorpe, C., and J. J. Kim, 1995), but it lacks the conserved aspartate residue in acyl-CoA dehydrogenases needed for the recognition of the adenine base of coenzyme A (Battaile, K. P., et al., 2002; Tiffany, K. A., et al., 1997). We have recently shown that acyl-CoA dehydrogenase homologs in the undecylprodigiosin and pyoluteorin pathways, that also lack this residue, catalyze α,β-desaturations of PCP-bound substrates, not their CoA derivatives (Thomas, M. G., et al., 2002). Thus, VioJ functions in an analogous manner, and would be the first α,β-desaturase to be an integral part of a peptide synthesizing NRPS.

VioG is the best candidate for the terminal subunit since the C-terminus of VioG contains a truncated condensation (C) domain (immediately after the C3 core motif, suggesting it is inactive. This is consistent with VioG containing the terminal module since peptide bond formation with a downstream PCP-bound substrate is not required. This truncated C domain precedes a terminal domain of unknown function. Typically, the terminal domain of an NRPS is a thioesterase that catalyzes hydrolysis or cyclization and release from the final PCP domain (Marahiel, M. A., et al., 1997). While a weak thioesterase motif (GSAG) could be found in this terminal domain, it is not clear whether it plays any role in peptide cyclization and release, therefore, the mechanism of pentapeptide macrocyclization remains an open question.

Modifications of the cyclic pentapeptide. Following the formation of the cyclic pentapeptide shown in FIG. 4, there are three modifications that must occur: 1) carbamoylation of the α-amino group of residue 4 to form β-ureidodehydroalanine, 2) hydroxylation of the C6 of residue 5 to form tuberactidine, and 3) acylation of the α-amino group of residue 1 with β-lysine.

VioL is predicted to catalyze the carbamoylation of residue 4 based on the amino acid similarity between VioL and ornithine carbamoyltransferases (55% identity, 67% similarity from *Streptomyces avennitilis* (SAV3641)) (Legrain, C., and V. Stalon, 1976). The biosynthetic pathway for L-2,3-diaminopropionate conversion to β-ureidodehydroalanine is predicted to occur as shown in FIG. 3D. However, we cannot eliminate the possibility that carbamoylation occurs immediately after the desaturation of residue 4 while it is bound to the Viol. Further analysis is needed to discriminate between these possibilities.

The hydroxylation of the C6 of residue 5, which generates tuberactidine from (2S,3R)-capreomycidine, is catalyzed by VioQ based on its similarity to phenylpentanoic acid dioxygenase and related ring-hydroxylating dioxygenases (30% identity, 48% similarity with 3-chlorobenzoate 3,4-dioxygenase from *Comamonas testosteroni*) (Mason, J. R., and R. Cammack, 1992). Hydroxylation of residue 5 to generate the L-tuberactidine moiety occurs after peptide synthesis based on the isolation of tuberactinomycin derivatives with and without this hydroxylation (FIG. 1), suggesting that the hydroxylation is not a prerequisite for peptide synthesis. However, as with the carbamoylation discussed above, we cannot eliminate the possibility that the hydroxylation precedes the completion of peptide synthesis.

Figure 5:
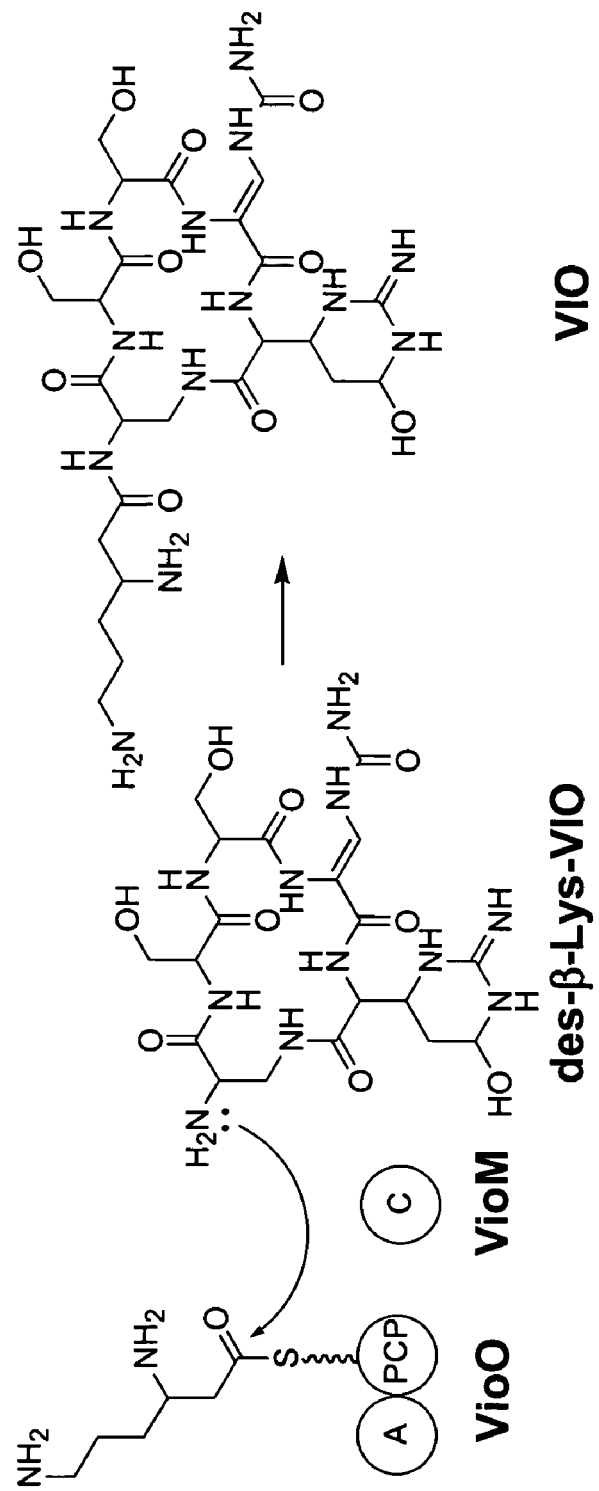
FIG. 5. Is a reaction scheme illustrating the VioO and VioM-catalyzed N-acylation of des-β-lysine-viomycin with β-lysine. VioP converts L-Lysine to β-Lysine and VioN plays a yet undefined role in β-Lysine biosynthesis and attachment.

The sixth amino acid present in viomycin is β-lysine. This attachment of β-lysine to the α-amino group of residue 1 occurs by the actions of VioO (A-PCP) and VioM (C) (FIG. 5). Since these two proteins contain the three core domains of an NRPS module, this can be considered a monomodular NRPS. VioO will activate and tether β-lysine to its C-terminal PCP domain. Consistent with this, the A domain of VioO has the specificity code for β-lysine (DTEDVGTMVK, (Grammel, N., et al., 2002)) and preliminary results with partially purified VioO suggests it activates β-lysine (Y. Chan and M. Thomas, unpublished) (35% identity, 49% similarity to SanO of *Streptomyces ansochromogenes*).

VioM, a homolog of C domains (39% identity, 54% similarity between VioM (aa 14-434) and Nostoc punctiforme (Npun 5654) (aa 1160-1584)) then catalyzes amide bond formation between β-lysine bound to VioO and the soluble substrate des-β-lysine-viomycin (FIG. 5). This monomodular NRPS, therefore, does not function as a peptide synthetase per se, but rather as an N-acyltransferase. This mechanism is analogous to the terminal portion of the vibriobactin biosynthesis, whereby the acceptor site of the VibH C domain binds a soluble substrate instead of an amino acid tethered to a PCP (Keating, T. A., et al., 2000).

It is not clear what role VioN plays in viomycin biosynthesis. It is a homolog of a family of small proteins found in many NRPS systems (61% identity, 75% similarity to Agr_L_2317p from *Agrobacterium tumefaciens* C58), the standard of which is MbtH, a protein of unknown function in mycobactin biosynthesis (Quadri, L. E., et al., 1998). The location of vioN between vioM and vioO, suggests VioN plays some role in β-lysine addition.

Regulation, Export, Resistance, and Activation. Two putative transcriptional regulators are encoded in the viomycin biosynthetic gene cluster. VioR belongs to the OxyR family of transcriptional regulators (37% identity, 59% similarity with *Streptomyces avermitilis* SAV5624), while VioT is a homolog of NysRI (61% identity, 71% similarity with putative transcriptional regulator from *Streptomyces avermitilis*), a putative transcriptional regulator in the nystatin biosynthetic pathway (Brautaset, T., et al. 2000). The involvement of both transcriptional regulators in viomycin biosynthesis remains to be determined.

The export of the antibiotic is catalyzed by VioE, which is a permease homolog (29% identity, 43% similarity to a putative multidrug-resistance protein from *Streptomyces avernitilis* SAV3640; 29% identity, 45% similarity to a putative export protein from *Streptomyces spectabilis* SpcT). Our hypothesis is viomycin is exported in its phosphorylated form. This is based on VioS being a homolog of StrK (66% identity, 75% similarity with StrK from *Streptomyces griseus*), the streptomycin-phosphate phosphatase that removes the phosphate and activates streptomycin outside the cell (Mansouri, K., and W. Piepersberg, 1991). Thus, Vph, the previously identified viomycin phosphotransferase, catalyzes the phosphorylation of viomycin, which is then exported by VioE. VioS will reactivate the antibiotic once it is outside the cell. This mechanism of resistance and export will need to be considered when metabolically engineering the viomycin biosynthetic pathway.

Figure 6:
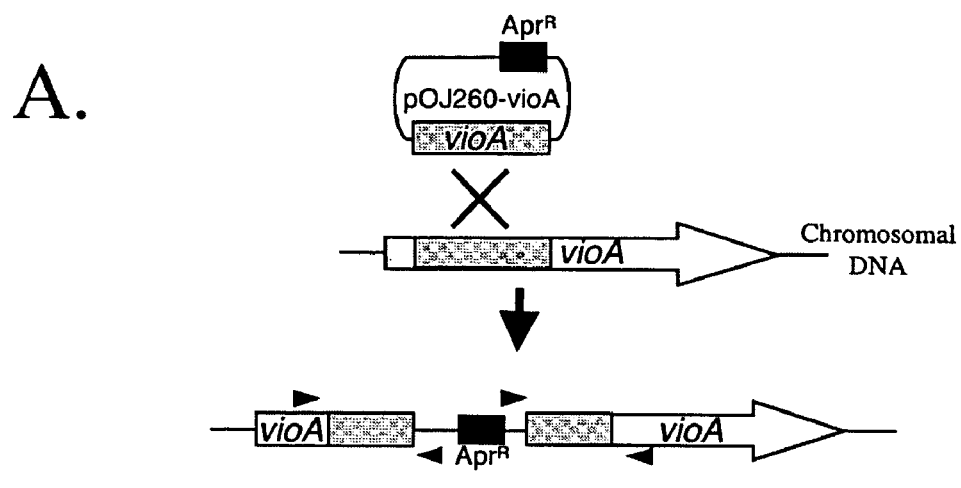
FIG. 6. A) Schematic representation of the insertion of pOJ260-vioA into the chromosomal copy of vioA by single homologous recombination. The grey boxes indicate regions of identity between the cloned vioA fragment and vioA on the chromosome. Arrowheads represent the location of primers used to confirm the vioA::pOJ260-vioA mutations. The black box and associated $Apr^R$ represent the apramycin resistance gene on pOJ260-vioA. Resistance to this antibiotic was used for selection of the single cross-over insertional inactivation of vioA. B) Representative HPLC traces comparing viomycin production from a wild-type and one of the vioA⁻ strains (MGT1001) of *Streptomyces* sp. ATCC11861 to authentic viomycin (10 µg). Viomycin was not detected in vioA⁻ strains MGT1002 or MGT1003 (data not shown).
Figure 6:
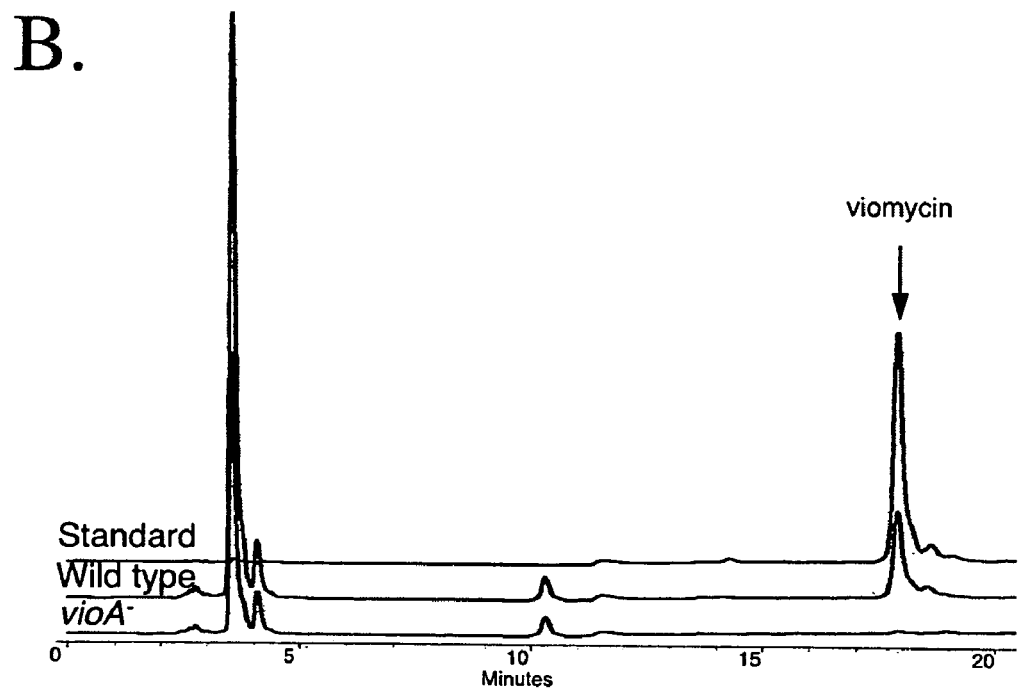

Genetic evidence that the sequenced gene cluster encodes for the viomycin biosynthetic enzymes. To confirm the gene cluster we identified is involved in viomycin biosynthesis, vioA was inactivated as shown in FIG. 6A. We chose to inactivate vioA because it encodes an essential component of the viomycin NRPS (FIG. 4), and the absence of VioA should abolish viomycin production. This result would strongly support our hypothesis that the biosynthetic gene cluster we identified assembles viomycin. Three independently isolated vioA::pOJ260-vioA strains (MGT1001, MGT1002, and MGT1003) were grown under conditions optimized for viomycin production, and the antibiotic was purified from the supernatants. The purified components of the supernatant were then analyzed for the presence of viomycin using HPLC. Viomycin was not produced by any of the vioA::pOJ260-vioA strains (FIG. 6B). Therefore, we can conclude that the gene cluster sequenced and analyzed is the viomycin biosynthetic gene cluster.

Conclusions. We have isolated, sequenced, and annotated the biosynthetic gene cluster for the antibiotic viomycin from *Streptomyces* sp. ATCC11861. This pathway involves novel precursor biosynthetic mechanisms and atypical NRPS components to generate the hexapeptide antibiotic. It is anticipated that all TUB antibiotics are biosynthesized in a similar manner to viomycin, with subtle changes to generate the structural diversity shown in FIG. 1.

Figure 1:
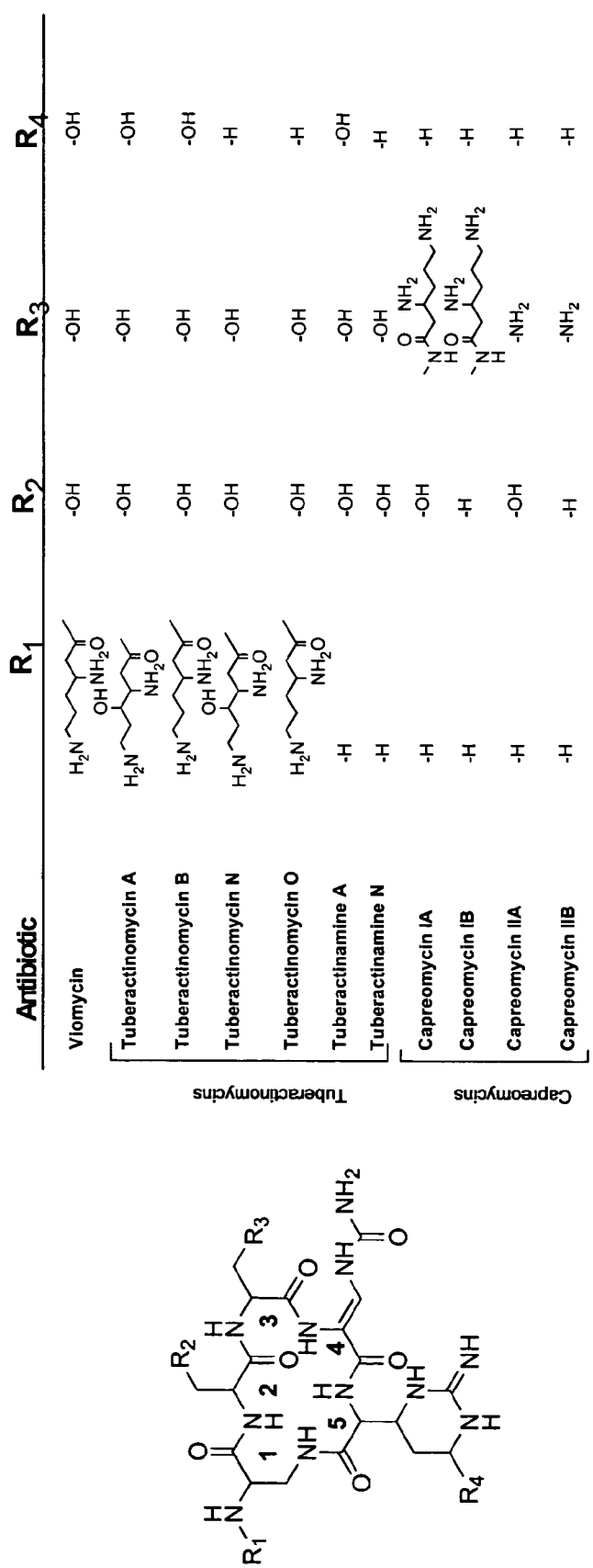
FIG. 1. Exemplary chemical structures of the TUB family of antibiotics including viomycin, tuberactinomycins, tuberactinamines and capreomycins. Numbering within the cyclic pentapeptide core is illustrated and identifies residue number as noted in the text. The various $R_1$, $R_2$, $R_3$ and $R_4$ groups are defined. Figure is as in Wank et al., 1994, with modifications.

We hypothesize that *Saccharothrix mutabilis* subsp. *capreolus*, the producing strain of the capreomycins, does not encode a VioQ homolog since the capreomycins contain (2S,3R)-capreomycidine, not L-tuberactidine (FIG. 1). We also predict that the tuberactinomycin producers encode an additional enzyme that catalyzes γ-hydroxylation of the β-lysine residue to generate tuberactinomycin A and N (FIG. 1).

The central pentapeptide core of the TUBs varies in two respects besides the (2S,3R)-capreomycidine hydroxylation discussed above. First, for viomycin and the tuberactinomycins, residue 3 of the pentapeptide core is L-serine not L-2,3-diaminopropionate as seen in the capreomycins (FIG. 1). This difference is one of the reasons why residue 3 of viomycin and the tuberactinomycins cannot be N-acylated with β-lysine, as seen in the capreomycins. It is anticipated the A domain specificity code for module 3 in the capreomycin producer is altered to activate L-2,3-diaminopropionate instead of L-serine. Secondly, residue 2 in the capreomycins can be either L-serine or L-alanine (FIG. 1), suggesting the A domain of module 2 of the NRPS has relaxed substrate specificity.

Finally, the capreomycins, while containing L-2,3-diaminopropionate at residue 1 of the pentapeptide core, are only N-acylated at residue 3 (FIG. 1). It is anticipated that the VioM homolog in Sac. mutabilis subsp. capreolus has an altered acceptor site leading to β-lysine addition at the opposing side of the cyclic pentapeptide core compared to viomycin and the tuberactinomycins. This selectivity is due, in part, to the N-acylation of the β-amino group of residue 3, not the α-amino group of residue 1 as seen in viomycin and the tuberactinomycins.

With the knowledge gained from the analysis of the viomycin biosynthetic gene cluster, a clear picture of how the TUB family of antibiotics is biosynthesized has been developed. This permits metabolic engineering and chemical modification of this family of antibiotics to combat resistant bacteria, remove unwanted side-effects for MDR-TB treatment, and develop derivatives of these antibiotics for use in the treatment of other bacterial and viral infections.

EXAMPLE 2

Metabolic Engineering to Generate Alternative Tuberactinomycin Antibiotics

Streptomyces sp. ATCC11861 can be metabolically engineered to produce alternative tuberactinomycin antibiotics through the use of genetic manipulation of the viomycin biosynthetic gene cluster. Outlined below are genetic techniques to generate previously isolated tuberactinomycins or new derivatives that have not been isolated in nature or generated chemically.

1. Production of Tuberactinamine A.

Tuberactinamine A differs from viomycin in the absence of the β-Lysine moiety tethered to the a-amino group of residue 1 FIG. 1). Tuberactinamine A has been produced by Streptomyces griseoverticillatus var. tuberacticus NRRL3482 (Morse, B. K., et al., 1997) but only when the organism was grown in the presence of (S)-2-aminoethyl-L-cysteine. Even with the addition of (S)-2-aminoethyl-L-cysteine, tuberactinamine A was still produced at a low level. The genetic inactivation of the genes involved in β-lysine biosynthesis and/or attachment results in Streptomyces sp. ATCC11861 producing only tuberactinamine A, with no contaminating viomycin.

The metabolic engineering of Streptomyces sp. ATCC11861 to produce tuberactinamine A involves the deletion of the viomycin biosynthetic genes vioM, vioN, vioO, and vioP. These four genes encode the necessary enzymes for β-Lysine biosynthesis and attachment to tuberactinamine A (FIG. 5). The deletion of these genes abolishes β-Lysine synthesis in addition to the attachment of any amino acids to the α-amino group of residue 1. Thus, the ΔvioMNOP strain of Streptomyces sp. ATCC11861 produces tuberactinamine A instead of viomycin.

To generate these deletions, we follow standard protocols (Kieser, T., et al., 2000a) for the generation of in-frame deletions of all four genes. Briefly, PCR-based cloning is used to fuse the first few codons of vioM to the final few codons of vioP. In addition to these codons, DNA containing approximately 3 kb upstream of vioM and approximately 3 kb 3' to vioP is cloned into an appropriate Streptomyces suicide vector (i.e. the temperature-sensitive plasmid pKC1139). (Bierman, M., et al., 1992)). The resulting delivery vector contains approximately 3 kb upstream of vioM through 3 kb 3' of vioP, with vioMNOP being deleted.

The resulting delivery vector is introduced into Streptomyces sp. ATCC11861 by conjugation following standard protocols (Kieser, T., et al., 2000b). Exconjugants are selected for by using the appropriate antibiotic (i.e. apramycin for pKC1139 delivery constructs). These strains contain the delivery vector replicating in Streptomyces sp ATCC11861. The plasmid-containing strains are then grown at non-permissive temperatures (37C) on antibiotic-containing medium (i.e. apramycin for pKC1139 derivatives) to select for those strains where pKC1139 has integrated into the chromosome. Those strains that grow under these conditions are then transferred to fresh medium lacking antibiotic (i.e. apramycin for pKC1139 derivatives) and grown at a permissive temperature (28C). These strains are then screened for those that have resolved the delivery vector (i.e. apramycin sensitive for pKC1139 delivery constructs). The wild-type and mutant colonies are then distinguished by PCR screening for the ΔvioMNOP mutation.

The resulting ΔvioMNOP mutants are grown under conditions optimized for viomycin production (Tam, A. H. -K., and D. C. Jordan, 1972). These mutants are analyzed for viomycin and tuberactinamine A production as described in Example 1 (FIG. 6B). The ΔvioMNOP mutant strain produces tuberactinamine A, not viomycin. The insertional inactivation of any of these genes with an antibiotic resistance gene cassette also results in the production of tuberactinamine A.

The analogous protocol can be followed to delete any one or more other genes from the viomycin biosynthetic cluster including vioB, vioC., vioD, vioK, vioL and vioQ alone or in combination.

2. Production of Tuberactinomycin O.

Tuberactinomycin O differs from viomycin in that it lacks the hydroxylation of the (2S,3R)-capreomycidine ring of residue 5 (FIG. 1). Streptomyces griseoverticillatus var. tuberacticus NRRL3482 is known to make low quantities of tuberactinomycin O, but the strain also generates tuberactinomycins A, B, and N. Using our molecular information of the viomycin biosynthetic gene cluster, Streptomyces sp. ATCC11861 can be engineered to produce solely tuberactinomycin O.

In a procedure analogous to that discussed for tuberactinamine A formation, we use genetic inactivation of a viomycin biosynthetic gene, vioQ, to convert Streptomyces sp. ATCC11861 from producing viomycin, to producing tuberactinomycin O. VioQ encodes the putative residue 5 hydroxylase (Thomas, M. G., et al., 2003). Briefly, the first few codons of vioQ are fused to the final few codons of vioQ using PCR-based cloning. An additional 2 kb on either side of the fusion site is also cloned. This ΔvioQ construct is generated in a delivery vector, and the subsequent introduction of the ΔvioQ onto the Streptomyces sp. ATCC11861 genome follows the protocol outlined above for ΔvioMNOP construction. The resulting strain is grown under conditions optimized for viomycin production (Tam, A. H. -K., and D. C. Jordan, 1972). The ΔvioQ stain generates tuberactinomycin O instead of viomycin.

3. Production of des-carbamoyl-viomycin.

VioL catalyzes the carbamoylation of the β-amino group of residue 4 (FIG. 1) (Thomas, M. G., et al., 2003). By genetically inactivating vioL, the resulting Streptomyces sp. ATCC11861 strain will generate a viomycin derivative lacking the carbamoylation of residue 4. This tuberactinomycin derivative has not been produced naturally, or by using chemical modifications or strain mutagenesis techniques.

In an analogous manner as discussed above, vioL is deleted from the chromosome of *Streptomyces* sp. ATCC11861 using standard techniques. The resulting strain produces des-carbamoyl-viomycin instead of viomycin.

4. Production of Tuberactinamine N.

Tuberactinamine N differs from viomycin by the absence of both the β-Lysine moiety and the hydroxylation of the capreomycidine ring of residue 5 (FIG. 1). Tuberactinamine N has only been generated by acid treatment of tuberactinomycin N (Wakamiya, T., et al., 1977). Through genetic manipulation of *Streptomyces* sp. ATCC11861, this strain is altered to generate tuberactinamine N instead of viomycin. This is accomplished by combining the ΔvioMNOP and ΔvioQ mutations that are discussed above. The resulting strain is grown under standard conditions for viomycin production, however the strain produces tuberactinamine N instead of viomycin.

5. Production of Alternative Tuberactinomycins by Constructing ΔvioMNOP, ΔvioQ, and ΔvioL Mutations in Various Combinations.

As discussed for the production of tuberactinamine N, the deletions discussed in sections 1-3 can be combined to generate new tuberactinomycins that have not been isolated or synthesized. These combinations are summarized in FIG. 8. Importantly, the genetic inactivation of these genes results in the production of only the desired tuberactinomycin instead of a mixture of compounds as previously seen with the random chemical mutagenesis of *Streptomyces griseoverticillatus* var. *tuberacticus* NRRL3482.

EXAMPLE 3

Overproduction and Purification of VioC and VioD

Introducing VioC and VioD into host cells, such as *Streptomyces lividans* or *E. coli*, causes the cells to produce large quantities of either (3S)-hydroxy-(2S)-Arginine or (2S,3R)-capreomycidine. Neither of these molecules are commercially available, but are useful as starting materials in chemical synthesis procedures. In particular, (2S,3R)-capreomycidine chemical synthesis is quite difficult. Total chemical synthesis of capreomycidine for synthetic purposes has resulted in protocols having either six (DeMong and Williams 2003 JACS 125:8561-8565) or seven (DeMong and Willams 2002 Tetrahedron Lett. 42:3529-3532) steps with, at best, a 28% yield. Our recent work has shown we can generate mg quantities of capreomycidine using purified VioC and VioD (approximately 15 mg of (2S,3R)-capreomycidine from 40 mg of (2S)-arginine). Ju et al. (2004). Thus, these enzymes can be used to generate larger quantities of enantiomerically pure (2S,3R)-capreomycidine for downstream use in synthesis procedures, including synthesis of new tuberactinomycins antibiotics. Additionally, since the substrates used in these reactions are present in *Escherichia coli*, these genes cab be introduced into *E. coli* for large scale production of (2S,3R)-capreomycidine.

The genes coding for VioC and VioD were independently PCR amplified from cosmid pVIO-P8C8RH, Thomas et al., 2003, cloned into the overexpression vector pET28b (Novagen), and the resulting plasmids were transformed into *E. coli* BL21(DE3) for overproduction of the proteins with N-terminal hexahistidine affinity tags. Overproduction strains were grown in LB supplemented with kanamycin (50 μg/mL) in 3×1 L batches. For overproduction, 1 L medium was inoculated with 10 mL of a fresh overnight culture of BL21 (DE3) carrying either plasmid. Cultures were grown for 24 hr at 25° C. after which cells were harvested by centrifugation.

Cells overproducing VioC were resuspended in buffer A (30 mL; Tris-HCl pH 8.0 (20 mM), NaCl (300 mM), glycerol (10% v/v)) with imidazole (5 mM). Cells were broken by sonication and cell debris removed by centrifugation. The supernatant was incubated with Ni-NTA Agarose (Qiagen) resin (1 mL) at 4° C. for 1 hr with gentle rocking. The resin was recovered and washed with buffer A containing imidazole (20 mM). VioC was eluted using a step gradient of buffer A plus varying concentrations of imidazole (40, 60, 100, or 250 mM). Fractions containing VioC., based on SDS-PAGE/Coomassie staining, were pooled and dialyzed against buffer B (Tris-HCl pH 8.0 (50 mM), NaCl (100 mM), glycerol (10% v/v)). The same protocol was followed for VioD purification with the exception that PLP (0.1 mM) was included in all buffers. The concentration of VioC was determined spectrophotometrically at 280 nm by use of the calculated molar extinction coefficient of VioC (47,630 $M^{-1}$ $cm^{-1}$). The concentration of VioD was determined by BCA assay (Pierce) using bovine serum albumin as a standard.

VioC and VioD Assays. Reactions monitoring VioC activity contained Na-phosphate pH 7.5 (0.1 M), NaCl (0.1 M), glycerol (10% v/v), Na-ascorbate (1 mM), Na-aKG (1 mM), dithiothreitol (1 mM), FeSO4 (50 μM), 4 (400 μM), and VioC (1 μM). After the desired time of reaction, a sample (25 mL) was removed and added to OPA (Pierce)(25 mL) to derivatize all free primary amines. (Benson, 1975). Derivatized reactants and products were separated by HPLC with a Vydac C18 small pore column at a flow rate of 1 mL $min^{-1}$. The following solvents were used: solvent A—ddH2O and 0.1% trifluoroacetic acid (TFA); solvent B—acetonitrile and 0.1% TFA. The profile for separation was 5 min isocratic development at 91%A/9%B; 20 min linear gradient from 91%A/9%B to 70%A/30%B. The elution of OPA-derivatized product was monitored at A340.

Reactions for monitoring VioD activity contained Na-phosphate pH 7.5 (0.1 M), NaCl (50 mM), glycerol (5% v/v), PLP (0.1 mM), 5 (2 mM), and VioD (25 mg). Termination of the reaction by OPA-derivatization and analysis by HPLC were performed as described for VioC.

VioC was overproduced in Escherichia coli with an N-terminal hexahistidine affinity tag and purified to near homogeneity using nickel-chelate chromatography. To assay for VioC turnover, we developed an assay that utilized Ophthalaldehyde (OPA) derivatization of primary amines in the reaction mixture, followed by separation of derivatized products by high-performance liquid chromatography (HPLC). Using this assay, we detected a new product with an elution time distinct from (2S)-arginine. The appearance of this product peak correlated with the loss of the peak associated with (2S)-arginine, and formation of this product required VioC., (2S)-arginine, $FeSO_4$, and aKG. Furthermore, repeating the reactions with [1-$^{14}$C]-αKG and trapping [$^{14}$C]-$CO_2$ released during VioC turnover, using a protocol established for the analysis of CASs, (Salowe et al., 1990) we determined [$^{14}$C]-$CO_2$ was released from the reaction in a VioC-(2S)-arginine-, and $FeSO_4$-dependent manner. These data are all consistent with the hypothesis that VioC is an αKG-dependent non-heme iron dioxygenase. Collection of the eluted product peak from the HPLC and subsequent analysis of the product by positive electrospray ionization mass spectrometry (ESIMS) gave results consistent with the product being the OPA-derivatized and hydroxylated (2S)-arginine ([M+H]$^+$: observed, 307.6; calculated, 307.1 for $C_{14}H_{18}N_4O_4$).

The product was analyzed by MS and NMR and determined to be (3S)-hydroxy-(2S)-arginine. While the site of hydroxylation was as expected, the surprising finding was the stereochemistry of the C3 hydroxylation. VioC is a homolog of CASs, enzymes that catalyze the hydroxylation of the comparable C3 position of their substrates. However, the hydoxylation by CASs results in the (3R)-hydroxylation (Salowe et al., 1990) rather than the (3S)-hydroxylation catalyzed by VioC.

VioD is a homolog of PLP-dependent enzymes that catalyze β-replacement reactions. VioD catalyzes the replacement of the C3 hydroxyl of (3S)-hydroxy-(2S)-arginine with its own guanido group, thus catalyzing a novel intramolecular cyclization of the side chain of (3S)-hydroxy-(2S)-arginine (FIG. 3B). This proposed mechanism proceeds via a PLP-linked 2,3-dehydroarginine intermediate, consistent with prior precursor labeling studies. (Gould and Minott, 1992) Furthermore, the PLP stabilizes this intermediate, thereby eliminating the need for peptide synthesis to occur prior to desaturation and cyclization of the side chain of (2S)-arginine as previously proposed. (Gould and Minott, 1992)

VioD was overproduced in *E. coli* with an N-terminal hexahistidine affinity tag and purified to near homogeneity using nickel-chelate chromatography. Incubation of purified VioD with (3S)-hydroxy-(2S)-arginine, followed by OPA derivatization and HPLC separation, identified a new product that eluted 0.5 min later than (3S)-hydroxy-(2S)-arginine. The formation of this product peak required VioD and (3S)-hydroxy-(2S)-arginine, and its formation correlated to the loss of the peak associated with (3S)-hydroxy-(2S)-arginine. No change in the elution of (2S)-arginine was observed if (2S)-arginine and VioD were incubated together prior to OPA derivatization and HPLC separation. The product of the VioD reaction was identified by MS and NMR analysis as (2S,3R)-capreomycidine.

We have presented the complete in vitro reconstitution of the (2S,3R)-capreomycidine biosynthetic pathway. The first enzyme, VioC, is an unusual αKG-dependent non-heme iron dioxygenase that catalyzes the stereospecific hydroxylation of the C3 of (2S)-arginine to generate (3S)-hydroxy-(2S)-arginine (FIG. 3B). This product is subsequently recognized by a novel PLP-dependent enzyme, VioD, which catalyzes the C3-replacement of the C3 hydroxyl of (3S)-hydroxy-(2S)-arginine with the guanido group of (3S)-hydroxy-(2S)-arginine (FIG. 3B). This intramolecular cyclization of the side chain of an amino acid by a PLP-dependent enzyme is unprecedented in enzymology. This study establishes the enzymatic steps needed for the biosynthesis of (2S,3R)-capreomycidine, and this two-enzyme pathway is likely to be followed during Tuberactinomycin A, B, N, O and Capreomycin IA, IB, IIA, IIB biosynthesis. Furthermore, as we have previously noted, homologs of VioC and VioD are coded by the biosynthetic gene cluster for Streptothricin F (SttL and SttN, respectively). (Thomas et al., 2003).

Thus, the same mechanism of (2S,3R)-capreomycidine formation will be followed during formation of the streptolidine lactam moiety of the streptothricin antibiotics. This work provides the basis for using these enzymes for combinatorial biosynthesis as well as for the production of enantiomerically pure (2S,3R)-capreomycidine for semisynthetic purposes to introduce new structural diversity into natural products. VioC and VioD enzymes are useful because the availability of (2S,3R)-capreomycidine is one of the major limitations in chemically synthesizing reasonable quantities of tuberactinomycin derivatives and it is difficult to chemically synthesize enantiomerically pure (2S,3R)-capreomycidine.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions included herein are provided to clarify their specific use in the context of the invention.

All patents and publications mentioned in the specification are indicative of the levels of skill of those skilled in the art to which the invention pertains.

One skilled in the art would readily appreciate that the present invention is well adapted to carry out the objects and obtain the ends and advantages mentioned, as well as those inherent therein. The antibiotic compounds, enzymes and methods and accessory methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the following claims. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

REFERENCES

Alexander, F. W., et al. 1994. Evolutionary relationships among pyridoxal-5'-phosphate-dependent enzymes. Regio-specific alpha, beta and gamma families. Eur. J. Biochem. 219:953-60.

Altschul, S. F., et al. 1997. Gapped BLAST and PSI-BLAST: a new generation of protein database search programs. Nucl. Acids Res. 25:3389-3402.

Barnes, P. F., et al. 1991. Tuberculosis in patients with human immunodeficiency virus infection. N. Engl. J. Med. 324:1644-50.

Bartz, Q. R., et al. 1951. Viomycin, a new tuberculostatic antibiotic. Am. Rev. Tuberc. 63:4-6.

Benson, J. R. and P. E. Hare. 1975. Proc. Natl. Acad. Sci. USA. 72: 619-622.

Bibb, M. J., J. M. Ward, and S. N. Cohen. 1985. Nucleotide sequences encoding and promoting expression of three antibiotic resistance genes indigenous to *Streptomyces*. Mol. Gen. Genet. 199:26-36.

Bierman, M., et al. 1992. Plasmid cloning vectors for the conjugal transfer of DNA from *Escherichia coli* to *Streptomyces* spp. Gene 116:43-9.

Bloom, B. R., and J. D. McKinney. 1999. The death and resurrection of tuberculosis. Nat. Med. 5:872-874.

Bloom, B. R., and C. J. Murray. 1992. Tuberculosis: commentary on a reemergent killer. Science 257:1055-64.

Bormann, C. Mohrle, V., and Bruntner, C. 1996. Cloning and heterologous expression of the entire set of structural genes for nikkomycin synthesis from *Streptomyces tendae* Tu901 in *Streptomyces lividans*. J. Bacteriol. 178:1216-1218.

Brautaset, T., et al. 2000. Biosynthesis of the polyene antifungal antibiotic nystatin in *Streptomyces noursei* ATCC 11455: analysis of the gene cluster and deduction of the biosynthetic pathway. Chem. Biol. 7:395-403.

Cane, D. E., and C. T. Walsh. 1999. The parallel and convergent universes of polyketide synthases and nonribosomal peptide synthetases. Chem. Biol. 6:R319-25.

Carter, J. H., 2nd, et al. 1974. Biosynthesis of viomycin. I. Origin of alpha, beta-diaminopropionic acid and serine. Biochemistry 13:1221-7.

Cerdeno, A. M, Bibb, M. J., Challis, G. L. 2001. Analysis of the prodiginine biosynthesis gene cluster of *Streptomyces coelicolor* A3(2): new mechanisms for chain initiation and termination in module multienzymes. Chem. Biol. 119:1-13.

Challis, G. L., J. Ravel, and C. A. Townsend. 2000. Predictive, structure-based model of amino acid recognition by nonribosomal peptide synthetase adenylation domains. Chem. Biol. 7:211-24.

Chater, K. F., and C. J. Bruton. 1985. Resistance, regulatory and production genes for the antibiotic methylenomycin are clustered. EMBO J. 4:1893-7.

Chen, H., Hubbard, B. K, O'Connor, S. E., Walsh, C. T. 2002. Formation of β-hydroxy histidine in the biosynthesis of nikkomycin antibiotics. Chem. Biol. 9:103-112.

Chen, H. and Walsh, C. T. 2001. Coumarin formation in novobiocin biosynthesis: β-hydroxylation of the aminoacyl enzyme tyrosyl-S-NovH by a cytochrome P450 NovI. Chem. Biol. 74: 1-12.

Costilow, R. N., and L. Laycock. 1971. Ornithine cyclase (deaminating). Purification of a protein that converts ornithine to proline and definition of the optimal assay conditions. J. Biol. Chem. 246:6655-60.

Croft, J., P. Chaulet, and D. Maher. 1997. Guidelines for the management of drug-resistant tuberculosis WHO/TB/96.210(Rev.1). World Health Organization.

Daniels, T. M., J. H. Bates, and K. A. Downes. 1994. History of tuberculosis, p. 13-24. In B. R. Bloom (ed.), Tuberculosis: Pathogenesis, protection, and control. ASM Press, Washington, D.C.

Davies, J. 1996. Bacteria on the rampage. Nature 383:219-20.

Dirlam, J. P., et al. 1997. Cyclic homopentapeptides 1. Analogs of tuberactinomycins and capreomycin with activity against vancomycin-resistant enterococci and *Pasteurella*. Bioorg. Medicin. Chem. Lett. 7:1139-1147.

Du, L., et al. 2000. The biosynthetic gene cluster for the antitumor drug bleomycin from *Streptomyces verticillus* ATCC15003 supporting functional interactions between nonribosomal peptide synthetases and polyketide synthase. Chem. Biol. 7:623-642.

Duncan, K., and J. C. Sacchettini. 2000. Approaches to tuberculosis drug development, p. 297-307. In G. F. Haffull and W. R. J. Jacobs (ed.), Molecular genetics of mycobacteria. ASM Press, Washington, D.C.

Dye, C., et al. 2002. Erasing the world's slow stain: strategies to beat multidrug-resistant tuberculosis. Science 295:2042-6.

Ehmann, David E.; et al. 1999 Lysine Biosynthesis in *Saccharomyces cerevisiae*: Mechanism of α-Aminoadipate Reductase (Lys2) Involves Posttranslational Phosphopantetheinylation by Lys5. Biochemistry, 38(19), 6171-6177.

Ehrlich, J., et al. 1951. Antimicrobial activity of *Streptomyces floridae* and of viomycin. Am. Rev. Tuberc. 63:7-16.

Fattorini, L., et al. 1999. Activity of 16 antimicrobial agents against drug-resistant strains of *Mycobacterium tuberculosis*. Microb. Drug Resist. 5:265-70.

Fernandez-Moreno, M. A., C. Vallin, and F. Malpartida. 1997. Streptothricin biosynthesis is catalyzed by enzymes related to nonribosomal peptide bond formation. J. Bacteriol. 179:6929-36.

Figurski, D. H., and D. R. Helinski. 1979. Replication of an origin-containing derivative of plasmid RK2 dependent on a plasmid function provided in trans. Proc. Natl. Acad. Sci. USA 76:1648-52.

Finlay, A. C., et al. 1951. Viomycin a new antibiotic active against mycobacteria. Am. Rev. Tuberc. 63:1-3.

Frey, P. A. 1993. Lysine 2,3-aminomutase: is adenosylmethionine a poor man's adenosylcobalamin? FASEB J. 7:662-70.

Frieden, T. R., et al. 1993. The emergence of drug-resistant tuberculosis in New York City. N. Engl. J. Med. 328:521-6.

Goble, M. 1994. Drug Resistance, p. 259-284. In L. N. Friedman (ed.), Tuberculosis: current concepts and treatment. CRC Press Inc., Boca Roton, Fla.

Gould, S. J., and K. J. Martinkus. 1981 a. Biosynthesis of streptothricin F. 1. Observing the interaction of primary and secondary metabolism with [1,2-$^{13}C_2$]acetate. J. Amer. Chem. Soc. 103:2871-2872.

Gould, S. J., and K. J. Martinkus. 1981b. Studies of nitrogen metabolism using carbon-13 NMR spectroscopy. 2. Incorporation of L-[guanido-$^{13}$C,$^{15}N_2$]arginine and DL-[guanido-13C, 2-15N]arginine into streptothricin F. J. Amer. Chem. Soc. 103:4639-4640.

Gould, S. J., and D. A. Minott. 1992. Biosynthesis of capreomycin: 1. Incorporation of arginine. J. Org. Chem. 57:5214-5217.

Grammel, N., et al. 2002. A beta-lysine adenylating enzyme and a beta-lysine binding protein involved in poly beta-lysine chain assembly in nourseothricin synthesis in *Streptomyces noursei*. Eur. J. Biochem. 269:347-57.

Gupta, R., et al. 2001. Public health. Responding to market failures in tuberculosis control. Science 293:1049-51.

Hojati, Z., et al. 2002. Structure, biosynthetic origin, and engineered biosynthesis of calcium-dependent antibiotics from *Streptomyces coelicolor*. Chemistry and Biology. 9:1175-1187

Hermann, T., and E. Westhof. 1998. RNA as a drug target: chemical, modelling, and evolutionary tools. Curr. Opin. Biotechnol. 9:66-73.

Herr, E. B. J., R. L. Hamill, and J. M. McGuire. 1962. Capreomycin and its preparation. U.S. Pat. No. 3,143, 168.

Hobby, G. L., T. F. Lenert, M. Donikian, and D. Pikula. 1953. The activity of viomycin against *Mycobacterium tuberculosis* and other microorgansims in vitro and in vivo. Am. Rev. Tuberc. 63:17-24.

Jackson, M. D., S. J. Gould, and T. M. Zabriskie. 2002. Studies on the formation and incorporation of streptolidine in the biosynthesis of the peptidyl nudleoside antibiotic streptothricin F. J. Org. Chem. 67:2934-2941.

James, H. A., and 1. Gibson. 1998. The therapeutic potential of ribozymes. Blood 91:371-82.

Jenne, A., et al. 2001. Rapid identification and characterization of hammerhead-ribozyme inhibitors using fluorescence-based technology. Nat. Biotechnol. 19:56-61.

Ju, Hianhua, S.G. Ozanick, B. Shen, and M.G. Thomas. 2004. Conversion of (2S)-Arginine to (2S,3R)-Capreomycidine by VioC and VioD from the Viomycin Biosynthetic Pathway of *Streptomyces* sp. strain ATCC11861. ChemBioChem 5: 1-9 (in press).

Keating, T. A., C. G. Marshall, and C. T. Walsh. 2000. Vibriobactin biosynthesis in Vibrio cholerae: VibH is an amide synthase homologous to nonribosomal peptide synthetase condensation domains. Biochemistry 39:15513-21.

Kieser, T., M. J. Bibb, M. J. Buttner, K. F. Chater, and D. A. Hopwood. 2000. Practical Streptomyces Genetics, p. 249-250. The John Innes Foundation, Norwich, England.

Kieser, T., et al. 2000a. Gene disruption and gene replacement, p. 311-337, Practical *Streptomyces* genetics. The John Innes Foundation, Norwich, UK.

Kieser, T., et al. 2000b. Introduction of DNA into *Streptomyces*, p. 229-252, Practical *Streptomyces* genetics. The John Innes Foundation, Norwich, UK.

Kitagawa, T., T. Miura, and H. Kurose. 1979. Studies on viomycin. XIV. Roles of basic and cyclic moieties in the antimicrobial activity of viomycin. Chem. Pharm. Bull. 27:2551-2556.

Kitagawa, T., T. Miura, C. Takaishi, and H. Taniyama. 1976. Studies on viomycin. IX. Amino acid derivatives of viomycin. Chem. Pharm. Bull. 24:1324-1330.

Kitagawa, T., T. Miura, M. Takaishi, and H. Taniyama. 1975. Studies on viomycin. VIII. Selective modifications of the terminal amino groups of viomycin. Chem. Pharm. Bull. 23:2123-2127.

Konz, D., and M. A. Marahiel. 1999. How do peptide synthetases generate structural diversity? Chem. Biol. 6:R39-48.

Kramnik, I., W. F. Dietrich, P. Demant, and B. R. Bloom. 2000. Genetic control of resistance to experimental infection with virulent Mycobacterium tuberculosis. Proc. Natl. Acad. Sci. USA 97:8560-8565.

Lawn, S. D., S. T. Butera, and T. M. Shinnick. 2002. Tuberculosis unleashed: the impact of human immunodeficiency virus infection on the host granulomatous response to *Mycobacterium tuberculosis*. Microbes Infect. 4:635-46.

Legrain, C., and V. Stalon. 1976. Ornithine carbamoyltransferase from *Escherichia coli* W. Purification, structure and steady-state kinetic analysis. Eur. J. Biochem. 63:289-301.

Linde II, R. G., et al. 1997. Cyclic homopentapeptides 3. Synthetic modifications to the capreomycins and tuberactinomycins: Compounds with activity against methicillin-resistant *Staphylococcus aureus* and vancomycin-resistant enterococci. Bioorg. Medic. Chem. Lett. 7:1149-1152.

Lyssikatos, J. P., et al. 1997. Cyclic homopentapeptides 2. Synthetic modifications of viomycin. Bioorg. Medic. Chem. Lett. 7:1145-1148.

MacNeil, D. J., K. M. Bewain, C. L. Ruby, G. Dezeny, P. H. Gibbons, and T. MacNeil. 1992. Analysis of *Streptomyces avermitilis* genes required for avermectin biosynthesis utilizing a novel integration vector. Gene 111:61-69.

Mansouri, K., and W. Piepersberg. 1991. Genetics of streptomycin production in *Streptomyces griseus*: nucleotide sequence of five genes, strFGHlK, including a phosphatase gene. Mol. Gen. Genet. 228:459-69.

Marahiel, M. A., T. Stachelhaus, and H. D. Mootz. 1997. Modular peptide synthetases involved in nonribosomal peptide synthesis. Chem. Rev. 97:2651-2673.

Marsh, W. S., R. L. Mayer, R. P. Mull, C. R. Scholz, and R. W. Towsley. 1953.

Marsh, W.S., et al. 1953. Antibiotics and method for preparing the same. U.S. Pat. No. 2,633,445.

Martin, J. F. 1992. Clusters of genes for the biosynthesis of antibiotics: regulatory genes and overproduction of pharmaceuticals. J. Ind. Microbiol., 9:73-90.

Martin, M. F., and P. Liras. 1989. Organization and expression of genes involved in the biosynthesis of antibiotics and other secondary metabolites. Annu. Rev. Microbiol. 43:173-206.

Martinkus, K. J., C. H. Tann, and S. J. Gould. 1983. The biosynthesis of streptothricin F. Part 4. The biosynthesis of the streptolidine moiety in streptothricin F. Tetrahedron 39:3493-3505.

Mason, J. R., and R. Cammack. 1992. The electron-transport proteins of hydroxylating bacterial dioxygenases. Annu. Rev. Microbiol. 46:277-305.

Mayer, R. L., P. C. Eisman, and E. A. Konopka. 1954. Antituberculosis activity of vinactane. Experimentis 10:335-336.

Morse, B. K., et al. 1997. Production of tuberactinamine A by *Streptomyces griseoverticillatus* var. *tuberacticus* NRRL 3482 fed with (S)-2-aminoethyl-L-cysteine. J Antibiot (Tokyo) 50:698-700.

Murray, C. J. L., and J. A. Salomon. 1998. Modeling the impact of global tuberculosis control strategies. Proc. Natl. Acad. Sci. USA 95:13881-13886.

Muth, W. L., and R. N. Costilow. 1974a. Ornithine cyclase (deaminating). II. Properties of the homogeneous enzyme. J. Biol. Chem. 249:7457-62.

Muth, W. L., and R. N. Costilow. 1974b. Ornithine cyclase (deaminating). III. Mechanism of the conversion of ornithine to proline. J. Biol. Chem. 249:7463-7.

Nagata, A., T. Ando, R. Izumi, H. Sakakibara, and T. Take. 1968. Studies on tuberactinomycin (tuberactin), a new antibiotic. I. Taxonomy of producing strain, isolation and characterization. J. Antibiot. 21:681-7.

Nowak-Thompson, B., Chaney, N., Wing, J. S., Gould, S. J., and Loper, J. E. 1999. Characterization of the pyoluteorin biosynthetic gene cluster of *Pseudomonas fluorescens* Pf-5. J. Bacteriol. 181:2166-2174

Pootoolal, J., et al. 2002. Assembling the glycopeptide antibiotic scaffold: The biosynthesis of A47934 from *Streptomyces toyocaensis* NRRL15009. Proc. Natl. Acad. Sci. USA 99:8962-7.

Quadri, L. E., et al. 1998. Identification of a *Mycobacterium tuberculosis* gene cluster encoding the biosynthetic enzymes for assembly of the virulence-conferring siderophore mycobactin. Chem. Biol. 5:631-45.

Rogers, J., et al. 1996. Inhibition of the self-cleavage reaction of the human hepatitis delta virus ribozyme by antibiotics. J Mol. Biol. 259:916-25.

Salowe, S. P., E. N. Marsh, and C. A. Townsend. 1990. Purification and characterization of clavaminate synthase from *Streptomyces clavuligerus*: an unusual oxidative enzyme in natural product biosynthesis. Biochemistry 29:6499-508.

Schroeder, R., C. Waldsich, and H. Wank. 2000. Modulation of RNA function by aminoglycoside antibiotics. EMBO J. 19:1-9.

Seno and Baltz, 1989. Structural organization and regulation of antibiotic biosynthesis and resistance genes in actinomycetes, CRC Press, Boca Raton, Fla.

Shigeto, E., I. Murakami, and Y. Yokosaki. 2001. A case of drug-resistant pulmonary tuberculosis treated successfully following disappearance of rifampicin resistance after 17 years chemotherapy. Kekkaku 76:379-83.

Stachelhaus, T., H. D. Mootz, and M. A. Marahiel. 1999. The specificity-conferring code of adenylation domains in nonribosomal peptide synthetases. Chem. Biol. 6:493-505. Stachelhaus, Torsten; Marahiel, Mohamed A. 1995. Modular structure of peptide synthetases revealed by dissection of the multifunctional enzyme GrsA. J. Biol. Chem. 270:6163-6169.

Steffensky, M. Muhlenweg, A. et aL 2000. Identification of the novobiocin biosynthetic gene cluster of *Streptomyces spheroids* NCIB 11891. Antimicrob. Agents Chemother. 44:1214-1222.

Tahaoglu, K., et al. 2001. The treatment of multidrug-resistant tuberculosis in Turkey. N. Engl. J. Med. 345:170-4.

Tam, A. H.-K., and D. C. Jordan. 1972. Laboratory production and $^{14}$C-labelling of viomycin. J. Antibiotics 25:524-529.

Thomas, M. G., M. D. Burkart, and C. T. Walsh. 2002. Conversion of L-proline to pyrrolyl-2-carboxyl-S-PCP during undecylprodigiosin and pyoluteorin biosynthesis. Chem. Biol. 9:171-84.

Thomas, M. G., Y. A. Chan, and S. G. Ozanick. 2003. Deciphering tuberactinomycin biosynthesis: Isolation, sequencing, and annotation of the viomycin biosynthetic gene cluster. Antimicrob Agents Chemother, 47: 2823-2830.

Thorpe, C., and J. J. Kim. 1995. Structure and mechanism of action of the acyl-CoA dehydrogenases. FASEB J. 9:718-25.

Townsend, C. A. 2002. New reactions in clavulanic acid biosynthesis. Curr. Opin. Chem. Biol. 6:583-9.

Trauger, J. W. and Walsh, C. T. 2000. Heterologous expression in *Escherichia coli* of the first module of the nonribosomal peptide synthetase of chloroeremomycin, an vancomycin-type glycopeptide antibiotic. 97:3112-3117.

Tsukamura, M., S. Ichiyama, and T. Miyachi. 1989. Superiority of enviomycin or streptomycin over ethambutol in initial treatment of lung disease caused by *Mycobacterium avium* complex. Chest 95:1056-8.

van Wageningen, A. M. A., et al. 1998. Sequencing and analysis of genes involved in the biosynthesis of a vancomycin group antibiotic. Chem. Biol. 5:155-162.

von Ahsen, U., J. Davies, and R. Schroeder. 1991. Antibiotic inhibition of group I ribozyme function. Nature 353:368-70.

Vos, S., D. J. Berrisford, and J. M. Avis. 2002. Effect of magnesium ions on the tertiary structure of the hepatitis C virus IRES and its affinity for the cyclic peptide antibiotic viomycin. Biochemistry 41:5383-96.

Wakamiya, T., T. Teshima, H. Sakakibara, K. Fukukawa, and T. Shiba. 1977. Chemical studies on tuberactinomyin. Xl. Semisyntheses of tuberactinomycin analogs with various amino acids in branched part. Bull. Chem. Soc. Jap. 50:1984-1989.

Wang, M., and S. J. Gould. 1993. Biosynthesis of capreomycin. 2. Incorporation of L-serine, L-alanine, and L-2, 3-diaminopropionic acid. J. Org. Chem. 58:5176-5180.

Wank, H., J. Rogers, J. Davies, and R. Schroeder. 1994. Peptide antibiotics of the tuberactinomycin family as inhibitors of group I intron RNA splicing. J. Mol. Biol. 236:1001-10.

Wank, H., and R. Schroeder. 1996. Antibiotic-induced oligomerisation of group I intron RNA. J. Mol. Biol. 258:53-61.

Whitman, W. B., D. C. Coleman, and W. J. Wiebe. 1998. Prokaryotes: the unseen majority. Proc. Natl. Acad. Sci. USA 95:6578-83.

WHO. 2002. Who Model List of Essential Medicines. WHO Drug Information 16:139-151.

The invention claimed is:

1. An isolated and purified nucleic acid molecule comprising at least a functional fragment of a viomycin biosynthetic gene cluster that encodes a VioA gene product having at least 95% sequence identity to the amino acid sequence of SEQ ID NO:2, wherein the VioA gene product is a non-ribosomal peptide synthetase product capable of forming a peptide bond between a dipeptide that comprises L-2,3-diaminopropionate and L-serine and a second L-serine.

2. The nucleic acid of claim 1 comprising the nucleic acid sequence set forth in SEQ ID NO:1 from position 415 through position 36299.

3. The nucleic acid molecule of claim 1 wherein the functional fragment of a viomycin biosynthetic gene cluster encodes at least one additional gene product selected from the group consisting of
   a VioB gene product having an amino acid sequence at least 95% identical to the amino acid sequence set forth in SEQ ID NO:3 and having 2,3-diaminopropionate synthase activity,
   a VioC qene product having an amino acid sequence at least 95% identical to the amino acid sequence set forth in SEQ ID NO:4 and havinq L-arqinine hydroxylase activity,
   a VioD gene product having an amino acid sequence at least 95% identical to the amino acid sequence set forth in SEQ ID NO:5 and having capreomycidine synthase activity,
   a VioE gene product having an amino acid sequence at least 95% identical to the amino acid sequence set forth in SEQ ID NO:6 and having permease activity,
   a VioF gene product having an amino acid sequence at least 95% identical to the amino acid sequence set forth in SEQ ID NO:7 and having non-ribosomal peptide synthetase carrier protein activity conveying L-2,3-diaminopropionate to the VioA gene product,
   a VioG gene product having an amino acid sequence at least 95% identical to the amino acid sequence set forth in SEQ ID NO:8 and having non-ribosomal peptide synthetase pentapeptide cyclization activity,
   a VioH gene product having an amino acid sequence at least 95% identical to the amino acid sequence set forth in SEQ ID NO:9 and having Tyoe II thioestererase activity,
   a VioI gene product having an amino acid sequence at least 95% identical to the amino acid sequence set forth in SEQ ID NO:10 and having non-ribosomal peptide synthetase carrier protein activity conveyinq a desaturated 2,3-diaminopropionate-comprising tetrapeptide to the VioG gene product,
   a VioJ gene product having an amino acid sequence at least 95% identical to the amino acid sequence set forth in SEQ ID NO:11 and having 2,3-diaminopropionyl α,β-desaturase activity,
   a VioK gene product having an amino acid sequence at least 95% identical to the amino acid sequence set forth in SEQ ID NO:12 and having ornithine cyclodeaminase activity,
   a VioL gene product having an amino acid sequence at least 95% identical to the amino acid sequence set forth in SEQ ID NO:13 and having carbamoyltransferase activity,
   a VioM gene product having an amino acid sequence at least 95% identical to the amino acid sequence set forth in SEQ ID NO:14 and having non-ribosomal peptide synthetase condensation β-lysine transferase activity,
   a VioN gene product having an amino acid sequence at least 95% identical to the amino acid sequence set forth in SEQ ID NO:15 and having β-lysine addition activity,
   a VioO gene product having an amino acid sequence at least 95% identical to the amino acid sequence set forth in SEQ ID NO:16 and having non-ribosomal peptide synthetase carrier protein β-lysine thioesterification activity,
   a VioP gene product having an amino acid sequence at least 95% identical to the amino acid sequence set forth in SEQ ID NO:17 and having lysine 2,3-aminomutase activity,
   a VioQ gene product having an amino acid sequence at least 95% identical to the amino acid sequence set forth in SEQ ID NO:19 and having capreomycidine hydroxylase activity,
   a VioR gene product having an amino acid sequence at least 95% identical to the amino acid sequence set forth in SEQ ID NO:20 and having transcriptional regulatory activity, a VioS gene product having an amino acid sequence at least 95% identical to the amino acid sequence set forth in SEQ ID NO:21 and having viomycin-phosphate phosphatase activity, and a VioT gene product having the amino acid sequence set forth in SEQ ID NO:22 and having transcriptional regulatory activity.

4. The nucleic acid molecule of claim 1 which further encodes a VioB gene product having an amino acid sequence at least 95% identical to the amino acid sequence set forth in SEQ ID NO:3 and having 2,3-diaminopropionate synthase activity, a VioC gene product having an amino acid sequence at least 95% identical to the amino acid sequence set forth in SEQ ID NO:4 and having L-arginine hydroxylase activity, a VioD gene product having an amino acid sequence at least 95% identical to the amino acid sequence set forth in SEQ ID NO:5 and having capreomycidine synthase activity, and a VioG gene product having an amino acid sequence at least 95% identical to the amino acid sequence set forth in SEQ ID NO:8 and having non-ribosomal peptide synthetase pentapeptide cyclization activity, and additionally encodes at least one other gene product selected from the group of gene products consisting of a VioE gene product having an amino acid sequence at least 95% identical to the amino acid sequence set forth in SEQ ID NO:6 and having permease activity, a VioF gene product having an amino acid sequence at least 95% identical to the amino acid sequence set forth in SEQ ID NO:7 and having non-ribosomal peptide synthetase carrier protein activity conveying L-2,3-diaminopropionate to the VioA gene product, a VioH gene product having an amino acid sequence at least 95% identical to the amino acid sequence set forth in SEQ ID NO:9 and having Type II thioestererase activity, a VioI gene product having an amino acid sequence at least 95% identical to the amino acid sequence set forth in SEQ ID NO:10 and having non-ribosomal peptide synthetase carrier protein activity conveying a desaturated 2,3-diaminopropionate-comprising tetrapeptide to the VioG gene product, a VioJ gene product having an amino acid sequence at least 95% identical to the amino acid sequence set forth in SEQ ID NO:11 and having 2,3-diaminopropionyl α,β-desaturase activity, a VioK gene product having an amino acid sequence at least 95% identical to the amino acid sequence set forth in SEQ ID NO:12 and having ornithine cyclodeaminase activity, a VioL gene product having an amino acid sequence at least 95% identical to the amino acid sequence set forth in SEQ ID NO:13 and having carbamoyltransferase activity, a VioM gene product having an amino acid sequence at least 95% identical to the amino acid sequence set forth in SEQ ID NO:14 and having non-ribosomal peptide synthetase condensation β-lysine transferase activity, a VioN gene product having an amino acid sequence at least 95% identical to the amino acid sequence set forth in SEQ ID NO:15 and having β-lysine addition activity, a VioO gene product having an amino acid sequence at least 95% identical to the amino acid sequence set forth in SEQ ID NO:16 and having non-ribosomal peptide synthetase carrier protein β-lysine thioesterification activity, a VioP gene product having an amino acid sequence at least 95% identical to the amino acid sequence set forth in SEQ ID NO:17 and having lysine 2,3-aminomutase activity, a VioQ gene product having an amino acid sequence at least 95% identical to the amino acid sequence set forth in SEQ ID NO:19 and having capreomycidine hydroxylase activity, a VioR gene product having an amino acid sequence at least 95% identical to the amino acid sequence set forth in SEQ ID NO:20 and having transcriptional regulatory activity, a VioS gene product having an amino acid sequence at least 95% identical to the amino acid sequence set forth in SEQ ID NO:21 and having viomycin-phosphate phosphatase activity, and a VioT gene product having the amino acid sequence set forth in SEQ ID NO:22 and having transcriptional regulatory activity.

5. The nucleic acid molecule of claim 1 which further encodes a VioM gene product having an amino acid sequence at least 95% identical to the amino acid sequence set forth in SEQ ID NO:14 and having non-ribosomal peptide synthetase condensation β-lysine transferase activity, a VioN gene product having an amino acid sequence at least 95% identical to the amino acid sequence set forth in SEQ ID NO:15 and having β-lysine addition activity, a VioO gene product having an amino acid sequence at least 95% identical to the amino acid sequence set forth in SEQ ID NO:16 and having non-ribosomal peptide synthetase carrier protein β-lysine thioesterification activity, and a VioP gene product having an amino acid sequence at least 95% identical to the amino acid sequence set forth in SEQ ID NO:17 and having lysine 2,3-aminomutase activity.

6. The nucleic acid molecule of claim 1 which further encodes a VioC gene product having an amino acid sequence at least 95% identical to the amino acid sequence set forth in SEQ ID NO:4 and having L-arginine hydroxylase activity and a VioD gene product having an amino acid sequence at least 95% identical to the amino acid sequence set forth in SEQ ID NO:5 and having capreomycidine synthase activity.

7. The isolated and purified nucleic acid molecule of claim 1 further comprising genes that encode for a gene product selected from the group consisting of a VioF gene product having an amino acid sequence at least 95% identical to the amino acid sequence set forth in SEQ ID NO:7 and having non-ribosomal peptide synthetase carrier protein activity conveying L-2,3-diaminopropionate to the VioA gene product, a VioG gene product having an amino acid sequence at least 95% identical to the amino acid sequence set forth in SEQ ID NO:8 and having non-ribosomal peptide synthetase pentapeptide cyclization activity, a VioI gene product having an amino acid sequence at least 95% identical to the amino acid sequence set forth in SEQ ID NO:10 and having non-ribosomal peptide synthetase carrier protein activity conveying a desaturated 2,3-diaminopropionate-comprising tetrapeptide to the VioG gene product, a VioM gene product having an amino acid sequence at least 95% identical to the amino acid sequence set forth in SEQ ID NO:14 and having non-ribosomal peptide synthetase condensation β-lysine transferase activity, and a VioO gene product having an amino acid sequence at least 95% identical to the amino acid sequence set forth in SEQ ID NO:16 and having non-ribosomal peptide synthetase carrier protein β-lysine thioesterification activity.

8. The nucleic acid molecule of claim 1 comprising a nucleic acid sequence which further encodes one or more polypeptides having an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22.

9. The nucleic acid molecule of claim 1 wherein the nucleic acid sequence has at least 80% nucleic acid sequence identity with the nucleic acid sequence set forth in SEQ ID NO:1 from position 415 through position 6786.

10. The nucleic acid molecule of claim 9, wherein the nucleic acid sequence identity is at least 90% with the nucleic acid sequence set forth in SEQ ID NO:1 from position 415 through position 6786.

11. The nucleic acid molecule of claim 9, wherein the nucleic acid sequence identity is at least 95% with the nucleic acid sequence set forth in SEQ ID NO:1 from position 415 through position 6786.

12. The nucleic acid molecule of claim 1 which is from a wild-type *Streptomyces* sp. ATCC11861, *Streptomyces californicus*, or *Streptomyces olivoreticulis* subsp. *Olivoreticuli*.

13. The nucleic acid molecule of claim 12 which is from wild-type *Streptomyces* sp. ATCC11861.

14. The nucleic acid molecule of claim 1 comprising a viomycin gene cluster.

15. An expression cassette comprising the nucleic acid molecule of claim 1 operably linked to a promoter functional in a host cell, wherein the expression of the cassette in a host transformed with the cassette permits the production of viomycin by the host cell.

16. The expression cassette of claim 15, wherein the nucleic acid molecule further encodes at least one additional gene product selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22, and wherein the expression of the cassette in a host cell comprising the nucleic acid permits the production of viomycin by the host cell.

17. The expression cassette of claim 16, wherein the nucleic acid molecule further encodes the gene products comprising SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22, and wherein the expression of the cassette in a host cell comprising the nucleic acid permits the production of viomycin by the host cell.

18. An isolated, recombinant, host cell transformed with at least the nucleic acid molecule of claim 1 and capable of expressing the encoded VioA gene product.

19. The recombinant host cell of claim 18 in which viomycin levels are increased relative to the levels in a corresponding nonrecombinant host cell.

20. The recombinant host cell of claim 18 wherein the recombinant host cell is a prokaryote or a eukaryote host cell.

21. The recombinant host cell of claim 18 wherein the recombinant host cell is a cell of the genus *Streptomyces*.

22. The recombinant host cell of claim 18 wherein the recombinant host cell is *Streptomyces* sp. ATCC11861.

23. The recombinant host cell of claim of claim 18 wherein the nucleic acid molecule further encodes a VioM gene product having an amino acid sequence at least 95% identical to the amino acid sequence set forth in SEQ ID NO:14 and having non-ribosomal peptide synthetase condensation β-lysine transferase activity, a VioN gene product having an amino acid sequence at least 95% identical to the amino acid sequence set forth in SEQ ID NO:15 and having β-lysine addition activity, a VioO gene product having an amino acid sequence at least 95% identical to the amino acid sequence set forth in SEQ ID NO:16 and having non-ribosomal peptide synthetase carrier protein β-lysine thioesterification activity, and a VioP gene product having an amino acid sequence at least 95% identical to the amino acid sequence set forth in SEQ ID NO:17 and having lysine 2,3-aminomutase activity.

24. The recombinant host cell of claim 23 which is a *Saccharothrix mutabolis* subsp. *capreolus* host cell.

25. The recombinant host cell of claim 18 wherein the nucleic acid molecule further encodes a VioC gene product having an amino acid sequence at least 95% identical to the amino acid sequence set forth in SEQ ID NO:4 and having L-arginine hydroxylase activity and a VioD gene product having an amino acid sequence at least 95% identical to the amino acid sequence set forth in SEQ ID NO:5 and having capreomycidine synthase activity.

26. The recombinant host cell of claim 25 wherein the recombinant host cell is *E. coil*.

27. The recombinant host cell of claim 18, wherein the gene cluster further encodes and expresses at least one gene product selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22, and wherein the expression of the nucleic acid in a host cell comprising the nucleic acid permits the production of viomycin by the host cell.

28. The recombinant host cell of claim 27, wherein the gene cluster further encodes and expresses the gene products comprising SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22, and wherein the expression of the nucleic acid in a host cell comprising the nucleic acid permits the production of viomycin by the host cell.

29. A method for preparing viomycin or a pharmaceutically acceptable salt thereof comprising transforming a host cell with the expression cassette of claim 15, culturing the host cell in a culture medium containing assimilable sources of carbon, nitrogen and inorganic salts under aerobic fermentation conditions to yield an increase in the viomycin relative to the level of the viomycin produced by a corresponding untransformed host cell.

30. The method of claim 29 wherein the host cell is a prokaryote or a eukaryote host cell.

31. The method of claim 29 wherein the host cell is a cell of the genus *Streptomyces*.

32. The method of claim 29 wherein the host cell is *Streptomyces* sp. ATCC11861.

33. The method of claim 29 wherein the transforming expression cassette encodes a VioM gene product having an amino acid sequence at least 95% identical to the amino acid sequence set forth in SEQ ID NO:14 and having non-ribosomal peptide synthetase condensation β-lysine transferase activity,
- a VioN qene product having an amino acid sequence at least 95% identical to the amino acid sequence set forth in SEQ ID NO:15 and havinq β-lysine addition activity,
- a VioO gene product having an amino acid sequence at least 95% identical to the amino acid sequence set forth in SEQ ID NO:16 and having non-ribosomal peptide synthetase carrier protein β-lysine thioesterification activity, and
- a VioP gene product having an amino acid sequence at least 95% identical to the amino acid sequence set forth in SEQ ID NO:17 and having lysine 2,3-aminomutase activity.

34. The method of claim 33 wherein the host cell is a prokaryote or a eukaryote host cell.

35. The method of claim 33 wherein the host cell is a cell of the genus *Streptomyces*.

36. The method of claim 33 wherein the host cell is *Streptomyces* sp. ATCC11861.

37. The method of claim 33 wherein the host cell is *Saccharothrix mutabolis* subsp. *capreolus*.

38. The method of claim 29 wherein expression cassette encodes a VioC gene product having an amino acid sequence at least 95% identical to the amino acid sequence set forth in SEQ ID NO:4 and having L-arqinine hydroxylase activity and a VioD gene product having an amino acid sequence at least 95% identical to the amino acid sequence set forth in SEQ ID NO:5 and having capreomycidine synthase activity.

39. The method of claim 38 wherein the host cell is a prokaryote or a eukaryote host cell.

40. The method of claim 38 wherein the host cell is a cell of the genus *Streptomyces*.

41. The method of claim 38 wherein the host cell is *Streptomyces* sp. ATCC11861.

42. The method of claim 38 wherein the host cell is *E. coil*.

43. The method of claim 29 wherein the expression cassette encodes the viomycin gene cluster.

44. The method of claim 43 wherein the host cell is a prokaryote or a eukaryote host cell.

45. The method of claim 43 wherein the host cell is a cell of the genus *Streptomyces*.

46. The method of claim 43 wherein the host cell is *Streptomyces* sp. ATCC11861.

47. An isolated and purified polypeptide having the amino acid sequence of the VioA gene product set forth in SEQ ID NO:2.

* * * * *